(12) United States Patent
Brueck et al.

(10) Patent No.: US 9,239,455 B2
(45) Date of Patent: Jan. 19, 2016

(54) STRUCTURAL ILLUMINATION AND EVANESCENT COUPLING FOR THE EXTENSION OF IMAGING INTERFEROMETRIC MICROSCOPY

(71) Applicants: Steven R. J. Brueck, Albuquerque, NM (US); Alexander Neumann, Albuquerque, NM (US); Yuliya Kuznetsova, Albuquerque, NM (US)

(72) Inventors: Steven R. J. Brueck, Albuquerque, NM (US); Alexander Neumann, Albuquerque, NM (US); Yuliya Kuznetsova, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 497 days.

(21) Appl. No.: 13/629,598

(22) Filed: Sep. 27, 2012

(65) Prior Publication Data
US 2013/0094077 A1    Apr. 18, 2013

Related U.S. Application Data

(60) Continuation-in-part of application No. 13/345,267, filed on Jan. 6, 2012, now Pat. No. 8,526,105, which is a division of application No. 12/347,619, filed on Dec. 31, 2008, now Pat. No. 8,115,992.

(60) Provisional application No. 61/115,246, filed on Nov. 17, 2008, provisional application No. 61/089,669, filed on Aug. 18, 2008, provisional application No. 61/017,985, filed on Dec. 31, 2007.

(51) Int. Cl.
*G02B 21/06* (2006.01)
*G02B 21/00* (2006.01)
*G02B 21/36* (2006.01)
*G06T 3/40* (2006.01)
*G01N 21/65* (2006.01)

(52) U.S. Cl.
CPC ............ *G02B 21/06* (2013.01); *G02B 21/0056* (2013.01); *G02B 21/365* (2013.01); *G06T 3/4061* (2013.01); *G01N 2021/653* (2013.01)

(58) Field of Classification Search
CPC .. G02B 21/00; G02B 21/004; G02B 21/0016; G02B 21/0032; G02B 21/0052; G02B 21/0056; G02B 21/0064; G02B 21/008; G02B 21/06; G02B 21/086; G02B 21/088; G02B 21/36; G02B 21/365
See application file for complete search history.

(56) References Cited

U.S. PATENT DOCUMENTS

| | | | |
|---|---|---|---|
| 6,255,642 B1 | 7/2001 | Cragg et al. | |
| 8,115,992 B2 | 2/2012 | Brueck et al. | |
| 8,526,105 B2 * | 9/2013 | Brueck et al. | 359/385 |
| 2005/0023439 A1 | 2/2005 | Cartlidge et al. | |
| 2007/0013999 A1 | 1/2007 | Marks et al. | |

* cited by examiner

*Primary Examiner* — Thong Nguyen
(74) *Attorney, Agent, or Firm* — MH2 Technology Law Group, LLP

(57) ABSTRACT

In accordance with the aspects of the present disclosure, a method and apparatus is disclosed for imaging interferometric microscopy (IIM), which can use an immersion medium to enhance resolution up to a resolution of linear systems resolution limit of $\lambda/4n$, where $\lambda$ is the wavelength in free space and n is the index of refraction of a transmission medium.

22 Claims, 33 Drawing Sheets

On axis coherent illumination

Off axis illumination (x-direction)

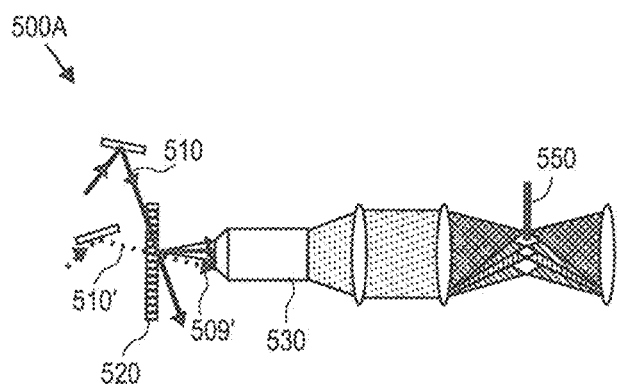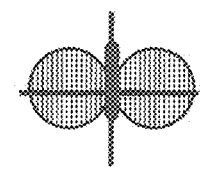
FIG. 5A
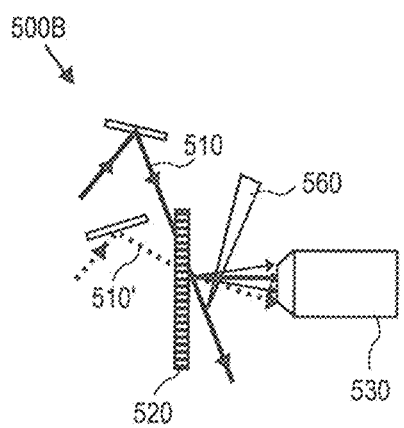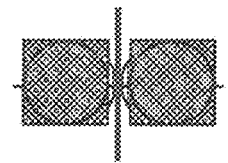
FIG. 5B

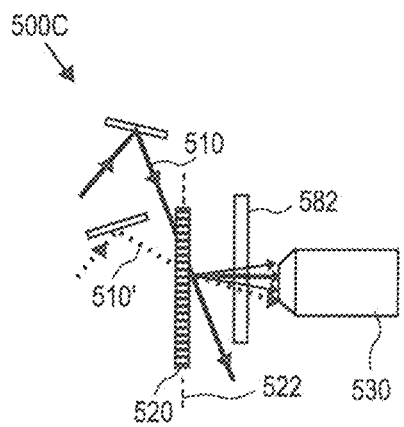
FIG. 5C
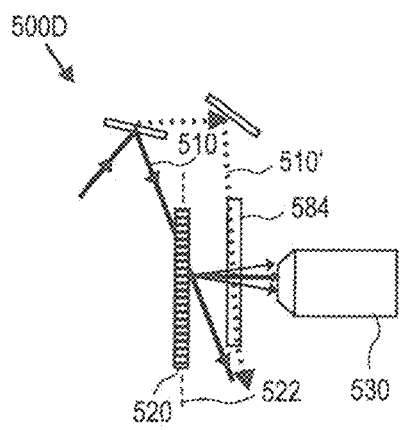
FIG. 5D
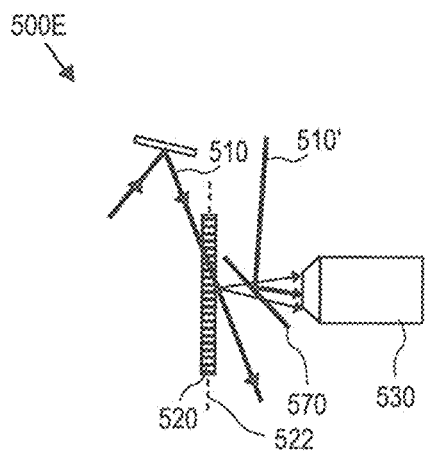
FIG. 5E
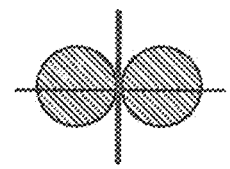

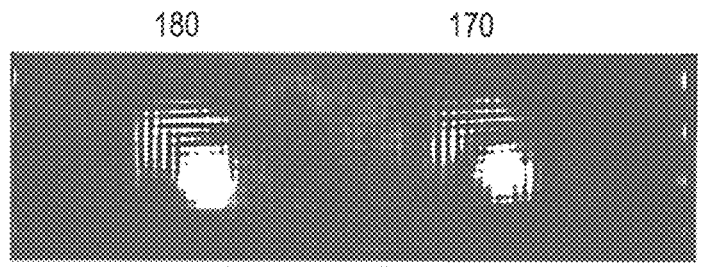
FIG. 15A
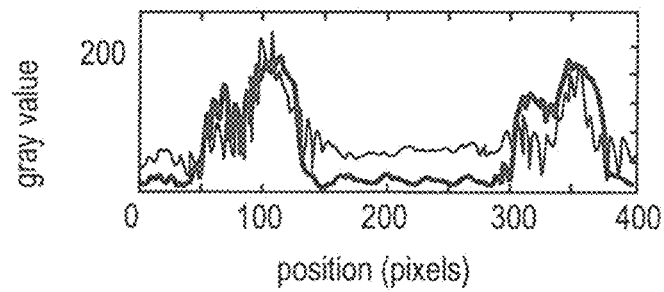
FIG. 15B
FIG. 16A
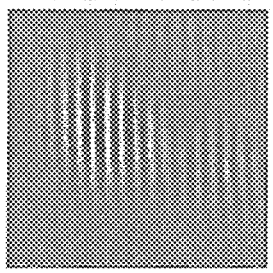
FIG. 16B
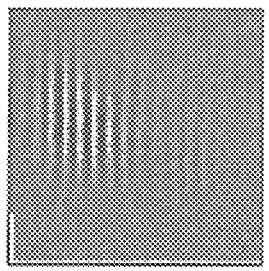
FIG. 16C
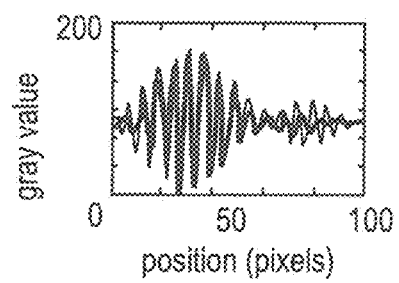
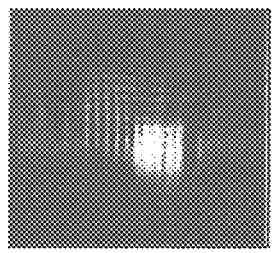
FIG. 16D
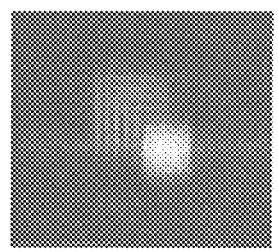
FIG. 16E
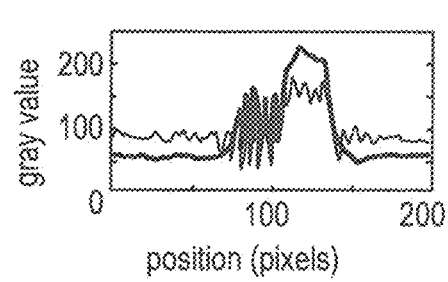
FIG. 16F

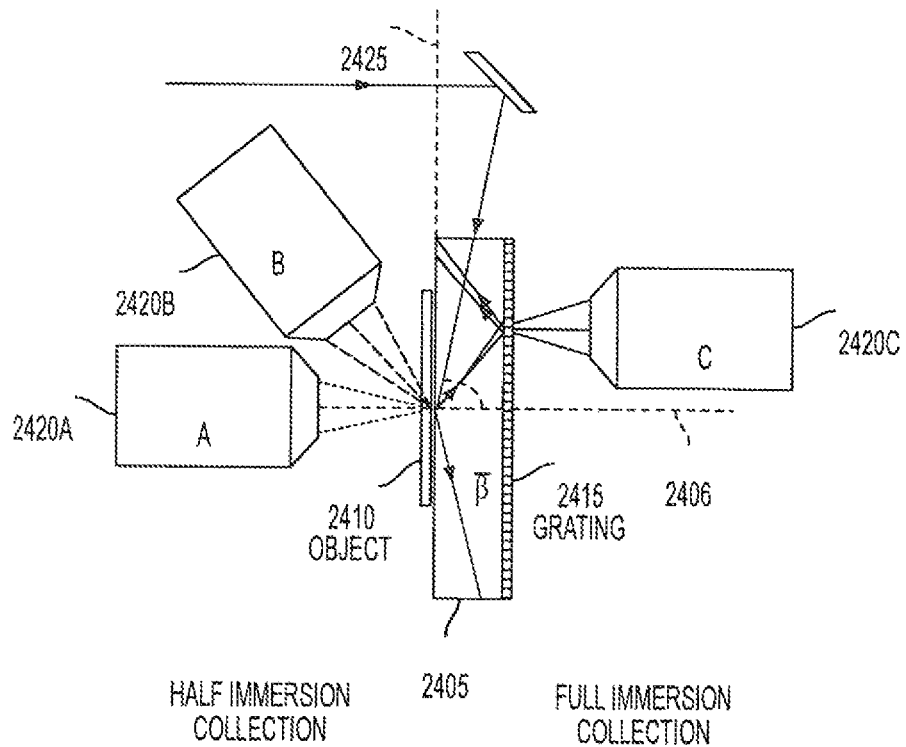
FIGS. 24A-C
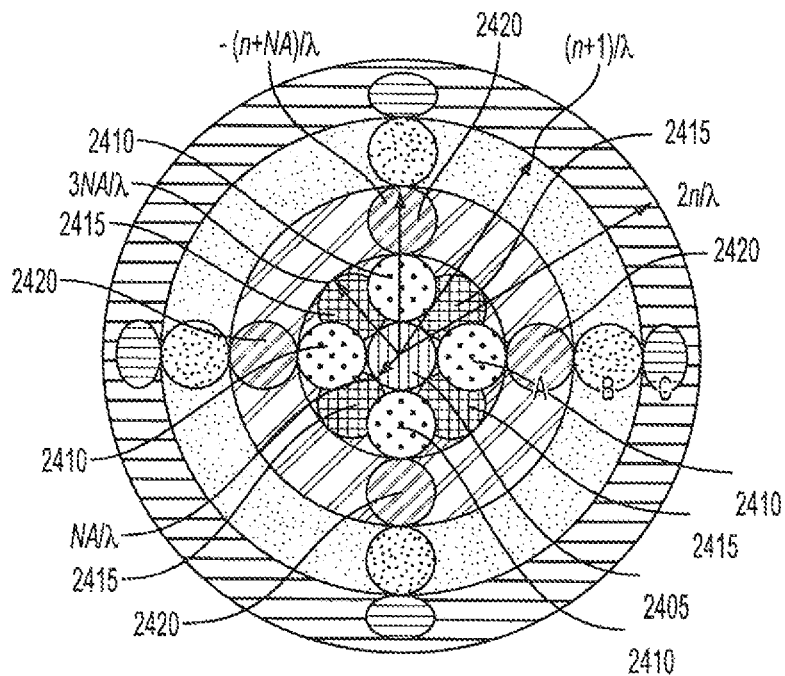
FIG. 24D

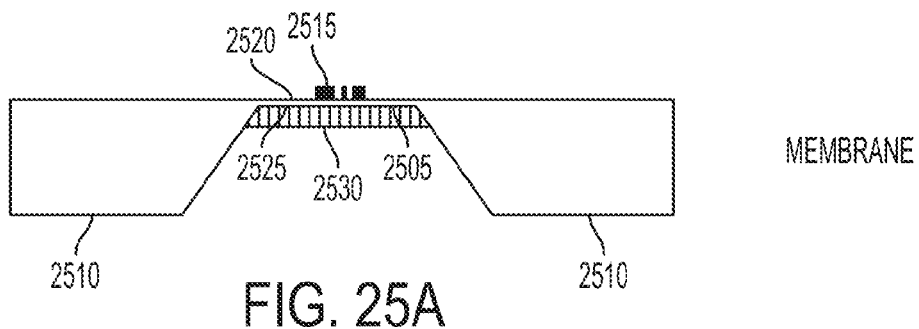
FIG. 25A    MEMBRANE
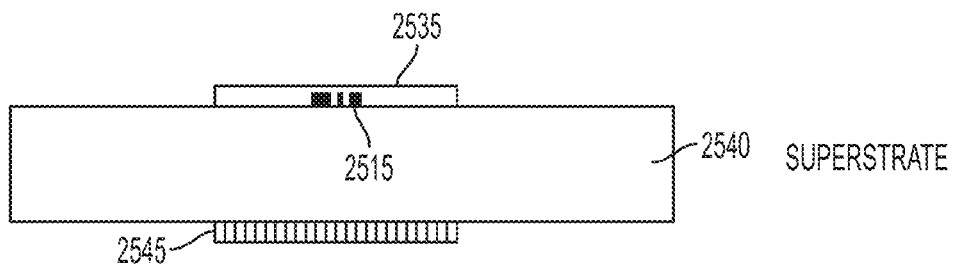
FIG. 25B    SUPERSTRATE
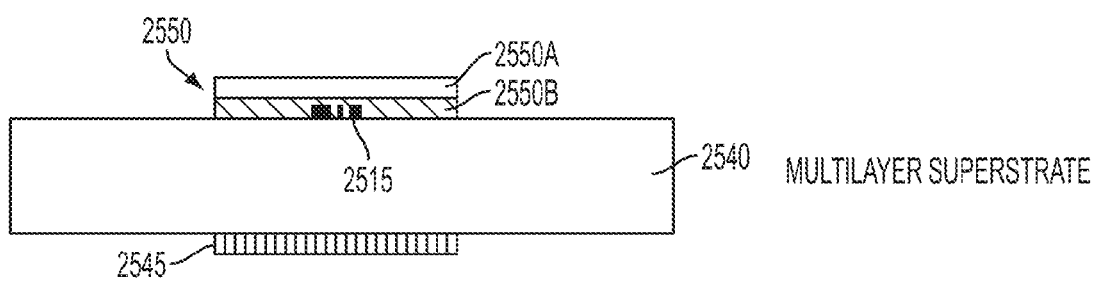
FIG. 25C    MULTILAYER SUPERSTRATE
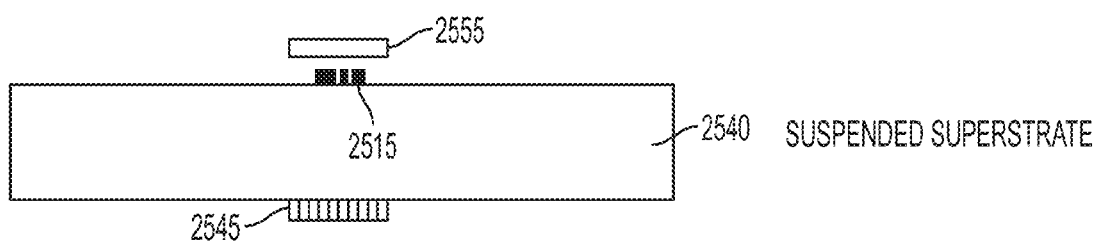
FIG. 25D    SUSPENDED SUPERSTRATE

STRUCTURAL ILLUMINATION AND EVANESCENT COUPLING FOR THE EXTENSION OF IMAGING INTERFEROMETRIC MICROSCOPY

RELATED APPLICATIONS

This application is a continuation-in-part to U.S. patent application Ser. No. 13/345,267 filed on Jan. 6, 2012, which is a divisional of U.S. patent application Ser. No. 12/347,619 filed Dec. 31, 2008 and claims priority from U.S. Provisional Patent Application Ser. Nos. 61/017,985, filed Dec. 31, 2007; 61/089,669, filed Aug. 18, 2008; and 61/115,246, filed Nov. 17, 2008, which are hereby incorporated by reference in their entirety.

GOVERNMENT RIGHTS

This invention was made with government support under Contract Nos. HR0011-05-1-0006 awarded by the Defense Advanced Research Projects Agency and FA9550-06-1-0001 awarded by the Air Force Office of Scientific Research. The government has certain rights in the invention.

FIELD OF THE INVENTION

This invention relates generally to microscopy, and, more particularly, to an imaging interferometric microscope.

BACKGROUND OF THE INVENTION

Optical microscopy is among the oldest applications of optical science and remains one of the most widely used optical technologies. In spite of impressive results obtained by fluorescent microscopy in exceeding the classical diffraction limit, non-fluorescent transmission/reflection microscopy remains an important field of modern research. However, using traditional illumination schemes, resolution is limited to $\sim K_1 \lambda/NA$ where $\lambda$ is the source wavelength and NA is the numerical aperture (sine of the half-acceptance angle) of the imaging objective lens. The "constant" $K_1$ depends on both the details of the image and on the illumination scheme. For example, $K_1$ can be between 0.25 and 1. Hence, traditional approaches to improve resolution are either to use shorter wavelengths and/or to use larger numerical-aperture lenses. For biological samples, however, the wavelength is constrained to the visible spectral range because ultraviolet photons can damage samples. In many practical cases, even for inorganic samples, the wavelength is limited to the deep ultraviolet (for example 193 nm) since transmissive optical materials become difficult at shorter wavelengths (fused quartz has a cutoff at ~185 nm). Furthermore, a disadvantage of using a high-NA lens is the resulting short depth-of-field (an essential feature of achieving high resolution in a single image; typically the depth-of-field scales as $K_2\lambda/NA^2$ where $K_2$ is a second "constant" of order unity). The depth-of-field decreases rapidly as the NA is increased to increase the resolution. In addition, the field of view (the area over which the resolution is achieved) and the working distance (the distance from the final lens surface to the object plane) are reduced for higher-NA optical systems. These latter two issues can be surmounted by more complex objective lenses, with an increase in the cost of manufacturing. These tradeoffs are well known and are discussed in many microscopy overviews.

Synthetic aperture approaches, such as, for example, imaging interferometric microscopy (IIM), extend the collected spatial frequencies to improve the image. IIM, with both illumination and collection in a transmission medium (usually air), uses a low-NA objective and yet provides a resolution approximately a factor of two better than that available even with a high-NA objective using conventional coherent or incoherent illumination. A major advantage is that the depth-of-field, field-of-view and working distance associated with the low-NA system are retained, but the final composite image has a resolution at the linear system limit imposed by the transmission medium ($\gtrsim \lambda/4n$ where $\lambda$ is the wavelength in free space and n is the index of refraction of the transmission medium), and significantly better than that accessible with even a high NA lens using conventional (coherent or incoherent) illumination approaches.

An exemplary IIM with two offset partial images, one each in orthogonal spatial directions can result in an increased resolution by three times using about 0.4-NA objective and 633-nm He—Ne laser. Furthermore, IIM requires building an interferometric system around the objective lens which is an issue for wide-spread adoption of this approach, and in particular towards its adoption to the existing microscopes. In the prior art, this interferometer required additional optics to relay the pupil plane of the collection objective to convenient location; this is straightforward but required significant additional optics. Hence, there is a need for a new approach that does not require a large change to the imaging optical system that comprises the objective lens and subsequent optical components.

The prior art imaging interferometric microscopy was able to image maximum spatial frequency of $2\pi/\lambda$ e.g. to the linear system's limit of the air (transmission medium between the object and the lens). The ultimate linear system limit is $2\pi n/\lambda$, which reflects the use of an immersion medium of refractive index n. Even though materials with refractive indices of up to about 5 are known at some optical wavelengths, the highest numerical aperture available for the immersion microscopy is about 1.4, limited by the refractive index of the glass used to make the lens, by the refractive indices available for the index matching fluids, and the well known difficulties of making aberration corrected optics of high NA. Hence, there is a need for a new approach that can achieve this linear system limit without requiring index-matching fluids or high NA lenses.

As is well-known, using off-axis illumination provides enhanced resolution over that available with either of the standard illumination schemes discussed above, but there is some distortion of the image associated with the resultant non-constant transfer function for different regions of frequency space. This non-uniform frequency-space coverage can be addressed with appropriate pupil plane filters and by combining partial images corresponding to different parts of frequency space, as has been previously demonstrated in the case of imaging interferometric lithography

SUMMARY OF THE INVENTION

In implementations, a method for microscopy is disclosed that includes providing a plane-parallel optical element operable to be positionable adjacent to an object, wherein the plane-parallel optical element is characterized by a homogeneous refractive index ($n_{pp}$) and a thickness ($t_{pp}$), such that a distance of separation between the plane-parallel optical element and the object is within about a wavelength of illumination light incident upon the object; providing a first optical system disposed to provide a substantially coherent illumination of the object, wherein the illumination light is characterized by a wavelength $\lambda$, a radius of curvature, a center position, and a field-of-view and disposed at one of a plurality of incident wave vectors from about 0 to about $2\pi n_{pp}/\lambda$ with respect to a surface normal of the plane-parallel optical element and at a plurality of azimuth angles spanning about 0 to 2π; providing a second optical system including one or more optical components defining an optical axis which is disposed on a side of the plane parallel optical element, the second optical system including a first set of optical media characterized by indices of refraction and thicknesses in which light scattered by the object propagates to the first optical component of the second optical system, an effective numerical aperture ($NA_{pp}$) of the combined one or more optical components of the second optical system, a focal plane of the optical system conjugate with a image plane of an optical image recording device, and a field-of-view in the focal plane, wherein the optical axis of the second optical system is disposed at one of a plurality of angles between 0 and $\pi/2-NA_{pp}$ with respect to the surface normal of the plane-parallel optical element, the field-of-view of the second optical system is located at a center offset from the center position of the illumination provided by the first optical system, and wherein the one or more optical components of the second optical system are operable to collect at least a portion of the illumination scattered by the object; and providing a third optical system disposed in an optical path of the first optical system to provide interferometric reintroduction of a portion of the coherent illumination as a reference beam into the third optical system, wherein each of an amplitude, a phase, a radius of curvature, a path length, and an angle of incidence of the reference beam is adjustable such that a reference illumination suitable for interfering with the portion of the illumination scattered by the object and collected by the second optical system is present at an image plane of the second optical system; recording a sub-image of the object at an image plane of the second optical system using the image recording device, wherein the sub-image is formed as a result of interference between the scattering resulting from the coherent illumination of the object and the reference beam; adjusting the first, the second, and the third optical systems to collect a plurality of sub-images corresponding to a plurality of regions of the object spatial frequency space; and combining the plurality of sub-images into a composite image to provide an image of the object. The subscript "pp" is used to denote the plane-parallel optical element.

In implementations, the second optical system can further comprise one or more gratings on an outward facing surface of the plane parallel optical element, away from the object, the grating being in a far field region of the scattering of the illumination by the object, wherein each grating is characterized by a position, including a center position and a spatial extent, a period, and a grating profile and wherein each grating is operable to decouple a subset of the coherent radiation scattered by the object at angles that are beyond the $NA_{pp}$ of the second optical system into the first optical medium of the second optical system at angles smaller than $\pm\sin^{-1}(NA_{pp})$ of the second optical system.

In implementations, the method can further comprise translating the center offset of the field of view of the second optical system, relative to the center of the field-of-view of the first optical system, to collect subsets of the illumination scattered from the object.

In implementations, the translation of the center offset of the field-of-view of the second optical system can be within an extent of a single grating for which a width of the spatial extent of the grating is greater than the field-of-view of the second optical system, thereby affecting an increased field-of-view of the second optical system.

In implementations, the translation of the center offset of the field-of-view of the second optical system can be larger than a width of a first grating of the one or more gratings, resulting in the field-of-view of the second optical system being positioned over a second grating of the one or more gratings with a different pitch from the first grating, thereby accessing a different subset of the scattered waves from the object.

In implementations, the plane-parallel optical element can be arranged to be physically coupled, and therefore provide, at least a portion of the mechanical support of the object.

In implementations, the plane-parallel optical element can be a superstrate that is arranged to be held or positionable to within about an illumination wavelength of the object.

In implementations, the one or more sub-images can be recorded with the optical axis of the second optical system on the same side of the plane parallel optical element as the object and at an angle between 0 and $\pi/2-NA_{pp}$ relative to the normal of the plane-parallel optical element and the center of field-of-view of the second optical system is positioned over the center of the field-of-view of the first optical system.

In implementations, the one or more sub-images can be recorded with the optical axis of the second optical system on a side of the plane parallel optical element opposite the object, normal to the plane-parallel optical element, and the field-of-view of the second optical system is positioned over one of the one or more gratings, thereby collecting and recording additional spatial frequencies of the illumination scattered by the object.

In implementations, the method can further comprise manipulating each of the sub-images to correct for distortions and alterations introduced by the combinations of the first, the second, and the third optical systems.

In implementations, the providing a third optical system can further comprise collecting a portion of the coherent illumination by splitting the coherent illumination using a beam splitter disposed in an optical path of the first optical system; and interferometrically reintroducing the portion of the coherent illumination as a reference beam after an exit aperture of a collection lens of the second optical system, wherein the reintroduction is at one of a position, an amplitude, a phase, a radius of curvature, a path length, and an angle of incidence such that either a correct sub-image or an aliased sub-image with reduced spatial frequencies is produced.

In implementations, the providing a third optical system can further comprise collecting a portion of the coherent illumination by splitting the coherent illumination using a beam splitter disposed in an optical path of the first optical system; and interferometrically reintroducing the portion of the coherent illumination as a reference beam using a second beam combining device before the entrance aperture of a collection lens of the second optical system, wherein the reintroduction is at an angle less than the acceptance angle of the collection lens of the second optical system, wherein the second beam combining device is selected from the group consisting of: a beamsplitter, a grating coupler, and a waveguide filter.

In implementations, an apparatus for microscopy is disclosed that can comprise a plane parallel optical element, characterized by a homogeneous refractive index ($n_{pp}$) and a thickness ($t_{pp}$), a mechanical mechanism arranged to support an object, such that a separation between the plane parallel optical element and the object is within about a wavelength of an illumination light with which the object is illuminated; a first optical system operable to provide a substantially coherent illumination of the object, the illumination characterized by a wavelength λ, a radius of curvature, a center position, and a field-of-view and disposed at one of a plurality of incident wave vectors from about 0 to about $2\pi n_{pp}/\lambda$, with respect to a surface normal of the substrate and at a plurality of azimuth angles spanning about 0 to $2\pi$; a second optical system; including one or more optical components defining an optical axis operable to be positioned on a side of the plane parallel optical element, the second optical system including a first set of optical media characterized by indices of refraction and thicknesses in which light scattered by the object propagates from the object, a numerical aperture ($NA_{pp}$) of the combined one or more optical components of the second optical system, a focal plane of the object conjugate with an image plane of an image recording device, and a field-of-view in the focal plane; wherein the optical axis of the second optical system can be disposed at one of a plurality of angles between about 0 and about $\pi/2-NA_{pp}$ with respect to the plane parallel optical element surface normal; the field-of-view of the second optical system is located at a center offset from the center position of the illumination provided by the first optical system, and wherein the one or more optical components are operable to collect at least a portion of the illumination scattered by the object; a third optical system operable to be positioned in an optical path of the first optical system to provide interferometric reintroduction of a portion of the coherent illumination as a reference beam into the third optical system, wherein each of an amplitude, a phase, a radius of curvature, a path length, and an angle of incidence of the reference beam is adjustable such that a reference illumination suitable for interfering with the portion of the illumination scattered by the object and collected by the second optical system is present at an image plane of the second optical system; an image recording device operable to record a sub-image of the object at an image plane of the second optical system, wherein the sub-image is formed as a result of interference between the scattering resulting from the coherent illumination of the object and the reference beam; an adjustment mechanism operable to configure the first, the second, and the third optical systems to collect a plurality of sub-images corresponding to a plurality of regions of the object spatial frequency space; and a signal processing device operable to combine the plurality of sub-images into a composite image to provide an image of the object.

In implementations, the second optical system can further comprise one or more gratings on an surface of the plane-parallel optical element opposite the object, the interface being in a far field region of the scattering of the illumination by the object, wherein each grating is characterized by a position, including a center position and a spatial extent, a period, and a grating profile and wherein each grating is operable to decouple a subset of the coherent radiation scattered by the object at angles that are beyond the $NA_{pp}$ of the second optical system into the first optical medium of the second optical system at angles smaller than $\pm\sin^{-1}(NA_{pp})$ of the second optical system.

In implementations, the apparatus can further comprise one or more optical, mechanical, or both optical and mechanical elements operable to translate the center offset of the field of view of the second optical system, relative to the center of the field-of-view of the first optical system, to collect subsets of the illumination scattered from the object.

In implementations, the translation of the center offset of the field-of-view of the second optical system can be within an extent of a single grating for which a width of the spatial extent is greater than the field-of-view of the second optical system, thereby affecting an increased field-of-view of the second optical system.

In implementations, the extent of the translation of the center offset of the field-of-view of the second optical system can be larger than a width of a first grating of the one or more gratings, resulting in the field-of-view of the second optical system being positioned over a second grating of the one or more gratings with a different pitch from the first grating, thereby accessing a different subset of the scattered waves from the object.

In implementations, any, or combinations of, the first, the second, or the third optical systems can be arranged such that one or more sub-images are recorded with the optical axis of the second optical system on a side of the plane-parallel optical element away from the side facing the object and at an angle between about 0 and about $\pi/2-NA_{pp}$ relative to the normal of the plane-parallel optical element and the center of field-of-view of the second optical system is positioned over the center of the field-of-view of the first optical system.

In implementations, the sub-images depend on both the illumination system, for example, the first and the third optical systems, and collection systems, for example, the second optical system. The third optical system can also provide a spatial frequency offset. In implementations, all three optical systems are needed to correctly interpret the sub-image.

In implementation, the second optical system can be arranged such that one or more sub-images are recorded with the optical axis of the second optical system on the outward facing side of the plane-parallel optical element, normal to the plane-parallel optical element, and the field-of-view of the second optical system is positioned over one of the one or more gratings, thereby collecting and recording additional spatial frequencies of the illumination scattered by the object.

In implementation, the apparatus can further comprise one or more electrical, optical, or both electrical and optical element operable to manipulate each of the sub-images to correct for distortions and alterations introduced by the combinations of the first, the second, and the third optical systems.

In implementations, the third optical system can further include one or more optical elements operable to collect a portion of the coherent illumination by splitting the coherent illumination using a beam splitter disposed in an optical path of the first optical system; and one or more optical elements operable to interferometrically reintroduce the portion of the coherent illumination as a reference beam after an exit aperture of a collection lens of the second optical system, wherein the reintroduction is at one of a position, an amplitude, a phase, a radius of curvature, a path length, and an angle of incidence such that either a correct sub-image or an aliased sub-image with reduced spatial frequencies is produced.

In implementations, the third optical system can further include one or more optical elements operable to collect a portion of the coherent illumination by splitting the coherent illumination using a beam splitter disposed in an optical path of the first optical system; and one or more optical elements operable to interferometrically reintroduce the portion of the coherent illumination as the reference beam using one or more optical components before the entrance aperture of a collection lens of the second optical system, wherein the reintroduction is at an angle less than the entrance aperture of the collection lens of the second optical system, wherein the one or more optical components that are operable to reintroduce the reference beam are selected from the group consisting of: a beamsplitter, a grating coupler, and a waveguide filter.

In accordance with various embodiments, an apparatus for coherent anti-Stokes Raman (CARS) microscopy is disclosed. The apparatus can comprises an object plane on which is disposed a first surface of a planar substrate, wherein the substrate is characterized by a homogeneous refractive index and a surface normal, wherein the substrate is arranged to support an object; a first optical system disposed to provide an illumination of the object plane, the illumination characterized by two substantially coincident coherent beams with wavelengths $\lambda_1$ and $\lambda_2$ and corresponding angular frequencies $\omega_1$ and $\omega_2$ with $\omega_1 > \omega_2$, a radius of curvature, and disposed at one of a plurality of incident wave vectors from about 0 to about $2\pi n_{sub}/\lambda_1$ with respect to the surface normal of the substrate and at a plurality of azimuth angles spanning about 0 to about $2\pi$; a second optical system having an optical axis disposed at one of a plurality of center wave vectors from about 0 to about $2\pi n_{sub}/\lambda_1$ with respect to the surface normal of the substrate, wherein the second optical system is characterized by a numerical aperture and is responsive to optical signals at frequencies greater than $\omega_1$; a third optical system disposed between the first optical system and an entrance aperture of a first optical element of the second optical system to provide interferometric reintroduction of the illumination as a reference beam at an angular frequency of $2\omega_1 - \omega_2$ into the second optical system, wherein each of an amplitude, a phase, a radius of curvature and an angle of incidence of the reference beam is arranged to be adjusted such that a corrected reference wave is present at an image plane of the second optical system; an electronic image device disposed at the image plane of the second optical system and operable to respond linearly to a local optical intensity and transfer a local optical intensity map across the image plane as a sub-image to a signal processor device in electronic form; one or more devices operable to adjust the first, the second, and the third optical systems to collect sub-images for different pairs of the pluralities of incident illumination wave vectors from the first optical system and collection angles from the second optical system so as to sequentially obtain a plurality of sub-images corresponding to a plurality of regions of spatial frequency space, wherein the signal processor device is operable to sequentially receive the electronic form of the sub-images and manipulate the sub-images to correct for distortions and alterations introduced by the optical configuration, store, and combine the plurality of sub-images corresponding to the plurality of regions of spatial frequency space to create a composite image. In some aspects, the substrate can be air.

In some aspects, the third optical system can further comprise a first beamsplitter disposed in an optical path of the first optical system before the object to collect a portion of the coherent illumination; and one or more optics disposed between the first optical system and an entrance aperture of a first optical element of the second optical system, wherein the optics comprises a nonresonant nonlinear material configured to generate anti-Stokes four-wave mixing frequency $2\omega_1 - \omega_2$ and exclude the frequencies $\omega_1$ and $\omega_2$ and to interferometrically reintroduce a portion of the anti-Stokes illumination as the reference beam into the second optical system in a position after an exit aperture of a collection lens of the second optical system, wherein the reintroduction is at one of a position corresponding to a position a zero-order beam would have had if it had been transmitted through an appropriate higher numeric aperture lens of the second optical system or an aliased position to reduce pixel requirements of the electronic image device, wherein the signal processor is operable to compensate for spatial frequency aliasing.

In some aspects, the third optical system can further comprise a first beamsplitter disposed in an optical path of the first optical system to collect a portion of the coherent illumination; one or more transfer optics disposed between the first optical system and an entrance aperture of a first optical element of the second optical system, wherein the optics comprises a nonresonant nonlinear material configured to generate anti-Stokes four-wave mixing frequency $2\omega_1 - \omega_2$ and exclude the frequencies $\omega_1$ and $\omega_2$; and a second beamsplitter disposed between the object and an entrance aperture of a collection lens of the second optical system to reintroduce the portion of the anti-Stokes coherent illumination as the reference beam into the second optical system at an angle less than an entrance angular aperture of the second optical system.

In some aspects, the third optical system can further comprise a first beamsplitter disposed in an optical path of the first optical system to collect a portion of the coherent illumination; one or more transfer optics disposed between the first optical system and the second optical system, wherein the optics comprises a nonresonant nonlinear material configured to generate anti-Stokes four-wave mixing frequency $2\omega_1 - \omega_2$ and exclude the frequencies $\omega_1$ and $\omega_2$; and at least one of a grating or a grating on a waveguide disposed between the object and an entrance aperture of a first optical element of the second optical system to reintroduce a portion of the anti-Stokes coherent illumination as the reference beam into the second optical system at an angle less than an entrance angular aperture of the second optical system.

In some aspects, the third optical system can further comprise a first beamsplitter disposed in an optical path of the first optical system to collect a portion of the coherent illumination; one or more transfer optics, wherein the optics comprises a nonresonant nonlinear material configured to generate anti-Stokes four-wave mixing frequency $2\omega_1 - \omega_2$ and exclude the frequencies $\omega_1$ and $\omega_2$; an optical element operable to direct a portion of the anti-Stokes coherent illumination as the reference beam to illuminate the object at an angle corresponding to less than an entrance angular aperture of the second optical system; and a dynamic physical block disposed in a back pupil plane of the second optical system to alternately block and unblock a portion of a pupil aperture corresponding to the position of the reference beam in the aperture.

In some aspects, the third optical system can further comprise a first beamsplitter disposed in an optical path of the first optical system to collect a portion of the coherent illumination; one or more transfer optics, wherein the optics comprises a nonresonant nonlinear material configured to generate anti-Stokes four-wave mixing frequency $2\omega_1 - \omega_2$ and exclude the frequencies $\omega_1$ and $\omega_2$; an optical element operable to direct the portion of the anti-Stokes coherent illumination as the reference beam to illuminate the object at an angle corresponding to less than an entrance angular aperture of the second optical system; and a guided-mode resonance filter disposed between the object and a collection lens of the second optical system to sequentially block and unblock the transmission of the reference beam.

In some aspects, the apparatus can further comprise at least one known reference object to cover a part of an image field.

In some aspects, the first, the second, and the third optical systems are arranged in at least one of a transmission configuration or a reflection configuration.

In some aspects, the plurality of incident wave vectors of the first optical system can comprise wave vectors $< 2\pi/\lambda_1$, wherein the wave vectors are accessed by illumination of the substrate at polar angles between 0 and $\pi/2$.

In some aspects, the plurality of incident wave vectors of the first optical system can comprise wave vectors between $2\pi/\lambda_1$ and $2\pi n_{sub}/\lambda_1$, wherein the wave vectors are accessed by evanescent wave illumination of the object through the substrate of refractive index $n_{sub}$.

In some aspects, the plurality of center wave vectors of the second optical system can comprise only center wave vectors $< 2\pi/\lambda_1$, wherein the center wave vectors are accessed by an optical system above the object plane of the substrate.

In some aspects, the plurality of center wave vectors of the second optical system can comprise center wave vectors between $2\pi/\lambda_1$ and $2\pi n_{sub}/\lambda_1$, wherein the center wave vectors greater than $2\pi/\lambda_1$ are accessed through the plane parallel optical element and the second optical system comprises a plurality of gratings on a side of the plane parallel optical element opposite the object plane, wherein each grating is characterized by a position, a pitch, and a grating profile.

In accordance with some aspects of the present disclosure, a method for coherent anti-Stokes Raman (CARS) microscopy is disclosed. The method can comprise providing an object atop an object plane disposed upon a plane-parallel optical element, wherein the plane parallel optical element is characterized by a homogeneous refractive index ($n_{pp}$) and a surface normal; providing a first optical system disposed to provide an illumination of the object plane, the illumination characterized by two substantially coincident coherent beams with wavelengths $\lambda_1$ and $\lambda_2$ and corresponding angular frequencies $\omega_1$ and $\omega_2$ with $\omega_1 > \omega_2$, a radius of curvature, and disposed at one of a plurality of incident wave vectors from about 0 to about $2\pi n_{pp}/\lambda_1$ with respect to the surface normal of the substrate and at a plurality of azimuth angles spanning 0 to about $2\pi$; providing a second optical system having an optical axis disposed at one of a plurality of center wave vectors from about 0 to about $2\pi n_{pp}/\lambda_1$ with respect to the surface normal, wherein the second optical system is characterized by a numerical aperture and is responsive to optical signals at frequencies greater than $\omega_1$; providing a third optical system disposed between the first optical system and an entrance aperture of a first optical element of the second optical system to provide interferometric reintroduction of a reference illumination as a reference beam at a frequency of $2\omega_1 - \omega_2$, into the second optical system, wherein each of an amplitude, a phase, a radius of curvature and an angle of incidence of the reference is operable to be adjusted such that a corrected reference wave is present at an image plane of the second optical system; recording a sub-image of the object at an object plane using an electronic image device disposed at the image plane of the second optical system that responds linearly to a local optical intensity and transfers a local optical intensity map across the image plane as a sub-image to a signal processor in electronic form, wherein the sub-image is formed as a result of interference between the scattering resulting from the coherent illumination of the object and the reference beam; providing one or more devices operable to adjust the first, the second, and the third optical systems to sequentially collect sub-images for different pairs of the pluralities of illumination wave vectors from the first optical system and collection angles from the second optical system so as to sequentially obtain a plurality of sub-images corresponding to a plurality of regions of spatial frequency space; providing a signal processor device operable to sequentially receive the electronic form of the sub-images and manipulate the sub-images to correct for distortions and alterations introduced by the optical configuration, to store and combine the plurality of sub-images corresponding to the plurality of regions of spatial frequency space into a composite image.

In some aspects, the method can further comprise tuning a frequency difference $\omega_1 - \omega_2$ of the two substantially coplanar and spatially coherent plane waves through Raman resonances of one or more materials in the object.

In some aspects, the plane parallel optical element can be replaced by an air path from the object to the first optical element of the second optical system.

In some aspects, the method can include providing a third optical system further comprising collecting a portion of the coherent illumination using a first beamsplitter disposed in an optical path of the first optical system; and interferometrically reintroducing using one or more optics disposed between the first optical system and an entrance aperture of a first optical element of the second optical system a coherent anti-Stokes $2\omega_1 - \omega_2$ reference beam and excluding the frequencies $\omega_1$ and $\omega_2$ into the second optical system in a position after an exit aperture of a collection lens, wherein the reintroduction is at one of a position corresponding to a position a zero-order beam would have had if it had been transmitted through an appropriate numeric aperture lens of the second optical system or an aliased position to reduce pixel requirements of the electronic image device, wherein the signal processor is adjusted to compensate for this spatial frequency aliasing.

In some aspects, the method can include providing a third optical system further comprising providing a first beamsplitter in an optical path of the first optical system to collect a portion of the coherent illumination; using one or more transfer optics disposed between the first optical system and the second optical system, wherein the optics comprises a nonresonant nonlinear material configured to generate anti-Stokes four-wave mixing frequency $2\omega_1 - \omega_2$ and exclude the frequencies $\omega_1$ and $\omega_2$; and interferometrically injecting an anti-Stokes reference beam using a second beamsplitter disposed between the object and a collection lens of the second optical system at an angle less than an entrance angular aperture of the second optical system.

In some aspects, the method can include providing the third optical system further comprising providing a first beamsplitter in an optical path of the first optical system to collect a portion of the coherent illumination; providing one or more transfer optics disposed between the first optical system and the second optical system, wherein the optics comprises a nonresonant nonlinear material configured to generate anti-Stokes four-wave mixing frequency $2\omega_1 - \omega_2$ and exclude the frequencies $\omega_1$ and $\omega_2$; and using at least one of a grating or a grating on a waveguide disposed between the object and a collection lens of the second optical system to reintroduce the portion of the anti-Stokes coherent illumination as the reference beam into the second optical system at an angle less than an entrance angular aperture of the second collection optical system.

In some aspects, the method can include providing the third optical system further comprising providing a first beamsplitter in an optical path of the first optical system to collect a portion of the coherent illumination; using one or more transfer optics, wherein the optics comprises a nonresonant nonlinear material configured to generate anti-Stokes four-wave mixing frequency $2\omega_1 - \omega_2$ and exclude the frequencies $\omega_1$ and $\omega_2$ to direct the portion of the anti-Stokes coherent illumination as the reference beam to illuminate the object at an angle corresponding to less than an entrance angular aperture of the second optical system; and providing a dynamic physical block disposed in a back pupil plane of the second optical system to alternately block and unblock a portion of a pupil aperture corresponding to a position of the reference beam in the aperture.

In some aspects, the method can include providing the third optical system further comprising providing a first beamsplitter in an optical path of the first optical system to collect a portion of the coherent illumination; providing one or more transfer optics, wherein the optics comprises a nonresonant nonlinear material configured to generate anti-Stokes four-wave mixing frequency $2\omega_1 - \omega_2$ and exclude the frequencies $\omega_1$ and $\omega_2$; directing the portion of the anti-Stokes coherent illumination as the reference beam to illuminate the object at an angle corresponding to less than an entrance angular aperture of the second optical system; and providing a guided-mode resonance filter between the object and a collection lens of the second optical system to sequentially block and unblock transmission of the reference beam.

In some aspects, the method can include providing at least one known reference object to cover a part of an image field.

In some aspects, the first, the second, and the third optical systems can be arranged in at least one of a transmission configuration or a reflection configuration.

In some aspects, the plurality of incident wave vectors of the first optical system can comprise only wave vectors<$2\pi/\lambda_1$, wherein the wave vectors are accessed by illumination of the plane parallel optical element at polar angles between 0 and $\pi/2$.

In some aspects, the plurality of incident wave vectors of the first optical system can comprise wave vectors between $2\pi/\lambda_1$ and $2\pi n_{pp}/\lambda_1$, wherein the wave vectors are accessed by evanescent wave illumination of the object through the plane parallel optical element.

In some aspects, the plurality of center wave vectors of the second optical system can comprise only center wave vectors<$2\pi/\lambda_1$, wherein the center wave vectors are accessed by an optical system above the object plane of the plane parallel optical element.

In some aspects, the plurality of center wave vectors of the second optical system can comprise center wave vectors between $2\pi/\lambda_1$ and $2\pi n_{pp}/\lambda_1$, wherein the center wave vectors greater than $2\pi/\lambda_1$ are accessed through the plane parallel optical element and the second optical system comprises a plurality of gratings on the side of the planar plane parallel optical element opposite the object plane, wherein each grating is characterized by a position, a pitch, and a grating profile.

In some aspects, the method can further comprise one or more processes of subtracting dark field images, subtracting of background images, shifting of spatial frequencies in accordance with an optical configuration, and eliminating one or more overlapping coverage of frequency space.

In some aspects, the method can further comprise selecting regions of spatial frequency space to provide the image of the object in the object plane.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 5A is a schematic illustration showing a dynamic physical block in a back pupil plane of the second optical system to alternately block and unblock the reference beam, according to present teachings.

FIG. 5B is a schematic illustration showing injection of the reference beam into a second optical system using a prism, according to present teachings.

FIG. 5C is a schematic illustration of injection of the reference beam into a second optical system using a beamsplitter, according to present teachings.

FIG. 5D is a schematic illustration showing blocking of the reference beam with a k-vector filter, according to present teachings.

FIG. 5E is a schematic illustration showing injection of the reference beam with a grating, according to present teachings.

FIG. 15A show reconstructed image of 260 nm and 240 nm CD structures obtained using the optical arrangement shown in FIG. 12A.

FIG. 15B show a crosscut (gray) of the images of FIG. 15A compared with a crosscut of corresponding simulation (black).

FIG. 16A shows a reconstructed high frequency image of a 150 nm structure using evanescent illumination and a tilted optical system, shown in FIG. 12B.

FIG. 16B shows a high frequency image simulation of a 150 nm structure using evanescent illumination and a tilted optical system, shown in FIG. 12B.

FIG. 16C shows experimental and simulation cross-cuts of images shown in FIGS. 16A and 16B.

FIG. 16D shows a reconstructed composite image of a 150 nm structure using evanescent illumination and a tilted optical system, shown in FIG. 12B FIG. 16E shows a composite image simulation of a 150 nm structure using evanescent illumination and a tilted optical system, shown in FIG. 12B.

FIG. 16F shows experimental and simulation cross-cuts of images shown in FIGS. 16D and 16E.

FIGS. 24A-24D show an example Illumination and collection configurations, where 24A shows an objective normal to the plane-parallel optical element surface, image frequencies up to $(n_{pp}+NA)/\lambda$ can be captured, 24B shows an objective with tilt off from the optic axis, frequencies up to $(n_{pp}+1)/\lambda$, 24C shows an objective on the side of the plane-parallel optical element with grating, frequencies between $(n_{pp}+1)/\lambda$ and $2n_{pp}/\lambda$, and 24D shows spatial frequency space coverage with regions collected with various geometries indicated.

FIGS. 25A-D shows example arrangements for the plane-parallel optical element of FIG. 24A.

FIG. 33A) t=1 μm, F=16 μm–quality of the resorted image is good, FIG. 33B) t=5 μm, F=16 μm, quality of the resorted image is poor due to increased plane-parallel optical element thickness; FIG. 33C) t=5 μm, F=32 μm, quality of the resorted image is improved as the result of increasing field of view.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

Figure 1:
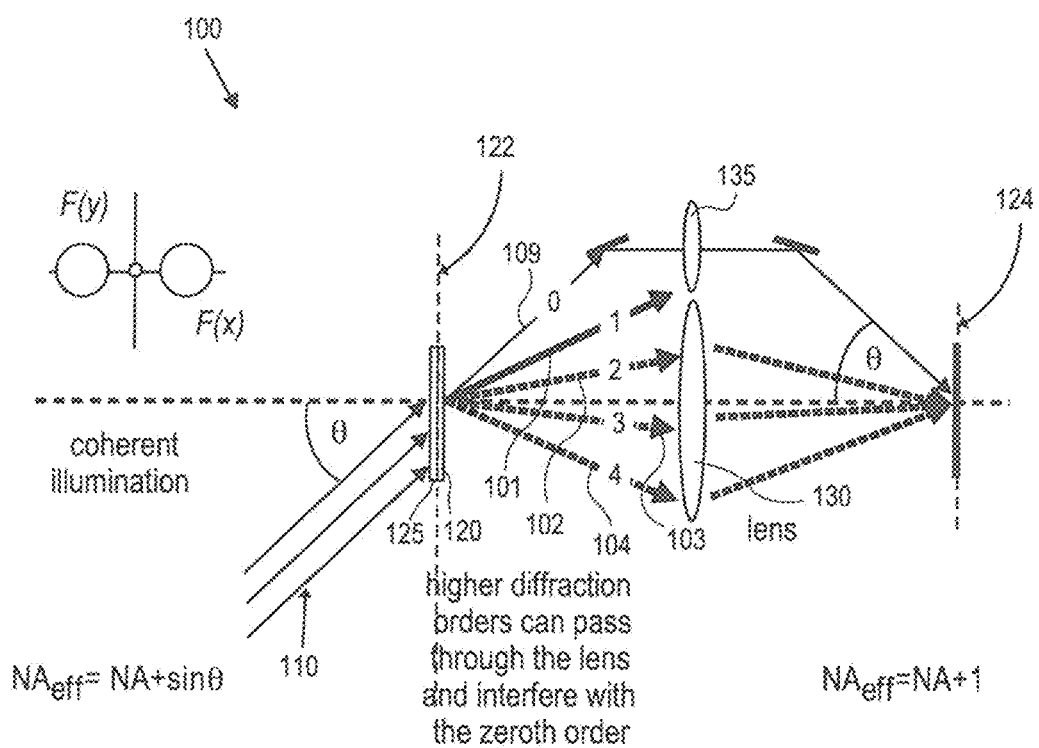
FIG. 1 shows an exemplary prior art imaging interferometric microscopy (IIM) experimental arrangement.
Figure 2A:
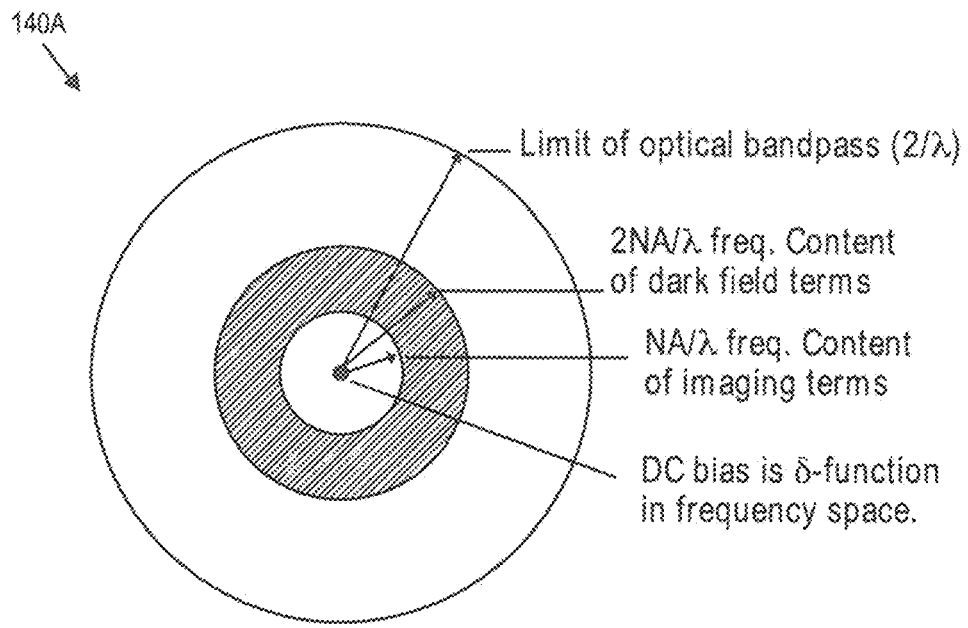
FIG. 2A shows the frequency space coverage for conventional normal incidence coherent illumination.
Figure 2B:
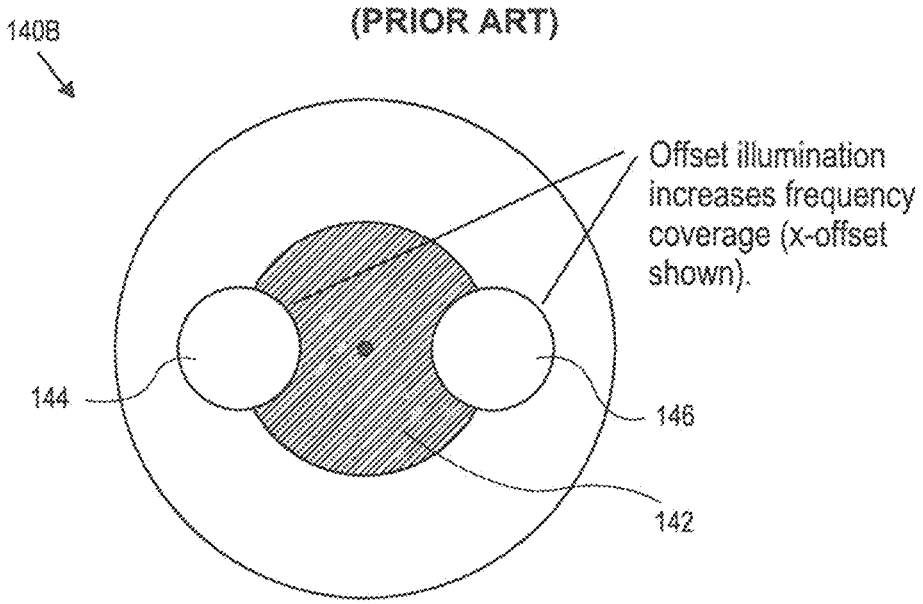
FIG. 2B shows the frequency space coverage for an off-axis incidence coherent illumination.

FIG. 1 shows a prior art imaging interferometric microscopy (IIM) arrangement 100. As shown in FIG. 1, a collimated (equivalent to coherent) illumination beam 110 is incident on an object 120 at an angle of incidence θ. In the illustrated case, θ is beyond the collection angle of the objective lens 130 and an auxiliary optical system 135 is shown schematically to collect the zero-order transmission 109, appropriately adjust its divergence, direction, and phase and re-inject it onto the image plane 124 where it interferes with the diffracted beams 101, 102, 103, 104 from the object 120 to construct a partial image. Alternatively, instead of using the zero-order transmission 109, which might be blocked by the objective-lens 130 mount, a portion of the illumination beam 110 can be split off before the object 120 and directed around the objective lens 130. The interference between the zero-order beam 109 and the diffracted beams 101, 102, 103, 104 transmitted through the objective lens 130 can shift the collected diffracted information back to high frequency. As a result of the square-law intensity response, the resulting frequency coverage 140B can be represented by a pair of circles 144, 146 of radius NA/λ, shifted away from zero frequency 142 by $2(2\pi)NA/\lambda$ as shown in FIG. 2B. FIG. 2B shows the frequency space coverage 140B for off-axis coherent illumination, where frequencies beyond the lens bandpass are recorded in the sub-image as a result of the interferometric reconstruction. For comparison, FIG. 2A shows the frequency space coverage 140A for conventional normal incidence on-axis coherent illumination.

An object of the present teachings is to reduce or eliminate the requirement of the prior art for optical access to between the back of the objective lens and the image plane of the second optical system. This access is required for injecting the reference beam 109 in the prior art (FIG. 1). However, in many existing optical microscopes, this region is inaccessible. The structured illumination approach disclosed herein provides alternative methods of injecting the reference beam in front of the objective lens of the second optical system, thereby simplifying the application of imaging interferometric microscopy to existing optical microscopy systems. Since both the diffracted beams and the reference beams are not transmitted through the same objective, characterized by an NA, the high frequency image components are necessarily shifted to lower frequency. This is similar to the use of an intermediate frequency in heterodyne radio receivers, but in the spatial frequency rather than the temporal frequency domain. It is necessary to reset the spatial frequencies by signal processing after each sub-image is captured in the electronic recording device. Additional advantages of this approach are that the pixel count requirements in the image plane are reduced, since only lower spatial frequencies, up to $2(2\pi)NA/\lambda$, are recorded, and the interferometer can be made smaller since all of the components are on the front side of the objective lens, reducing vibrational effects on the interferometric reconstruction.

Figure 3:
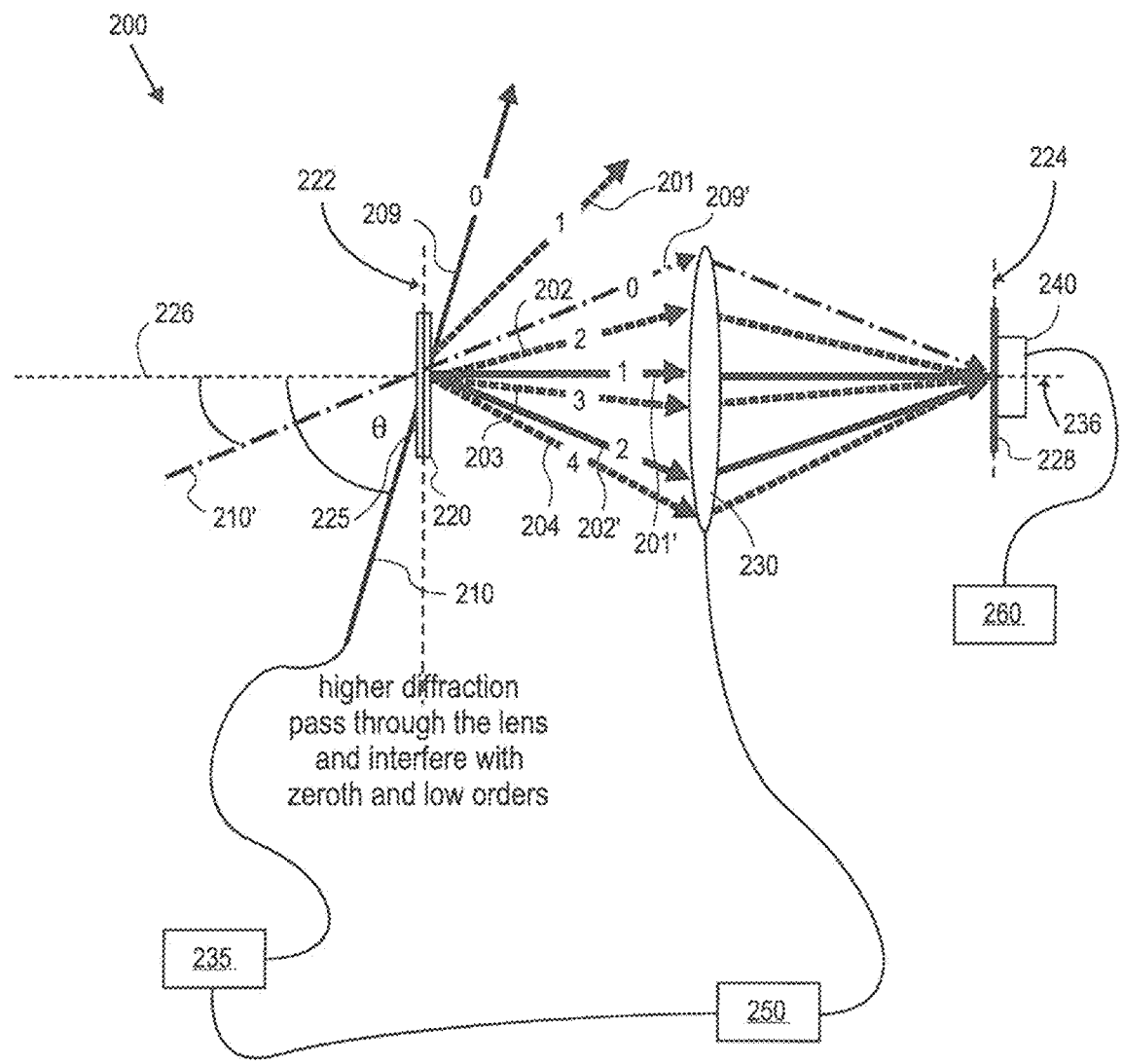
FIG. 3 shows an exemplary structured illumination approach to IIM, according to various embodiments of the present teachings.

FIG. 3 shows an optical arrangement of the apparatus 200 for an exemplary structured illumination approach to IIM, according to various embodiments of the present teachings. The apparatus 200 can include an object 220 disposed on an object plane 222 on which a first surface of a substrate 225 can be disposed, wherein the substrate 225 can be characterized by a homogeneous refractive index ($n_{sub}$) and a surface normal 226. The apparatus 200 can also include a first optical system including a source 211 and one or more optical components (not shown) disposed to provide a substantially coherent illumination 210 of the object plane 222, the illumination 210 characterized by a wavelength λ and a radius of curvature and disposed at one of a plurality of incident wave vectors from about 0 to about $2\pi/\lambda$ with respect to a surface normal of the substrate and at a plurality of azimuth angles spanning 0 to $2\pi$. Illumination 210 is diffracted by object 221 into a central, undiffracted $0^{th}$ order 209 and higher diffraction contributions which come from either higher orders of diffraction from a specific feature of the object or from additional spatial features of the object. Generally, smaller features give rise to larger diffraction angles. For convenience of notation, these are collectively referred to as diffraction orders, including a $1^{st}$ order 201, a $2^{nd}$ order 202, a $3^{rd}$ order 203 and a $4^{th}$ order 204. The apparatus 200 can also include a second optical system 230 disposed to collect portions of the illumination beam scattered from the object plane 222, the second optical system having an optical axis 236 disposed at one of a plurality of center wave vectors from about 0 to about $2\pi/\lambda$ with respect to the substrate surface normal 226 and at the azimuth angle corresponding to the illumination of the first optical system, wherein the second optical system 230 is characterized by a numerical aperture (NA). In various embodiments, the second optical system 230 can include at least one objective lens. The apparatus 200 can also include a third optical system represented by beamsplitter 205 and mirror 206 disposed between the optical path of the first optical system and an entrance aperture of the second optical system to provide interferometric reintroduction of a portion of the coherent illumination (reference beam) 210' into the second optical system 230, wherein each of an amplitude, a phase, a radius of curvature, a path length and an angle of incidence of the reference beam can be adjusted such that a correct reference beam can be present at a image plane 224 of the second optical system 230. It is understood that additional optical components not shown are necessary to achieve this correct reference beam. The reference beam 210' is obtained by splitting off a portion of the illumination beam 210 with beamsplitter 205 and redirecting the split-off beam with optical system 206 and the apparatus 200 is configured so that the total path lengths of the illumination beam 210 and the reference beam 210' from the beam splitter to the image plane 224 are within the temporal coherence length of the source to insure interferometric reconstruction of the sub-image. Illumination 210' is diffracted by substrate 225 into a central, undiffracted $0^{th}$ order 209' and higher diffraction orders including a $1^{st}$ order 201' and a $2^{nd}$ order 202'. The apparatus can also include an electronic image device 228 disposed at the image plane 224 of the second optical system 230 that responds linearly to the local optical intensity and transfers the local optical intensity map across the image plane (a sub-image) to a signal processor device 260 in electronic form. In various embodiments, the electronic image device 228 can be a charged coupled device (CCD) camera, a CMOS (complementary metal-oxide semiconductor) camera, and any similar electronic focal plane array device. The apparatus 200 can further include a device 250 for adjusting the first, the second, and the third optical systems to collect sub-images for different pairs of the pluralities of incident (first optical system) and collection center (second optical system) wave vectors so as to sequentially obtain a plurality of sub-images corresponding to a plurality of regions of spatial frequency space. In various embodiments, the device can block/unblock various beams, rotate substrate etc. In some embodiments, the device can include mechanical components, such as, for example, motors. In other embodiments, the device can include electronic components, such as, for example, acoustic modulators or similar devices. The signal processor device 260 can also be arranged to sequentially receive the electronic form of the sub-images and manipulate the sub-images to correct for distortions and alterations introduced by the optical configuration, store, and combine the plurality of sub-images corresponding to the plurality of regions of spatial frequency space to create a composite image. In some other embodiments, the signal processor device can include one or more computers. In some embodiments, the first, the second, and the third optical systems can be arranged in a transmission configuration with respect to the substrate surface. In other embodiments, the first, the second, and the third optical systems can be arranged in a reflection configuration with respect to the substrate surface. Items 250, 235 and 270 represent means to alter the various optical systems to correspond to different angles of incidence and scattering as described below.

In certain embodiments apparatus 200 for an exemplary structured illumination approach to IIM can also include at least one known reference object to cover a small part of the image field.

According to various embodiments, there is a method for structural imaging interferometric microscopy. The method can include providing an object 220 disposed over a planar substrate 225, wherein the substrate 225 is characterized by a homogeneous refractive index ($n_{sub}$) and a surface normal 226 and providing a first optical system to illuminate the object 220 with substantially coherent illumination 210, the illumination characterized by a wavelength λ and a radius of curvature and disposed at one of a plurality of incident wave vectors from about 0 to about $2\pi/\lambda$ with respect to a surface normal of the substrate and at a multiplicity of azimuth angles spanning from about 0 to about $2\pi$. The method can also include providing a second optical system 230 disposed to collect portions of the illumination scattered from the object plane 222, the second optical system 230 having an optical axis 236 disposed at one of a plurality of center wave vectors from about 0 to about $2\pi/\lambda$ with respect to the substrate 225 surface normal 226 and at the azimuth angle corresponding to the illumination of the first optical system, wherein the second optical system 230 is disposed such that the object 220 is substantially at the object plane 222 of the second optical system 230 which is characterized by a numerical aperture (NA). The method can further include providing a third optical system disposed between the optical path of the first optical system and an entrance aperture of the second optical system to provide interferometric reintroduction of a portion of the coherent illumination (reference beam) 210' into the second optical system, wherein each of an amplitude, a phase, a radius of curvature and an angle of incidence of the reference can be adjusted such that a corrected reference wave is present at the image plane of the second optical system, wherein the corrected reference beam 210' and the illumination beam 210 are within the temporal coherence length of the source. The method can also include recording a sub-image of the object 220 at an object plane 222 using an electronic image device 228, wherein the sub-image is formed as a result of interference between the scattering resulting from the coherent illumination of the object 220 and the reference beam 210'. The method can also include adjusting the first, the second, and the third optical systems to sequentially collect a plurality of sub-images corresponding to a plurality of regions of spatial frequency space, manipulating each of the plurality of sub-images using a signal processor to correct for distortions and alterations introduced by the optical configuration, and combining the plurality of sub-images into a composite image to provide a substantially faithful image of the object 220. In various embodiments, the method can further include one or more processes of subtraction of dark field images, subtraction of background images, shifting of spatial frequencies in accordance with the optical configuration, and elimination of one or more overlapping coverages of the frequency space wherein the elimination operations can be performed either in the optical systems or in the signal processing. In some embodiments, the method can also include selecting the regions of spatial frequency space to provide a more or less faithful image of the object 220 in the object plane 222. One of ordinary skill in the art would know that the regions of frequency space that are important vary depending on the object. For example for a Manhattan geometry pattern, there is less need to gather spectral information on the diagonals. See, for example, Neumann et al. in Optics Express, Vol. 16, No. 10, 2008 pp 6785-6793 which describes a structural illumination for the extension of imaging interferometric microscopy, the disclosure of which is incorporated by reference herein in its entirety.

Figure 4:
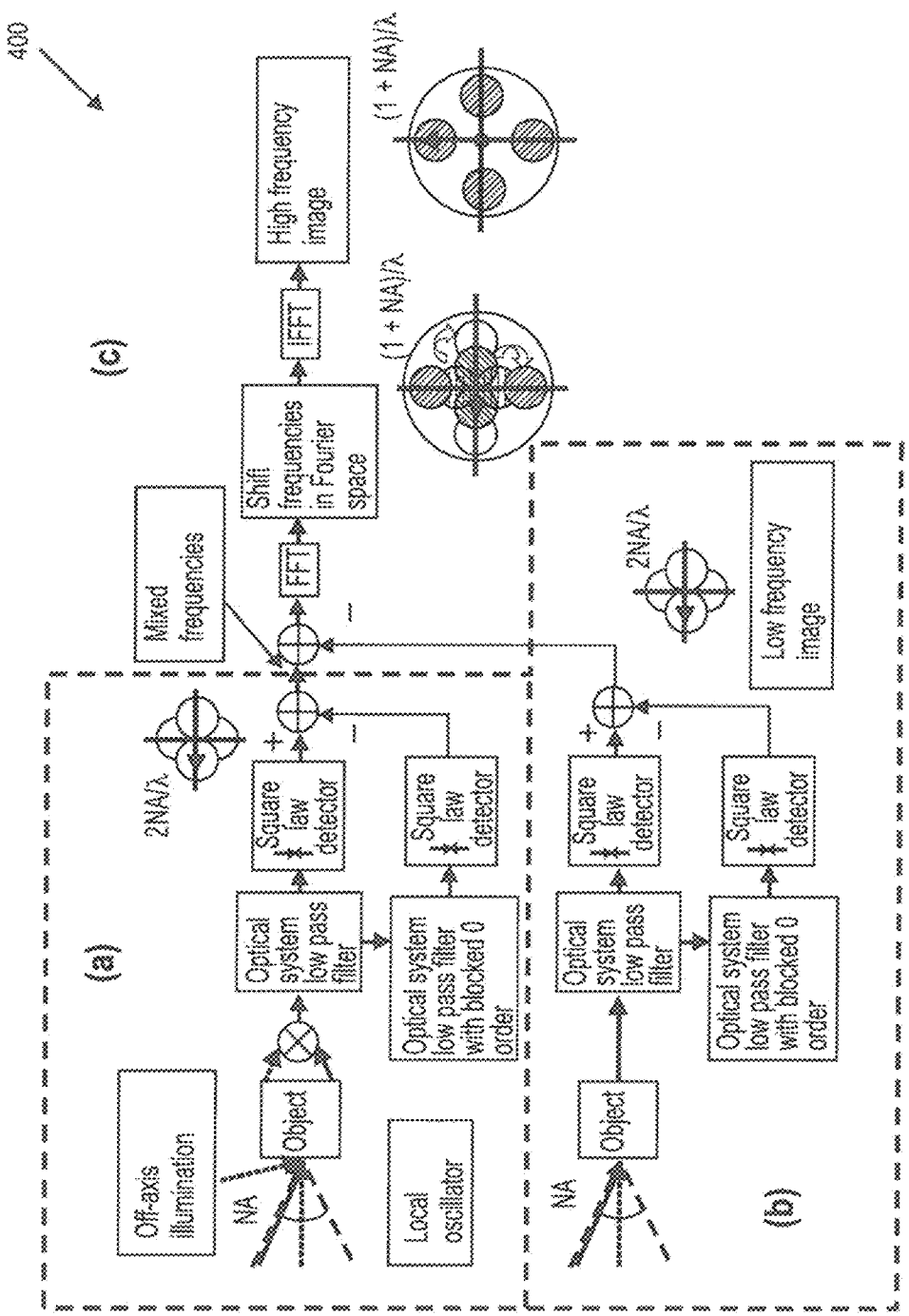
FIG. 4 shows the schematic of structural illumination and restoration algorithms, in accordance with the present teachings.

FIG. 4 shows a flow diagram schematic, indicated generally by 400(a), (b) and (c), of structural illumination and restoration algorithms. High spatial frequencies represented by diffracted beams from the off-axis illumination are mixed with the local oscillator beam, the dark field of the image is subtracted as is the low frequency image without its dark field. Then the spatial frequencies are reset in Fourier space and the whole image is reconstructed by combining high and low frequency sub-images.

To mathematically explain the structured illumination approach to IIM, first a simple mathematical description of a conventional coherent illumination microscopy image will be described and then the mathematical description will be extended to the prior art IIM experiment and finally to the structured illumination approach.

The total transmission through an arbitrary object (assumed to be periodic on large scale to allow Fourier sums rather than Fourier integrals) and illuminated by a plane wave at normal incidence can be given by:

$$\sum_{\forall k,l \in R} A_{k,l} \exp[ixk\omega_x + iyl\omega_y]e^{i\gamma_{k,l}z} = \quad (1)$$

$$A_{0,0}e^{i\gamma_{0,0}z} + \sum_{k,l \neq 0} A_{k,l} \exp[ixk\omega_x + iyl\omega_y]e^{i\gamma_{k,l}z}$$

where $\omega_x$, $\omega_y$ are the discrete spatial frequency increments of the Fourier summation; x and y are orthogonal spatial coordinates;

$$\gamma_{k,l} \equiv \sqrt{\left(\frac{2\pi n}{\lambda}\right)^2 - (k\omega_x)^2 - (l\omega_y)^2}$$

with n the refractive index of the transmission medium (1 for air); R is the set of integers, for which $(|\gamma_{k,l}|)^2 > 0$, that is the range of integers for which the diffracted beams are within the bandpass of the transmission medium and are propagating in the z-direction, away from the object. Note that this representation is a scalar approximation that is appropriate as long as the angles do not get too large, and it is assumed below that all beams are polarized in the same direction. A more rigorous treatment is straightforward, but mathematically gets more complex and obscures the physical insight in these simpler equations.

The transmission through the optical system adds a filter factor:

$$T(0;0)A_{0,0}e^{i\gamma_{0,0}z} + \sum_{k,l \neq 0} T(k\omega_x; l\omega_y)A_{n,l}\exp[ix(k\omega_x) + il\omega_y y]e^{i\gamma_{k,l}z} \quad (2)$$

The transmission function of the objective lens is a simple bandpass function:

$$T(\omega_X; \omega_Y) = 1 \text{ for } \sqrt{\omega_X^2 + \omega_Y^2} \leq \omega_{MAX} = \frac{2\pi NA}{\lambda} \quad (3)$$
$$= 0 \text{ else,}$$

and the final image intensity can be obtained by taking the square modulus of equation 2, viz:

$$I(x, y, z) = [T(0,0)]^2 |A_{0,0}|^2 + \quad (4)$$
$$\sum_{k,l} T(0,0)T(k\omega_x, l\omega_y)A_{0,0}A_{k,l}^* \exp[-i(k\omega_x x + l\omega_y y)]e^{i(\gamma_{0,0} - \gamma_{k,l})z} +$$
$$c.c. + \sum_{k,l} \sum_{k',l'} T(k\omega_x, l\omega_y)T(k'\omega_x, l'\omega_y)A_{k,l}A_{k',l'}^* \exp$$
$$\{i[(k-k')\omega_x x + (l-l')\omega_y y]\}e^{i(\gamma_{k,l} - \gamma_{k',l'})z} + c.c$$

Each of the three lines in this result has a simple physical interpretation. The top line is a constant independent of spatial coordinates, equal to the average intensity of the pattern. This ensures that the intensity is always positive as physically required. The second line represents the imaging terms that are retained. Finally the third line is the cross-correlation of the diffracted beams with themselves equivalent to the dark field image that would be obtained if the zero-order diffraction (transmission) was blocked at the back pupil plane. The imaging terms are band-limited to transverse spatial frequencies of $(2\pi/\lambda)NA$; the dark field terms extend out to $(4\pi/\lambda)NA$ and are typically weaker in intensity than the imaging terms since for an object with thickness<<$\lambda$, $|A_{0,0}|$ is larger than any of the diffracted terms. In all of the summations the summation indices extend over all terms in R except for the zero-order term which has been explicitly separated out. Equation 4 gives the intensity over all space beyond the objective lens. The image is obtained in the back image plane (z=0) where the exponentials in $\gamma z$ vanish. The focusing information is contained in these exponential terms and its characteristic length, the depth-of-field, depends on the NA, as is well known. A Fourier optics perspective provides additional insight into the three terms. The DC term (top line) is a $\delta$-function at the origin. The image terms fill a circle of radius $2\pi NA/\lambda$ as a result of the band-limited transmission function. Finally, the dark-field image contains frequencies up to $4\pi NA/\lambda$ as a result of the interference of the various diffracted orders.

It is well-known that additional, higher spatial frequency, information can be accessed with off-axis illumination. FIG. 1 shows a conventional IIM arrangement 100, wherein a collimated illumination beam 110 can be incident on an object 120 at an angle of incidence θ. In particular in the case of IIM, the offset angle is chosen such that the zero-order transmission (reflection) is beyond the lens (130) NA, $$\omega_{offset} > \frac{2\pi NA}{\lambda}.$$

The result is that higher spatial frequency information is transmitted through the lens, but only a dark field image is recorded in a traditional coherent illumination microscopy configuration (without the reference beam 109). This is solved in IIM by introducing an auxiliary optical system 135, an interferometer that reinjects the zero-order transmission on the low-NA side of the lens to reset the spatial frequencies. In practice it is simpler to reintroduce the zero-order transmission as an appropriately mode matched point source in the back pupil plane without actually using the transmitted beam which is often blocked by the objective lens mount. Effectively, the interferometer results in a modified filter transfer function where the zero-order is transmitted even though it is outside the lens NA. The amplitude, the phase, and the offset position in the back focal plane of the objective have to be controlled to provide a correct sub-image. These are often set by using a nearby, known reference object along with the object of interest.

It is straightforward to extend the mathematical treatment to the off-axis illumination case. Equation 2 can be modified to:

$$A'_{0,0}e^{-i\omega_{off}x}e^{i(\gamma'_{0,0})z} + \quad (5)$$
$$\sum_{k,l \neq 0} T(k\omega_x - \omega_{off}; l\omega_y)A_{n,l}\exp[ix(k\omega_x - \omega_{off}) + il\omega_y y]e^{i\gamma'_{k,l}z}$$

where $\omega_{off} = 2\pi \sin(\theta_{off})/\lambda$ is the frequency offset arising from the off-axis illumination at angle $\theta_{off}$ (assumed in the x-direction), the primes on the $\gamma$s indicate that the propagation directions take into account the offset illumination, and the prime on the $A_{0,0}$ refers to the re-injected 0-order.

Taking the square of equation 5 can provide the intensity on the imaging camera:

$$|A'_{0,0}|^2 + \ldots (dc \text{ offset}) \quad (6)$$
$$\sum_{k,l \neq 0} A'_{0,0}A_{k,l}^* T(k\omega_x - \omega_{off}; l\omega_y)\exp[ik\omega_x x + il\omega_y y]e^{i(\gamma'_{0,0} - \gamma_{k,l})z} +$$

-continued $$\sum_{k,l\neq 0',}\sum_{k',l'\neq 0} A_{k,l}T(k\omega_x - \omega_{off}; l\omega_y)A^*_{n',l'}T(k'\omega_x - \omega_{off}; l'\omega_y)$$

$$\exp[i(k-k')\omega_x x + i(l-l')\omega_y y]e^{i\left(\gamma^{off}_{k,l} - \gamma^{off}_{k',l'}\right)z}\ldots \text{ (dark field)}$$

where the three terms on separate lines correspond to (top) a constant term, (middle) the imaging terms and (bottom) the dark field image. Subtracting out the dark field terms (by taking an image with the interferometer blocked so that only the third term survives) provides a sub-image that accurately captures the spatial frequency components that are transmitted through the optical system. Note that the imaging terms (middle line) are at the correct frequencies and that the offset illumination angle has cancelled out of the expression except for the filter transmission functions.

Changing both the illumination angle (and the angle of reintroduction) and the azimuthal angle changes the offset allowing recording of a different region of frequency space. Specifically, for Manhattan geometry (x,y oriented patterns) a second offset exposure to capture the high spatial frequencies in the y-direction, that is with the substrate rotated by $\pi/2$, can be used. Additional spatial frequency terms can be captured with large illumination angles.

Referring back to the FIG. 3, in the exemplary structured illumination approach to IIM, there can be two coherent illumination beams 210, 210', the first beam 210 can be at the same offset as in the previous example so that $\omega_{offset}$ is $> NA/\lambda$, and the second beam 210' can be at the maximum offset that fits through the lens $\omega_{off} \ddagger NA/\lambda$, denoted as $\omega_{NA}$ in the equation. Then the fields are:

$$A_{0,0}\exp(-i\omega_{off}x)e^{i\gamma^{off}_{0,0}z} + \sum_{k,l\neq 0} A_{k,l}\exp[i(k\omega_x-\omega_{off})x + il\omega_y y]e^{i\gamma^{off}_{k,l}z} + \quad (7)$$

$$B_{0,0}\exp(-i\omega_{NA}x)e^{i\gamma^{NA}_{0,0}z} + \sum_{p,r\neq 0} B_{p,r}\exp[i(p\omega_x-\omega_{NA})x + ir\omega_y y]e^{i\gamma^{NA}_{p,r}z}$$

where the series with coefficients $A_{k,j}$ are due to the first offset beam (210) and the second series with the coefficients $B_{p,q}$ are due to the second offset beam (210') and squaring while taking advantage of the fact that without the interferometer the $A_{0,0}$ beam 209 is not transmitted to the objective image plane while the $B_{0,0}$ beam 209' is transmitted through the lens 230 gives:

$$\begin{cases} |B_{0,0}|^2 + \sum_{p,r\neq 0} B_{0,0}B^*_{p,r}T(p\omega_x-\omega_{NA}; r\omega_y)\exp[i(p\omega_x x + r\omega_y y)] \\ e^{i(\gamma^{NA}_{0,0}-\gamma^{NA}_{p,r})z} + c.c. + \sum_{p,r\neq 0}\sum_{p',r'\neq 0} B_{p,r}B^*_{p',r'}T(p\omega_x-\omega_{NA}; r\omega_y)T \\ (p'\omega_x-\omega_{NA}; r'\omega_y)\exp[i(p-p')x + i(r-r')y]e^{i(\gamma^{NA}_{p,r}-\gamma^{NA}_{p',r'})z} \end{cases} + \quad (8)$$

$$\left\{\sum_{k,l} B_{0,0}A^*_{k,l}T(l\omega_x-\omega_{off}; n\omega_y)\right.$$

$$\left.\exp[-i(k\omega_x-\omega_{off}+\omega_{NA})x - ik\omega_y y]e^{i(\gamma^{NA}_{0,0}-\gamma^{off}_{k,l})z} + c.c.\right\} +$$

$$\sum_{k,l}\sum_{k',l''} A_{k,l}A^*_{k',l'}T(k\omega_x-\omega_{off}; l\omega_y)T(k'\omega_x-\omega_{off}; l'\omega_y)$$

$$\exp[i(k-k')\omega_x x + i(l-l')\omega_y y]e^{i\left(\gamma^{off}_{k,l}-\gamma^{off}_{k',l'}\right)z} + c.c.$$

$$\sum_{k,l}\sum_{p,r\neq 0} A_{k,l}B^*_{p,r}T(k\omega_x-\omega_{off}; l\omega_y)T(p\omega_x-\omega_{NA}; r\omega_y)\times$$

$$\exp[i(k-p)\omega_x + i(\omega_{NA}-\omega_{off})x + i(l-r)\omega_y]$$

$$e^{i\left(\gamma^{off}_{k,l}-\gamma^{NA}_{p,r}\right)z} + c.c.$$

The first three terms in the upper bracket, labeled [I], in equation 8 are the result of the off-axis illumination at the edge of the pupil. This image can be measured independently by blocking the extreme off axis beam and subtracted from the result. The term labeled [II] is the desired information, the image terms beating against a zero-order beam; because the zero-order beam is not at the correct angle to reset the frequencies to match the object frequencies (adjusted for magnification) there is a shift between the observed and the actual image plane frequencies $\{\exp[i(\omega_{NA}-\omega_{off})x]\}$ that will need to be fixed computationally (e.g. one is measuring the Fourier components at an intermediate frequency as detailed above). [III] is the dark field from the extreme off-axis illumination. Finally the last term, [IV] is the cross-correlated dark field from the two illumination beams.

To remove the unwanted terms in equation 8, five strategies can be used. However, these are not intended to be all-inclusive and other possibilities may exist. These are illustrated schematically in FIGS. 5A-5E. There are two general approaches, in the FIGS. 5A-5C, the reference beam is added before the object plane. This adds to some additional complexity in that the off axis and the reference beams give rise to diffracted information and it is necessary to separate out the information corresponding to the diffraction from the reference beam from the off axis beam. This can be accomplished as shown in the scheme outlined in FIG. 4. In FIGS. 5D and 5E, the reference beam is added after the object plane and before the entrance to the collection lens. In these configurations, the reference beam does not illuminate the object and hence there is no additional diffraction. This simplifies the analysis, but at the cost of adding additional optical components in the region of limited access.

FIG. 5A shows the first embodiment, wherein the third optical system 500A can further include a first beamsplitter disposed in the optical path of the first optical system to collect a portion of the coherent illumination, one or more optical components to direct the portion of the coherent illumination as a reference beam 510' to illuminate the object 520 at an angle $\theta$ corresponding to less than the entrance angular aperture ($<\sim\sin^{-1}$ NA) of the second optical system 530, and a dynamic (adjustable on/off) physical block 550 disposed in a back pupil plane of the second optical system 530 to alternately block and unblock a small portion of the pupil aperture corresponding to the position of the reference beam 510 in the aperture. One of the advantages of this embodiment is that all of the information can be retained. However, this embodiment requires access to the illumination system pupil. In the case shown in FIG. 5A, the objective pupil has been relayed to an auxiliary plane where it might be easier to access. The details of this optical configuration will depend on the optical construction of the objective lens.

FIG. 5B shows the second embodiment 500B, wherein both illumination beams can be shifted slightly using a prism 560 so that the zero order 209' can be blocked but there is no change in the exponential factor, only in the transmission factors. Using the first and second embodiments, one can obtain and subtract dark field optical intensities from the image formed by interference of low and high frequencies (the second, fourth, and fifth terms of equation 6). Then one can subtract low frequency image without dark field and restore high frequency image by shifting frequencies in Fourier space. The second embodiment can be implemented easily and does not require any access to the objective pupil plane but it has some image-dependent information loss associate with the shifting of the illumination angles. As shown in FIG. 5B, the prism is located in between the object 520 and the entrance aperture of the objective lens 530; alternatively it can be located before the object 520. Depending on the specifics of the object 520, it may be advantageous to dither the position of only the reference zero-order beam or of both zero-order beams.

Figure 6:
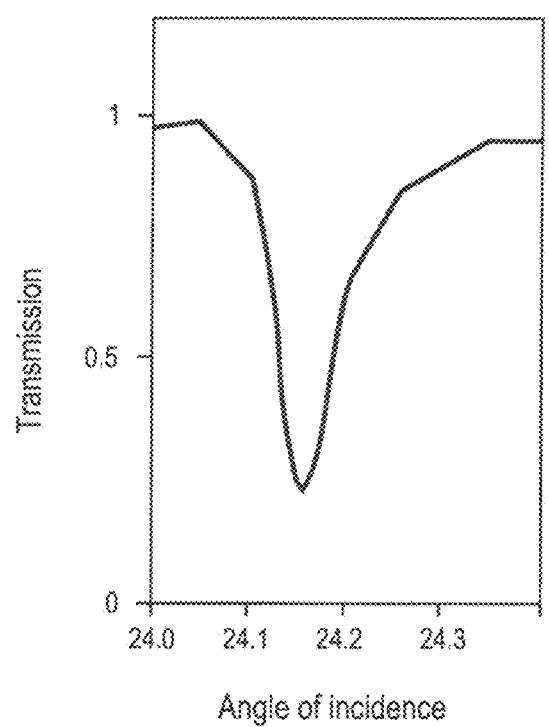
FIG. 6 shows k-vector filter characteristic of an exemplary SiN-on-glass guided mode resonance filter.

FIG. 5C shows yet another embodiment using a guided-mode filter (k-vector filter) 582 to block the zero order transmission just before the objective 530 and transmit the diffracted information at all other angles. FIG. 6 shows an exemplary experimental un-optimized k-vector filter characteristic of a silicon-nitride-on-glass guided mode resonance filter, with a narrow angular width of the coupling. U.S. Pat. No. 5,216,680 discloses guided mode filter which can be used as an optical filter with very narrow line width and as an efficient optical switch, the disclosure of which is incorporated by reference herein in its entirety. Referring back to FIG. 5C, it is possible to switch the zero-order on and off by mechanical dithering of the angular position or by dithering by a small degree of rotation around the optical axis, shown generally by 590. This will allow identification of the source of the diffracted waves in the sub-image. Accordingly, the exemplary third optical system 500C of the apparatus 200 in accordance with various embodiments, can further include one or more optical components to direct the portion of the coherent illumination as a reference beam to illuminate the object 520 at an angle θ less than the entrance angular aperture ($<\sim\sin^{-1}$ NA) of said second collection optical system 530, the guided-mode resonance filter (k-vector filter) 582 disposed between the object plane 522 and a collection lens of the second optical system 530, and another device 527 to adjust the position, tilt and rotation of the guided-mode resonance filter 582 between positions, tilts and rotations in which it alternately transmits and blocks the portion of the reference beam transmitted through the object plane.

FIG. 5D shows yet another exemplary third optical system 500D of the apparatus 200 in accordance with various embodiments. The third optical system 500D can further include a first beamsplitter disposed in the optical path of the first optical system to collect a portion of the coherent illumination, one or more transfer optics disposed between the first optical system and the second optical system, and at least one of a grating 584 or a grating on a waveguide disposed between the object plane 522 and a front aperture of the collection lens (objective) of the second optical system 530 to reintroduce the portion of the coherent illumination as a reference beam into the second optical system 530 at an angle θ less than the entrance angular aperture ($<\sim\sin^{-1}$ NA) of the second optical system. In various embodiments, the grating 584 can have a short pitch (high spatial frequency) to avoid diffraction of the waves incident onto the grating 584 into new directions that are captured by the objective lens of the second optical system 530. A major advantage of this method is that it does not require switchable gratings or mechanical actuation of the filter, since modulation is by simple blocking of the incident beam.

FIG. 5E shows the fifth embodiment, wherein the zero order 510' can be re-injected after the object and just in front of the objective by a beamsplitter 570. Accordingly, the third optical system can include a second beamsplitter 570 disposed between the object plane 522 and a front aperture of a collection lens (objective) of the second optical system 530 to reintroduce the portion of the coherent illumination as a reference beam 510' into the second optical system 530 at an angle θ less than the entrance angular aperture ($<\sim\sin^{-1}$ NA) of the second optical system 530. The beamsplitter 570 can eliminate all of the diffracted beams associated with the local oscillator, $B_{p,r}=0$, $\forall p$, $r \neq 0$, and simplifies equation 8. The third embodiment does not contain the first, second and fifth terms at all, so it is the most robust for the image processing, but images can be distorted by aberration caused by the beamsplitter; this aberration can be corrected with additional optical components. Using a very thin beamsplitter, e.g., a pellicle, eliminates much of the aberration associated with an expanding beam passing through a tilted thin plate. The use of a beamsplitter impacts the working distance of the objective, but the depth-of-field and field-of-view advantages of IIM are retained.

Figure 7A:
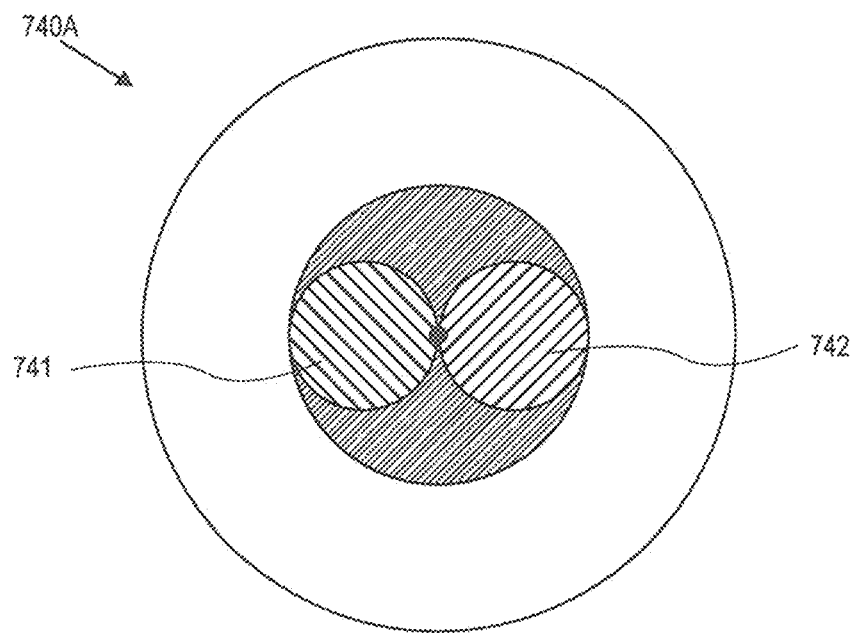
FIG. 7A shows the frequency space coverage for the arrangement of FIG. 3, with intermediate frequency offset within bandpass of lens.
Figure 7B:
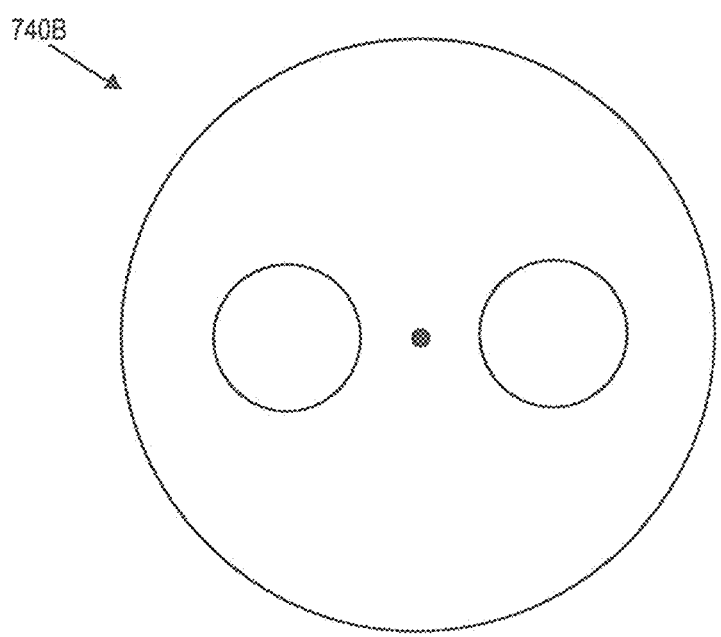
FIG. 7B shows the frequency space coverage for the arrangement of FIG. 3 after removal of the dark field and intermediate frequency imaging terms and correction of the observed frequencies.

FIGS. 7A and 7B show the frequency space coverage for the structured illumination approach to IIM shown in FIG. 3 and using the first embodiment as shown in FIG. 5A. All of the recorded frequencies are within the bandpass of the objective lens. The two offset circles 741, 742 in FIG. 7A correspond to coverage 740A of both the intermediate frequency imaging terms and the offset frequency imaging terms beating with the intermediate frequency local oscillator. FIG. 7B shows the coverage 740B after the unwanted dark field and local oscillator self-imaging terms have been removed and the spatial frequencies have been reset to their correct values.

Figure 8B:
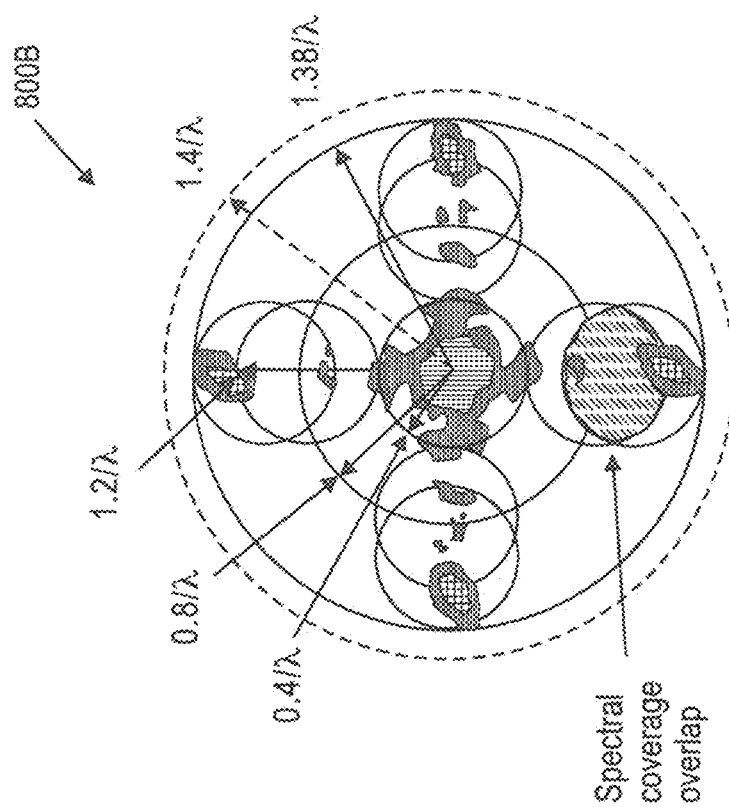
FIG. 8B illustrates intensity Fourier space components of the Manhattan geometry pattern shown in FIG. 8A, mapped onto a frequency space coverage of the imaging system.
Figure 8A:
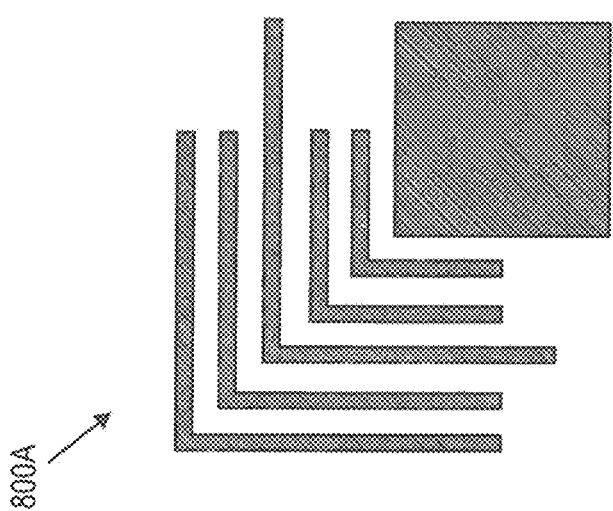
FIG. 8A schematically illustrates a Manhattan geometry pattern used for image resolution exploration consisting of five nested "ells" and a large box.

FIGS. 8A and 8B illustrate the frequency space coverage of partial images. FIG. 8A shows an illustration of a Manhattan (x, y) geometry pattern 800A used for image resolution exploration consisting of five nested "ells" and a large box. The lines and spaces of the "ells" are about 240 nm. FIG. 8B, indicated generally at 800B, shows the intensity Fourier space components of the pattern 800A, mapped onto the frequency space coverage of the imaging system using a NA=0.4 objective and an illumination wavelength of 633 nm (HeNe laser source). The resolution limit of this microscope system with conventional illumination is $\sim 0.6\lambda/NA$ ($\sim 950$ nm). The two circles at radii of NA/$\lambda$ (0.4/$\lambda$) and 2NA/$\lambda$ (0.8/$\lambda$) correspond to the approximate frequency space limits for coherent and incoherent illumination, respectively, and reflect the low-pass transmission characteristic of the objective lens. The inner sets of small shifted circles (radius NA/$\lambda$) in FIG. 8B, that extend from −3NA/$\lambda$ to 3NA/$\lambda$ (±1.2/$\lambda$) in the x- and y-directions, show the frequency space coverage added with two offset partial images, one in each direction. The imaging is single side-band, only the diffracted plane waves to one side of the object are collected (opposite to the tilt of the illumination beam), the square law (intensity) response of the image formation and detection process restores the conjugate frequency space components, resulting in the two symmetrically displaced circles in FIG. 8B for each partial image. The offset (off-axis tilt) for these images was chosen at 2(2π) NA/$\lambda$ to ensure that there was no overlap between the spectral coverage of the low-frequency partial image (extending out to NA/$\lambda$) and the offset images. As discussed previously, improved images can be obtained by subtracting the dark-field components of the image (with the zero-order transmission blocked). In the present embodiments, this provided a cosmetic, not a dramatic, improvement to the images. Additional frequency space coverage is available with a second pair of off-axis images, represented by the outer sets of shifted circles, with a larger tilt of the illumination plane wave, approaching grazing incidence (limited to 80° by practical considerations such as Fresnel reflectivity in the present experiment). The maximum frequency coverage in these images extends to $[\sin(80)+NA]/\lambda=(0.98+NA)/\lambda=(1.38/\lambda)$. The frequency-space coverage of the outer circles may be necessary to capture the fundamental frequency components of the line-space portion of this pattern. There is significant overlap between the frequency coverage of the first and second set of partial images as illustrated in FIG. 8B. To provide a faithful image, the double coverage of frequency space associated with the image spectral overlaps can be excluded. This can be accomplished by filtering the images either optically (with appropriate apertures in the back focal plane) or electronically once the images are recorded. Importantly, since each of the partial images involves only the NA of the objective, this imaging concept retains the working distance, depth-of-field and field-of-view associated with the low-NA objective, but has a resolution beyond that achievable with even the highest NA objective using traditional illumination approaches.

Figure 9:
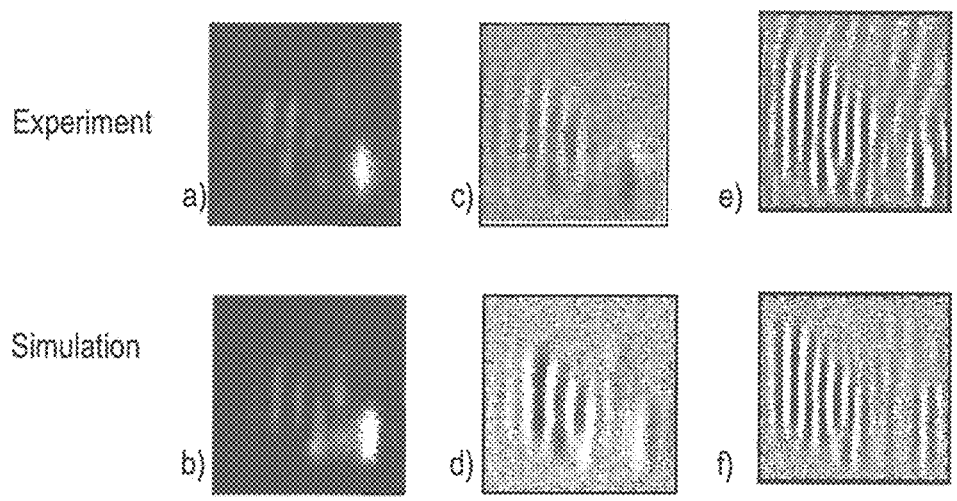
FIGS. 9A-9F show the preliminary results of an experiment using an NA=0.4 objective with a He—Ne laser illumination ($\lambda$=633 nm) and with about 240 nm structure with corresponding simulations using the configuration presented in FIG. 5A.

FIGS. 9A-9F show the preliminary results of an experiment using an NA=0.4 objective with a He—Ne laser illumination ($\lambda$=633 nm) and with about a 240 nm critical dimension structure with corresponding simulations using the configuration presented in FIG. 5D, blocking the zero-order beam of the reference in the objective lens pupil. FIG. 9A is the mixed image corresponding to the interference of the low and high images and FIG. 9B is the corresponding simulation result. FIG. 9C is the image after subtraction dark field and low frequency image and FIG. 9D is the corresponding simulation result. FIG. 9E is restored high frequency image and FIG. 9F is the corresponding simulated result.

Figure 10:
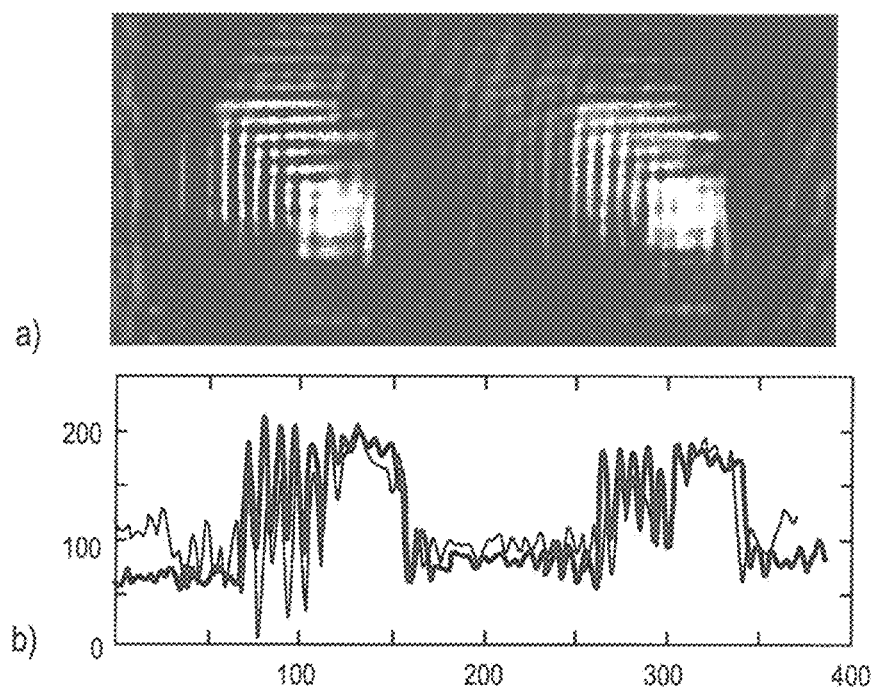
FIG. 10A shows reconstructed images of 260 nm and 240 nm CD structures obtained using the optical configuration of FIG. 5A after the dark field subtraction, frequency shifting correction, and sub-image combination.
FIG. 10B show a crosscut (gray) of the images of FIG. 10A compared with a crosscut of corresponding simulation (black).
Figure 11:
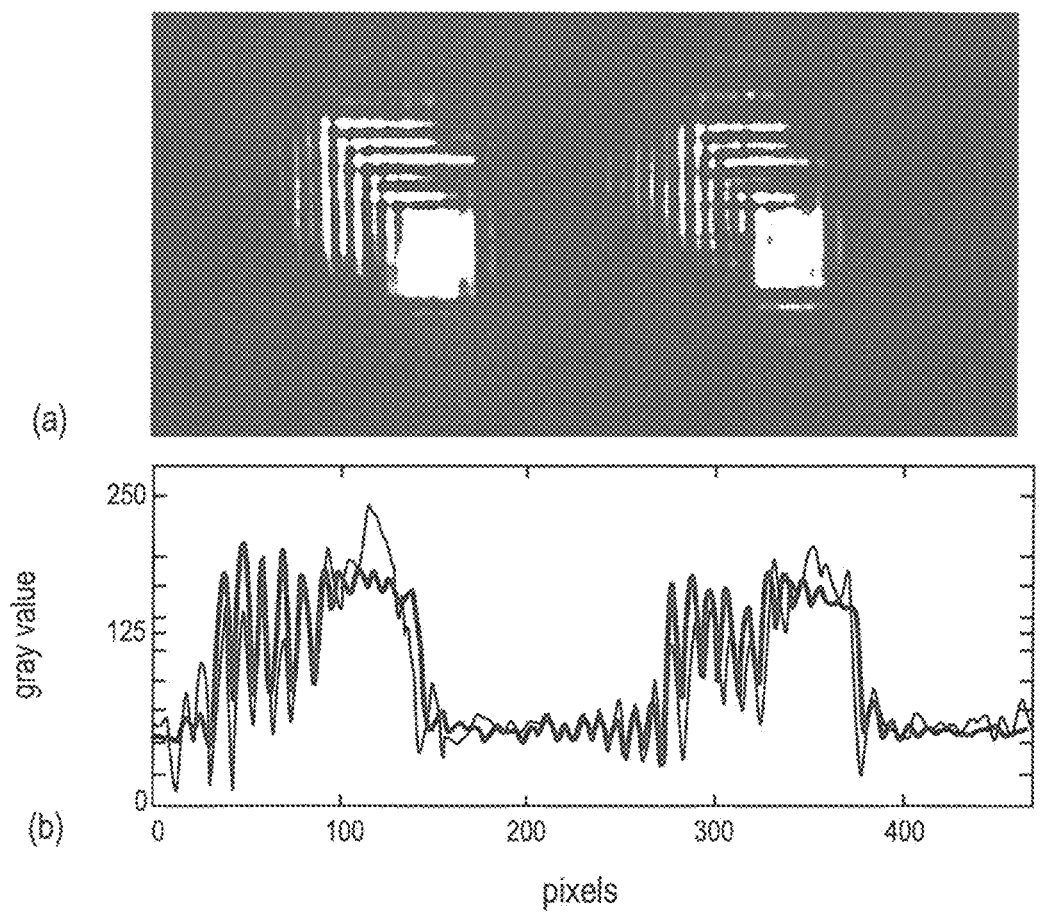
FIG. 11A shows reconstructed images of 260 nm and 240 nm CD structures obtained using the optical arrangement shown in FIG. 5E.
FIG. 11B shows a crosscut (gray) of the images of FIG. 10A compared with a crosscut of corresponding simulation (black).

Similarly, results using dynamic (adjustable on/off) physical block presented in FIG. 5A are shown in FIG. 10A. The same 260- and 240-nm objects are imaged as in FIG. 9C; only the final results after the dark field subtraction, frequency shifting correction and sub-image combination are shown. The corresponding cross-cuts are shown in FIG. 10B. A total of four offset images, two each in the x- and y-directions, with $\theta_{ill}$=53° and 80° were used along with a 0.4 NA objective. As discussed previously, this configuration provided resolution to <~240 nm CD. There is overlap in the frequency space coverage between these two exposures and electronic frequency space filtering is used to assure a uniform coverage of frequency space. The present Manhattan geometry structure has spectral content concentrated along the x- and y-directions, so the offset illuminations were restricted to those directions. Adding additional frequency-space coverage for arbitrarily shaped structures can be accomplished by taking additional sub-images with rotation of the object in the (x,y) plane. The spatial frequency content of the image covers a wide range as a result of the large box (at 10× the linewidth of the linespace structures). The reconstructed image of the same structures obtained by the method with the beamsplitter configuration presented in FIG. 5E is shown in FIG. 11A and a crosscut of the image with corresponding simulation is shown in FIG. 11B. The quality of the results for both methods is quite comparable. The second method retains a long working distance, but requires access to the imaging system pupil for blocking the zero-order. The first method does not require any modification to the traditional microscopy components, but has reduced working distance due to the beamsplitter in front of the objective. There are some extra features experimentally as compared to the model due to the lack of precision in mutual phase determination between the sub-images and speckle effects from the coherent illumination. These issues can be reduced by using improved arrangements and lower coherence sources. There are other possible alternatives; the optimum choice will depend on the specifics of the object and the constraints of specific optical systems.

The embodiments discussed so far provide spatial frequency coverage up to $2\lambda(\sin(\theta_{ill})+NA)/\lambda \pm 2\pi(1+NA)/\lambda$; that is the maximum illumination angle offset can be set close to 90° (providing the "1") and the maximum angle collected by the objective lens corresponds to $\sin^{-1}(NA)$. As was previously disclosed in relation to the interferometric implementation of IIM, additional spatial frequencies are available by tilting the object plane relative to the objective lens axis. This allows collection of spatial frequencies up to $4\pi/\lambda$, independent of the lens NA. The cost is a more complex signal processing requirement since the tilted object plane results in a nonlinear mapping of spatial frequencies from the object plane to the laboratory image that must be corrected to achieve a good image. This mapping has been discussed previously. The additional frequency space (and hence smaller image features) are available in the structured illumination embodiments of IIM disclosed herein.

Immersion microscopy is well known to provide higher spatial frequencies by a factor of the refractive index of the immersion medium, n, thereby extending the spatial frequency range to as high as $2n/\lambda$. Again the advantages of immersion are directly applicable to structured illumination IIM.

Traditionally immersion microscopy has been practiced in reflection with a liquid medium on top of the object, or in transmission where advantage is taken of the high refractive index of the substrate ($n_{sub}$) as well as that of a liquid on top of the object. An intermediate possibility is to use the refractive index of the substrate without an immersion fluid. In this case the spatial frequency range is extended to $2\pi(n_{sub}+NA)/\lambda$.

Figure 12:
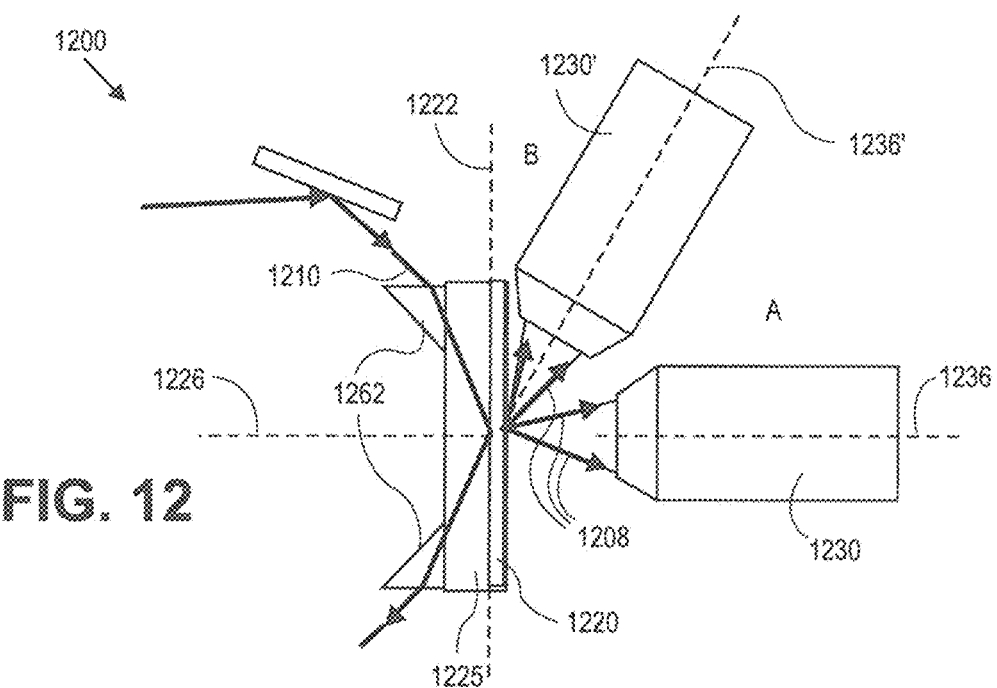
FIG. 12A shows an exemplary IIM arrangement with evanescent illumination, according to various embodiments of the present teachings.
FIG. 12B shows an exemplary IIM arrangement with evanescent illumination with a rotated optical axis, according to various embodiments of the present teachings.

FIG. 12 shows an exemplary apparatus 1200 for microscopy with an IIM arrangement with illumination by evanescent waves extending from a substrate, where 12A and B refers to alternate positions of the collection lens, according to various embodiments of the present teachings. The apparatus 1200 can include an object plane 1222 on which can be disposed a first surface of a substrate 1225, wherein the substrate 1225, upon which is an object 1220, is characterized by a homogeneous refractive index ($n_{sub}$) and a surface normal 1226. The apparatus 1200 can also include a first optical system, including prisms 1262 and substrate 1265, disposed to provide a substantially coherent evanescent wave illumination of the object 1220, the illumination 1210 characterized by a wavelength $\lambda$ and a radius of curvature and disposed at one of a plurality of incident wave vectors from about $2\pi/\lambda$ to about $2\pi n_{sub}/\lambda$ with respect to a surface normal of the substrate and at a plurality of azimuth angles spanning from about 0 to about $2\pi$, wherein the plurality of incident wave vectors correspond to angles beyond a total internal reflection angle $\theta_c$ of the substrate. The apparatus 1200 can also include a second optical system 1230 disposed to collect portions of the illumination 1208 scattered from the object plane 1222, the second optical system 1230 having an optical axis 1236 disposed at one of a plurality of center wave vectors from about 0 to about $2\pi/\lambda$ (or angles from about 0 to about $\pi$) with respect to the substrate 1225 surface normal and at the azimuth angle corresponding to the illumination of the first optical system, wherein the second optical system 1230 is characterized by a numerical aperture (NA). FIG. 12B shows arrangement with tilted optical axis 1236'. The apparatus 1200 can also include a third optical system disposed in an optical path of the first optical system to provide interferometric reintroduction of a portion of the coherent illumination (reference beam) into the second optical system 1230 or 1230', wherein each of an amplitude, a phase, a radius of curvature and an angle of incidence of the reference is adjusted such that a correct reference wave is present at the image plane of the second optical system. The apparatus 1200 can further include an electronic image device disposed at an image plane of the second optical system that responds linearly to the local optical intensity and transfers the local optical intensity map across the image plane (a sub-image) to a signal processor device in electronic form. The apparatus 1200 can also include a device for adjusting the first, the second, and the third optical systems to collect sub-images for different pairs of the pluralities of incident (first optical system) and collection center (second optical system) wave vectors so as to sequentially obtain a plurality of sub-images corresponding to a plurality of regions of spatial frequency space and an electronic device to sequentially receive the electronic form of the sub-images and manipulate the sub-images to correct for distortions and alterations introduced by the optical configuration, store, and combine the plurality of sub-images corresponding to the plurality of regions of spatial frequency space to create a composite image corresponding to a synthetic aperture that is larger than the physical aperture of the collection lens 1230 or 1230'.

In some embodiments, the third optical system can further include a first beamsplitter disposed in the optical path of the first optical system before the object to collect a portion of the coherent illumination and one or more optics disposed between the first optical system and the second optical system 1230 are prisms 1262 within first optical system used to inject into substrate at angles beyond total internal reflection to interferometrically reintroduce the portion of the coherent illumination as a reference beam into the second optical system 1230 in a position after the exit aperture of a collection (objective) lens, wherein the reintroduction is at one of a position corresponding to a position a zero-order beam would have had if it had been transmitted through a higher NA lens of the second optical system 1230 or an aliased position to reduce pixel requirements of the electronic image device, wherein the signal processor is adjusted to compensate for this spatial frequency aliasing (the same concept as the local oscillator frequency introduced earlier). In other embodiments, the third optical system of the apparatus 1200 can include one of the configurations shown in FIGS. 5A-5E.

In certain embodiments apparatus 1200 for microscopy with an IIM arrangement with illumination by evanescent waves extending from a substrate can also include at least one known reference object to cover a small part of the image field.

According to various embodiments, there is a method for microscopy by evanescent illumination through a substrate. The method can include providing an object 1220 disposed on a surface of a planar substrate 1225 characterized by a homogeneous refractive index ($n_{sub}$) and a surface normal 1226 and providing a first optical system disposed to provide an evanescent wave illumination of the object plane 1222 by providing a substantially coherent illumination of the object plane 1222, the illumination characterized by a wavelength $\lambda$ and a radius of curvature and disposed at one of a plurality of incident wave vectors from about $2\pi/\lambda$ to about $2\pi n_{sub}/\lambda$ with respect to a surface normal of the substrate and at a multiplicity of azimuth angles spanning 0 to $2\pi$, wherein the plurality of incident wave vectors correspond to angles beyond a total internal reflection angle $\theta_c$ of the substrate. The method can further include providing a second optical system 1230 having an optical axis 1236 disposed at one of a plurality of center wave vectors from about 0 to about $2\pi/\lambda$ with respect to the normal to the plane parallel optical element, wherein the second optical system 1230 is characterized by a numerical aperture (NA). The method can also include providing a third optical system disposed in an optical path of the first optical system to provide interferometric reintroduction of a portion of the coherent plane wave illumination (reference beam) into the second optical system 1230, wherein the amplitude, phase, and position of the reintroduced illumination wave in the image plane of the second optical system 1230 can be adjusted. The method can further include recording a sub-image of the object 1220 at an object plane 1222 using an electronic image device, wherein the sub-image is formed as a result of interference of the scattering from the coherent plane wave illumination of the object and the reference beam; adjusting the first, the second, and the third optical systems to sequentially collect a plurality of sub-images corresponding to a plurality of regions of spatial frequency space; manipulating each of the plurality of sub-images using a signal processor to correct for distortions and alterations introduced by the optical configuration; and combining the plurality of sub-images into a composite image to provide a substantially faithful image of the object. In various embodiments, the method can further include one or more processes of subtraction of dark field images, subtraction of background images, shifting of spatial frequencies in accordance with the optical configuration, and elimination of one or more overlapping coverages of the frequency space wherein the elimination operations can be performed either in the optical systems or in the signal processing. In some embodiments, the method can also include selection of the regions of spatial frequency space to provide a more or less faithful image of the object in the object plane. Neumann et al. in Optics Express, Vol. 16, No. 25, 2008 pp 20477-20483 describes an evanescent wave illumination for further extending the resolution limit of imaging interferometric microscopy to $\lambda\backslash2(n_{sub}+1)$, the disclosure of which is incorporated herein by reference in its entirety.

In various embodiments, the step of providing an object 1220 disposed on a surface of a planar substrate 1225 can include providing a cladding layer surrounding the object 1220 and the object 1220 disposed over the substrate 1225. The extent of excitation region due to evanescent wave illumination, normal to the interface is given by an exponential decay function with a 1/e length of $\lambda/2\pi\sqrt{n_{pp}^2\sin^2\theta - n_{clad}^2}$, where $n_{sub}$ is the refractive index of the substrate and $n_{clad}$ is the refractive index of the superstrate or cladding material surrounding the object 1220. The spatial localization can provide benefit, for example in TIRF (total internal reflection fluorescence) the localization is much larger than can be achieved with a simple focus or even with confocal microscopy. In other cases, this decay length can be a restriction, for example, in lithography studies where there might be multiple layers of material (bottom AR coating and photoresist for example) and the structural variation between these layers is of interest. Hence, the addition of a cladding layer surrounding the object can allow some degree of tuning of the decay length, and thereby control the signal to noise ratio.

Figure 13A:
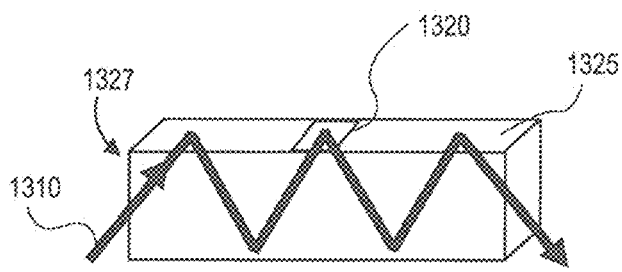
FIGS. 13A-13C show alternate approaches for coupling light for substrate illumination, in accordance with various embodiments.
Figure 13B:
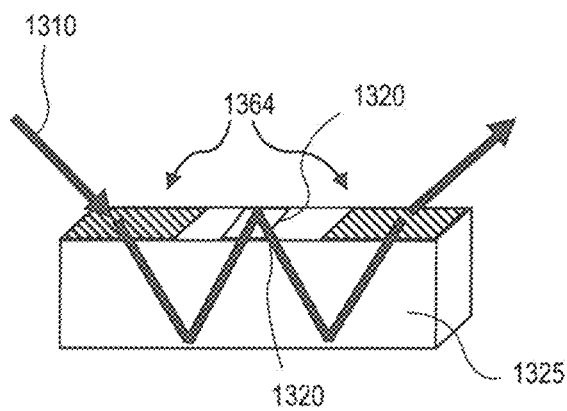
Figure 13C:
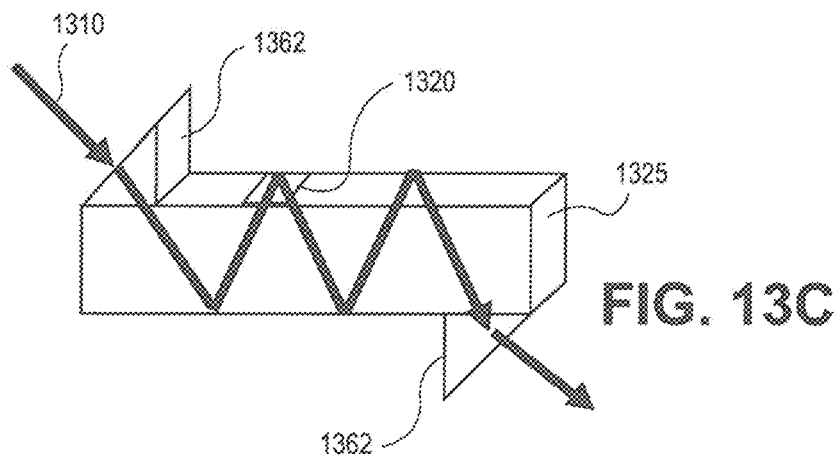

FIGS. 13A-13C shows several exemplary techniques for part of the first optical system to provide illumination through the substrate 1325. FIG. 13A shows coupling of incident beam 1310 through a side 1326 of the substrate 1325, which can be polished at an angle different from normal to the object 1320; in other words the substrate 1325 can be a prism. FIG. 13B shows one or more gratings 1364 on a side of the substrate 1325 the same as that where the object 1320 can be located. Alternatively, the gratings 1364 can be placed on a side opposite to that of the object 1320. FIG. 13C shows coupling of the incident beam 1310 using one or more prisms 1362.

Figure 14A:
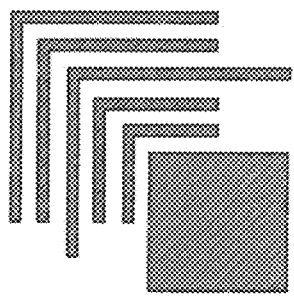
FIG. 14A schematically illustrates a Manhattan geometry pattern used for image resolution exploration consisting of five nested "ells" and a large box.
Figure 14B:
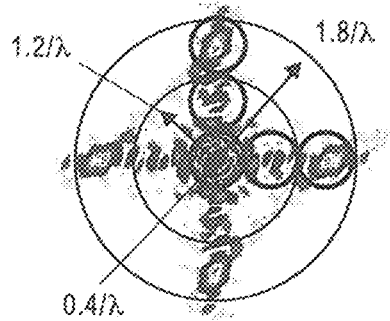
FIG. 14B illustrates intensity Fourier space components of the Manhattan geometry pattern shown in FIG. 14A, mapped onto a frequency space coverage of the imaging system, for a structure with CD=180 nm for the optical arrangement shown in FIG. 3.
Figure 14C:
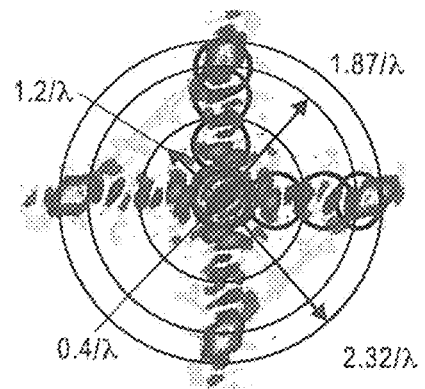
FIG. 14C illustrates intensity Fourier space components of the Manhattan geometry pattern shown in FIG. 12A, mapped onto a frequency space coverage of the imaging system, for a structure with CD=150 nm for the optical arrangement shown in FIG. 11A.

FIG. 14A shows a Manhattan (x-, y-geometry) test pattern, scaled to different dimensions. The Fourier intensity transform of this pattern for a linewidth (critical dimension or CD) of 180 nm is shown in FIG. 14B and for a CD of 150 nm in FIG. 13C. The circles in FIGS. 14B and 14C correspond to the bandpass limits of various microscopy configurations. The circle in the center of FIG. 14B, with a radius of $NA/\lambda=0.4/\lambda$, corresponds to the Abbé-limit spatial frequency range captured with on-axis coherent illumination ($NA_{ill}=0$). The inner set of shifted circles in FIG. 14B (only single sidebands are shown for clarity; the complex conjugate regions are covered as well) correspond to IIM with off-axis illumination beams at $\theta_{ill}=53°$ in the x, y-directions that extend the frequency coverage to a radius $3NA/\lambda\sim1.2/\lambda$. Additional frequency space coverage (second pair of circles) is available using evanescent wave illumination extending the frequency space coverage to a radius of $(n_{sub} \sin \theta_{ill}'NA)/\lambda\sim1.87/\lambda$ (with $\theta_{ill}'=76°$) without tilt of the microscope optical axis. The frequency space coverage along with the corresponding structure Fourier intensity plot for the structure with CD=150 nm is shown in FIG. 14C. The third pair of off-axis sub-images in FIG. 14C correspond to the tilted optical axis. This frequency region is elliptical rather than circular, due to non-paraxial and conical diffraction effects associated with the off-axis optical system.

FIG. 15A shows the experimental result for an object containing both 180- and 170-nm CD structures in a single large-field image using the apparatus of FIG. 12A (two pairs of offset illumination, one at 53° in air and one at 76° in the substrate and collection with the optical axis along the substrate's surface normal as shown in FIG. 12A. The 180-nm CD object is within the bandwidth capabilities of this optical system while the 170-nm CD object has significant spatial frequencies that extend beyond the optical system bandwidth and so is not fully resolved. The five nested "ell" shapes are distinguishable for the 180-nm CD, but not for the 170-nm CD. The positions of the two objects are correctly restored by the image restoration procedure as is evident from the good positional overlap between the experimental and theoretical cross-cuts in FIG. 15B.

FIG. 16A shows reconstructed high frequency image of a 150 nm structure using evanescent illumination and a tilted optical system, shown in FIG. 12B, with the highest spatial frequencies collected with the optical axis tilted with respect to the substrate's surface normal. FIG. 16B shows high frequency image simulation of a 150 nm structure using evanescent illumination and a tilted optical system, shown in FIG. 12B. FIG. 16C shows experimental and simulation cross-cuts of images shown in FIGS. 16A and 16B. FIG. 16D shows reconstructed composite image of a 150 nm structure using evanescent illumination and a tilted optical system, shown in FIG. 12B. FIG. 16E shows composite image simulation of a 150 nm structure using evanescent illumination and a tilted optical system, shown in FIG. 12B. FIG. 16F shows experimental and simulation cross-cuts of images shown in FIGS. 16D and 16E.

Evanescent illumination can be combined with structural illumination eliminating the need for access to the back focal plane. This moves the interferometer to the front of the objective lens and makes IIM readily adaptable to existing microscopes. Structural illumination is roughly equivalent to recording the spectral information at an intermediate frequency; additional computation is required to reset the frequencies. But this frequency shifting can reduce the camera pixel size and count requirements. Evanescent wave illumination can be used to extend the resolution of IIM to $\lambda/2(n+1)$. Furthermore, IIM provides an important advantage over conventional immersion microscopy techniques. Since only a relatively small region of frequency space (~NA/$\lambda$) is recorded in each sub-image, the aberration requirements on the objective lens are dramatically reduced. Hence, a simple set of prisms or gratings can be used to extract, and conventional air-based lenses to capture, the information. As is always the case, there is a trade-off between the number of sub-images and the NA of the objective lens.

Figure 17:
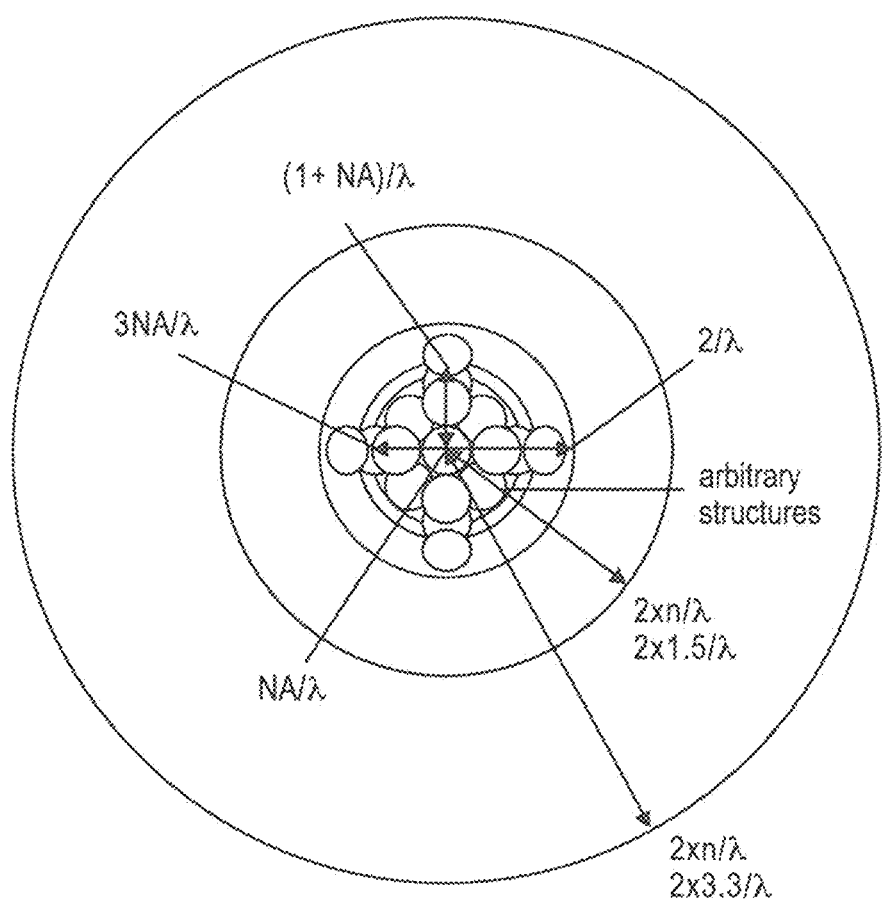
FIG. 17 shows available frequency space coverage for various IIM optical configurations, in accordance with the present teachings.

FIG. 17 shows the possible increase of $NA_{eff}$, drawn for a 0.4 NA system. As the frequency coverage is extended, the use of higher NA lenses can reduce the number of sub-images required for a more complete coverage of frequency space. Of course the required coverage is dependent on the pattern, and there are some applications, for example in metrology for integrated circuits, where coverage of a subset of the full frequency space is appropriate, where the range of spatial frequencies in the object are limited by lithographic consideration.

Figure 18:
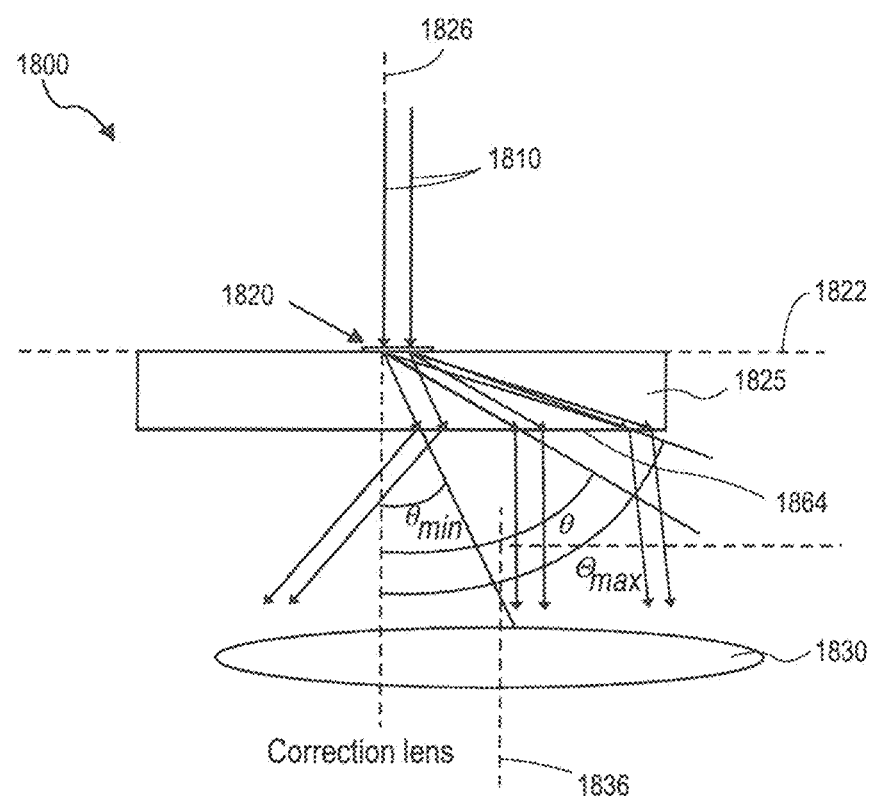
FIG. 18 shows a schematic diagram showing the high angle light scattered from an object and extracted from the substrate using at least one grating, in accordance with various embodiments of the present teachings.

There are diffracted beams corresponding to even larger spatial frequencies (smaller features) scattered back into the substrate at angles larger than the critical angle. These beams are totally internally reflected and are not accessible. FIG. 18 shows another exemplary IIM optical arrangement for an apparatus 1800 for microscopy that provides access to the higher spatial frequency terms and thereby provides higher resolution, according to various embodiments of the present teachings. The apparatus 1800 can include an object plane 1822 on which can be disposed a first surface of a planar substrate 1825, wherein the substrate 1825 is characterized by a homogeneous refractive index ($n_{sub}$) and a normal 1826. The apparatus 1800 can also include a first optical system disposed to provide a substantially coherent illumination of the object plane, the illumination characterized by a wavelength $\lambda$ and a radius of curvature and disposed at one of a plurality of incident wave vectors from about 0 to about $2\pi n_{sub}/\lambda$ with respect to a surface normal 1826 of the substrate 1825 and at a plurality of azimuth angles spanning from about 0 to about $2\pi$. The apparatus 1800 can further include at least one grating 1864 on the side of the substrate 1825 opposite the object plane 1822, wherein each grating 1864 is characterized by a period, a depth, a grating profile, a position, and an extent to further transform the scattered waves in the substrate reflected from the illumination by the object into propagating waves in the medium below the substrate. In some embodiments, the medium below the substrate 1825 can be air. In other embodiments, the medium can be a vacuum. However, the medium can include any other suitable material. The apparatus 1800 can further include a second optical system 1830 having an optical axis 1836 disposed at one of a plurality of center wave vectors from about 0 to about $2\pi/\lambda$ (or angles from about 0 to about $\pi$) with respect to the surface normal 1826, wherein the second optical system 1830 can include one or more gratings 1864 on the second side of the substrate 1825 and is characterized by a numerical aperture (NA). The apparatus 1800 can also include a third optical system disposed in an optical path of the first optical system to provide interferometric reintroduction of a portion of the coherent illumination (reference beam) into the second optical system 1830, wherein each of an amplitude, a phase, a radius of curvature, path length, and an angle of incidence of the reference can be adjusted such that a correct reference wave is present at the image plane of the second optical system. The apparatus 1800 can further include an electronic image device disposed at an image plane of the second optical system 1830 that responds linearly to the local optical intensity and transfers the local optical intensity map across the image plane (a sub-image) to a signal processor device in electronic form, a signal processor that receives the electronic form of the sub-image and manipulates the sub-image to correct for distortions and alteration introduced by the optical configuration, and to collect, store and combine a plurality of sub-images corresponding to a plurality of regions of spatial frequency space to create a composite image, wherein the plurality of sub-images are formed as a result of adjustments to the first, the second, and the third optical systems. In various embodiments, the third optical system of the apparatus 1800 can include one of the third optical system configurations shown in FIGS. 5A-5E.

In various embodiments, the grating 1864 profile can have an impact on the extraction efficiency. In some embodiments, the grating 1864 can have a sinusoidal profile. A sinusoidal grating has components in its Fourier transform only at ±1/d. In other embodiments, the grating 1864 can have a rectangular profile. A rectangular grating has many more Fourier components that can lead to coupling of additional scattered image plane waves across the interface. For equal line: space grating, the second order Fourier coefficient (@±2/d) vanishes, although for sufficiently deep gratings, comparable to the wavelength, additional coupling terms can arise. The third order terms (@±3/d) are always present for rectangular grating profiles. This can give rise to multiple coupling orders which can lead to artifacts in the sub-images. In some arrangements, this is not an issue because of the spatial separation of the scattered spatial frequency information at the bottom of the substrate (as can be seen in FIG. 18). In this case, the bottom substrate plane is separated from the object plane and the different spatial frequency components, propagating at different angles, have separated to some extent by the time they reach this plane. If the thickness of the substrate 1825 is significantly larger than the field of view (illuminated aperture at the image plane), this separation can be large enough to avoid issues associated with higher order coupling at the bottom surface extraction grating. Thus, there is engineering trade-off in choosing the thickness of the substrate 1825, the separation is better if it is thicker, but the phase distortions are increased.

Figure 19:
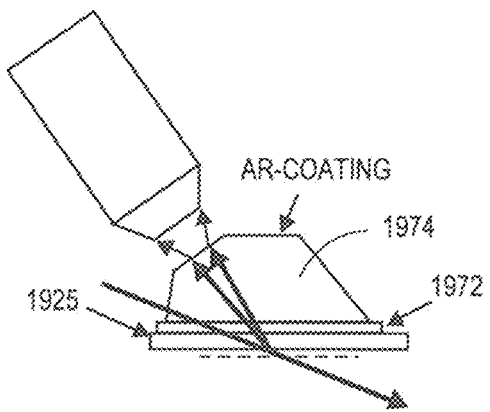
FIG. 19 shows prism coupling for extracting light scattered into a substrate, in accordance with various teachings.

Alternative collection schemes can include using one or more prisms 1974, as shown in FIG. 19. In some embodiments, the prism 1974 can be fabricated as part of the substrate 1925. In other embodiments, index matching fluid 1972 can be used.

In certain embodiments apparatus 1800 for microscopy can also include at least one known reference object to cover a small part of the image field.

According to various embodiments, there is a method for microscopy by illumination through a substrate. The method can include providing an object 1820 disposed over a first side of a planar substrate 1825, the substrate characterized by a homogeneous refractive index ($n_{sub}$) and a surface normal 1826 such that the object 1820 is separated from the substrate 1825 by a distance of no more than about ≤λ. The method can also include providing at least one grating 1864 on the side of the substrate 1825 opposite the object plane 1822, each grating 1864 characterized by a position, a period, a depth, and a grating profile, wherein each of the gratings 1864 can further scatter reflected waves resulting from the coherent illumination of the object into propagating waves in the medium below the substrate. The method can further include providing a first optical system disposed to provide a substantially coherent illumination of the object plane, the illumination characterized by a wavelength λ and a radius of curvature and disposed at one of a plurality of incident wave vectors from about 0 to about $2\pi n_{sub}/\lambda$ with respect to a surface normal of the substrate and at a plurality of azimuth angles spanning from about 0 to about 2π. The method can also include providing a second optical system 1830 having an optical axis 1836 disposed at one of a plurality of center wave vectors from about 0 to about $2\pi/\lambda$ with respect to the surface normal 1826, wherein the second optical system 1830 includes at least one grating 1864 on the second side of the substrate 1825 and is characterized by a numerical aperture (NA). The method can further include providing a third optical system disposed in an optical path of the first optical system to provide interferometric reintroduction of a portion of the coherent illumination (reference beam) into the second optical system 1830, wherein each of an amplitude, a phase, a radius of curvature and an angle of incidence of the reference is adjusted as required such that a corrected reference wave is present at the image plane of the second optical system 1830. The method can also include providing an electronic image device disposed at an image plane of the second optical system 1830 that responds linearly to the local optical intensity and transfers the local optical intensity map across the image plane (a sub-image) to a signal processor device in electronic form, providing a signal processor that receives the electronic form of the sub-image, manipulating each of the plurality of sub-images using the signal processor to correct for distortions and alterations introduced by the optical configuration, and combining the plurality of sub-images into a composite image to provide a substantially faithful image of the object. In various embodiments, the method can further include one or more processes of subtraction of dark field images, subtraction of background images, shifting of spatial frequencies in accordance with the optical configuration, and elimination of one or more overlapping coverages of the frequency space wherein the elimination operations can be performed either in the optical systems or in the signal processing. In some embodiments, the method can also include selecting regions of spatial frequency space to provide a more or less faithful image of the object in the object plane.

For various IIM configurations shown in FIGS. 3, 12, and 18, the coherence length>>sample (object) dimensions. The He—Ne laser has a long coherence length of many cm, and this makes the experimental arrangement simpler, as it is not necessary to critically match the interferometer lengths between the objective arm and the zero-order reinjection arm. However, it does increase spurious speckle effects associated with stray light and multiple reflections from various optical surfaces in the set-up. These effects can be mitigated by choosing a source with sufficient coherence for the IIM measurements, but insufficient coherence for Fabry-Perot effects, e.g. between the front and back sides of the substrate or between the substrate and the objective entrance surface. Since, these dimensions are very different, μm scale for the sample to several mm for the substrate thickness and substrate to objective distance, it is possible to minimize unrelated Fabry-Perot effects while retaining all of the resolution of IIM.

Tiling of Frequency Space

In general, the spatial frequency location of the information corresponding to a specific angle of illumination (including illumination through the substrate) and angle of collection (θ) corresponds to $$\vec{k}_{scatter} = \frac{2\pi(n)}{\lambda}\sin\theta_{illumination}\hat{e}_{illumination} - \frac{2\pi n_{pp}}{\lambda}\sin\theta_{scattered}\hat{e}_{scattered}$$

In the above equation, (n) in the first term is adjusted as appropriate, for example, for illumination in air, $n_{pp}=1$ while for illumination (evanescent) through a substrate, $n=n_{sub}=1.5$ for glass. In keeping with the notation established above, $\theta_{scattered}$ is the angle in the substrate and so the factor $n_{sub}$ is appropriate; a grating can be used to shift the spatial frequencies into the air propagation bandpass as necessary.

Both angles as well as the pitch of any gratings can provide some flexibility in the tiling of frequency space, i.e. in choosing the regions of frequency images into a complete image. The maximum spatial frequency, $k_{max}=2\pi f_{max}=2\pi(2n_{sub}/\lambda)$ is obtained when both angles are close to 90°. Since a half pitch can be resolved, this leads to an Abbe resolution limit of $\lambda/4n_{sub}$. The optimum strategy is pattern dependent, for example, for Manhattan geometry structures with edges confined to a rectangular grid, often found in integrated circuits, it is important to capture the frequency information along the axes and of less consequence to capture the information away from the axes where the Fourier transform of the pattern has lower spectral intensity. In the examples shown in FIGS. 19A and 19B, only one principal axis is considered, but the generalization to complete coverage is straightforward.

Figure 20A:
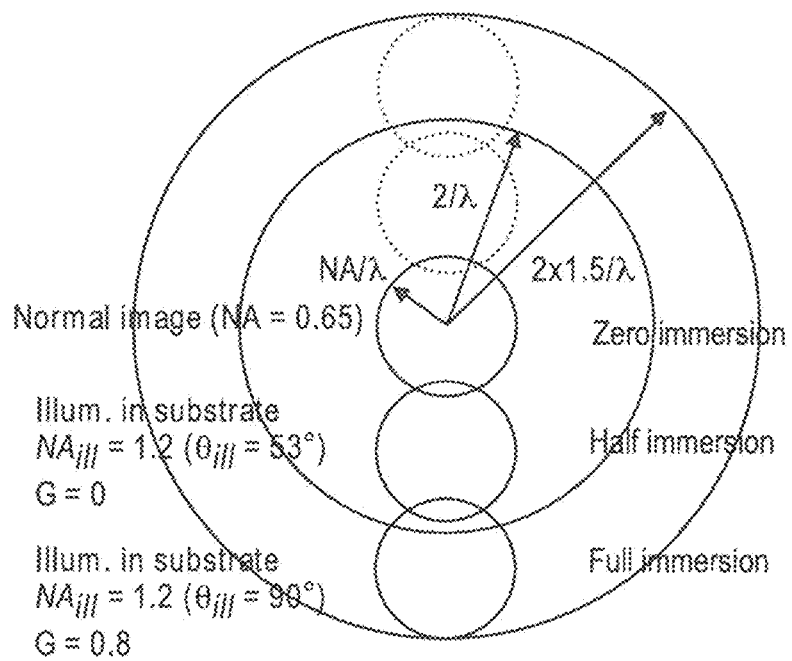
FIGS. 20A and 20B show embodiments for tiling frequency space with a substrate (n=1.5) in one direction, in accordance with various embodiments.
Figure 20B:
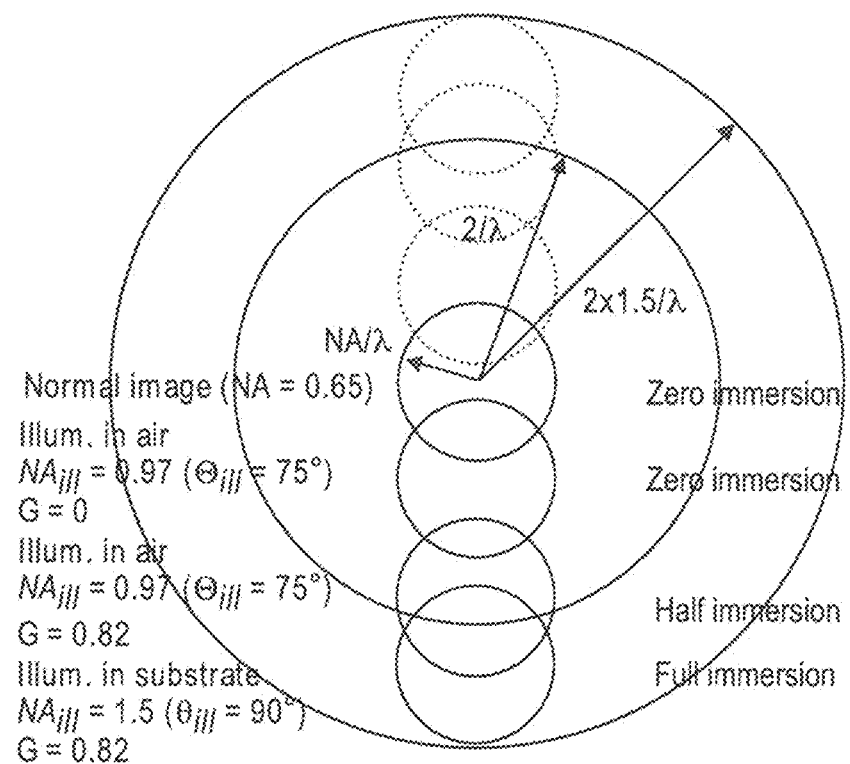

FIGS. 20A and 20B show two alternate embodiments for providing coverage from $f_x=0$ to $f_x=2n_{sub}/\lambda$ with a fixed objective NA. The frequency space coverages shown in FIGS. 20A and 20B are designed for a maximum spatial frequency of $3/\lambda(2n_{sub}/\lambda)$, and an objective of NA of 0.65. In FIG. 20A, a minimum number of sub-images are used. The central small circle corresponds to conventional, normal incidence coherent illumination with the radius of the circle being about $0.65/\lambda$. The next sub-image is taken with off-axis illumination through the substrate at an angle of about 53°; this corresponds to effective $NA_{ill}$ of about 1.2. The scattered light can be detected either from the top (through air) or through the substrate, the collection geometry can be similar to that shown in FIG. 18, except for the illumination direction. A zero-order (interferometric reference) beam can be used in IIM to provide access to the essential phase information as well as to allow unambiguous assignment of the directly measured spatial frequencies. The square law, intensity detection process restores both the complex conjugate frequencies within the symmetrically located dotted circle in the figure. A third sub-image can be taken with grazing incidence illumination through the substrate, and with higher scattered spatial frequencies with the use of a grating of period $\lambda/0.8$ for extraction as in FIG. 18. Again, the complex conjugate spatial frequencies are restored by the square-law detection process. For a Manhattan geometry object, a similar set of sub-images in the orthogonal direction can be used, for a total of five sub-images; arbitrary structures may require additional sub-images to fill all of frequency space.

FIG. 20B shows a second tiling embodiment, using four sub-images, but provides more robust coverage of frequency space (fewer missed spatial frequencies in the regions where the circles abut). The central circle is the same as in the previous example, illumination at normal incidence and collection with a conventional 0.65 NA optical system. The second innermost set of circles corresponds to illumination at grazing incidence in air ($NA_{ill}\sim1$). The next innermost set corresponds to the same illumination condition, but to collection through a glass substrate. The final outermost set of circles corresponds to illumination at grazing incidence through the substrate and collection with the same grating to allow high spatial frequencies (collection of light scatted at angles beyond the critical angle in the glass). The disclosed exemplary embodiments provide an example of the flexibility offered by the IIM process. The choice of tiling strategy will depend on the object to be imaged. In general, it is best not to put a collection boundary in a region of high spectral intensity to minimize Gibbs effect oscillations of the observed sub-image structure. In addition, the strength of scattered spatial frequency components in the regions between the circles will be a factor in selecting an IIM tiling strategy.

It should be noted that the tiling with circular regions is not a requirement, but is convenient as a result of the symmetry of optical lenses. In some cases, a square aperture, which can be provided either optically or electronically during the sub-image manipulations, can prove advantageous. In particular, a square aperture can be configured to provide more robust coverage at the boundaries between sub-images (e.g. two squares can match along the line, while two circles can only touch at a point). The tilings in FIG. 19B show some overlap regions. Several strategies are available for dealing with the multiple counting in frequency space that these overlaps imply. The simplest is just to remove the double counting in the computation of the sub-image combination. Alternatively, a graded transfer function can be applied in the region of the overlap to minimize artifacts from imperfect cancellation of Gibbs effect oscillations in the two sub-images. The simplest approach is to calculate the Fourier transform of the sub-image, apply appropriate filters and inverse transform back to real space. The apparatus of image signal processing is very rich, and many of its techniques can be applied to this image reconstruction problem.

Figure 21:
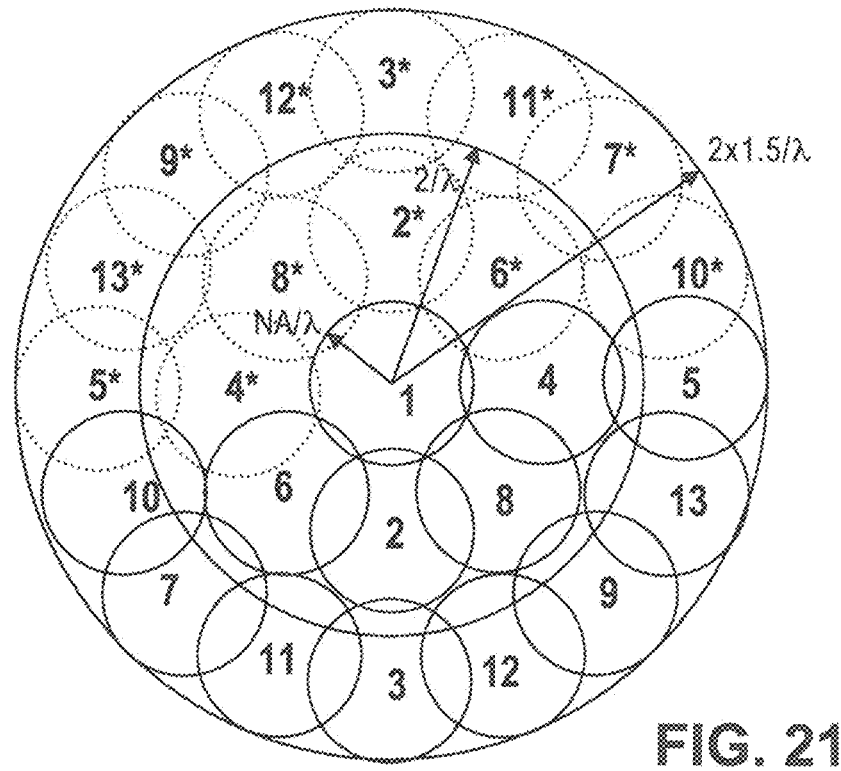
FIG. 21 show an exemplary tiling with almost complete frequency space coverage (NA=0.65, n=1.5), in accordance with present teachings.

For arbitrary images, where a-priori information on likely orientations and spatial frequency content is not available, for example biological specimens, additional sub-images can be used in order to get a more complete coverage of spatial frequency space. An example of covering most of spatial frequency space is given in FIG. 21. This consists of 13 sub-images: the two off-axis sub-images shown in the top of FIG. 20A are repeated with rotation angles of 45°, 90° and 135° (there is no need to repeat the low-frequency sub-image) for a total of 9 sub-images; additional high frequency sub-images at rotation angles of 22.5°, 67.5°, 112.5°, and 157.5°, for a total of 13 sub-images, complete the coverage except for small regions near the outer periphery of frequency space. It should be noted that there are only three optical configurations; on-axis illumination (low frequency), middle frequency, and high frequency, the remaining sub-images are obtained by a simple sample rotation. Furthermore, provision can be made for illumination through the substrate for the middle and high frequency coverage as the sample is rotated.

Figure 22:
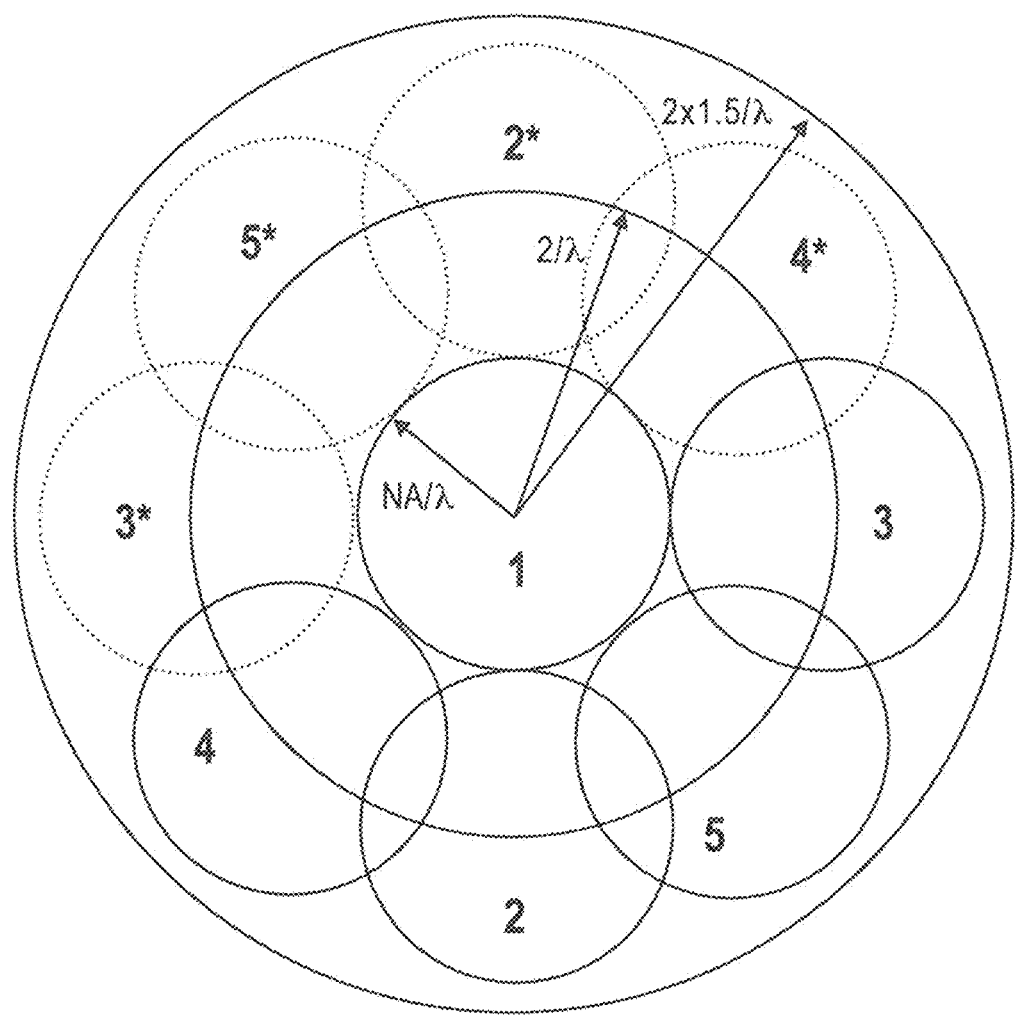
FIG. 22 show another exemplary tiling with a larger NA objective lens (NA=0.95, n=1.5), in accordance with various embodiments.

The number of sub-images can be reduced by increasing the objective NA. As can be seen in FIG. 22, the number of sub-images for nearly full coverage is reduced to 5 for a NA=0.95, corresponding to a very high NA air-based objective. The specifics of the arrangement is that the low frequency sub-image is taken for normal incidence ($NA_{ill}=0$); each of the offset sub-images is at $NA_{ill}+G/\lambda=2$ which can be achieved with grazing incidence illumination through the substrate along with a grating with a period of $\lambda/0.5$.

Figure 23:
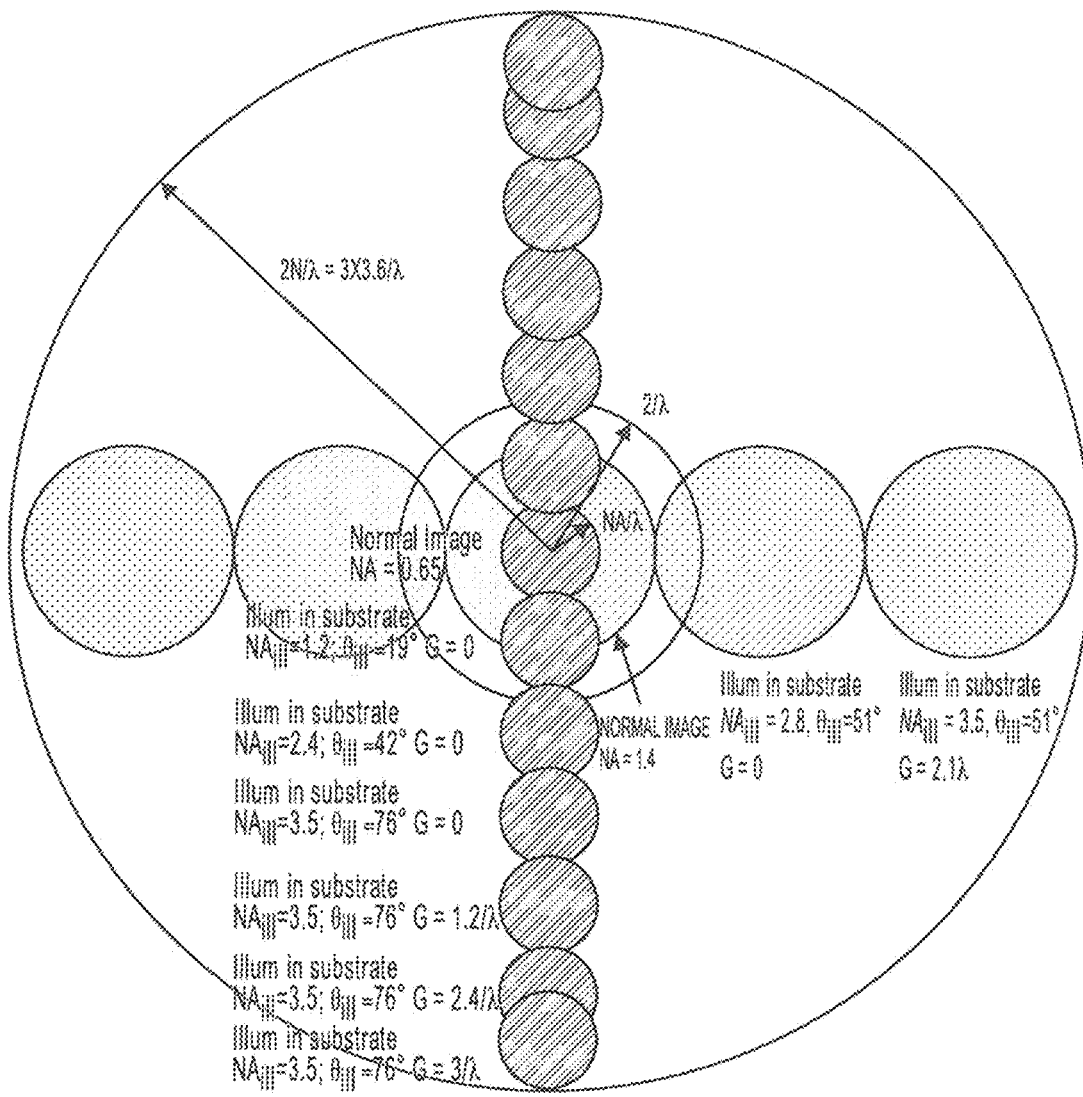
FIG. 23 show another exemplary tiling strategy for high index substrate (n=3.6, collection NA=0.65, as in FIG. 18), in accordance with various embodiments.

FIG. 23 provides two similar 1D tiling strategies for a silicon substrate ($n_{sub}=3.6$ at 1064 nm), one (vertical) for a 0.65 NA and another (horizontal) for a 1.4 NA conventional immersion objective. As many as seven sub-images may be used to provide a complete coverage along just one axis for the 0.65 NA, whereas only three are sufficient for the large NA. The area of frequency space, and the required number of sub-images for nearly complete coverage, increases as $n_{sub}^2$ or $n_{pp}^2$. Scaling from FIG. 20A suggests that as many as $(3.6/1.5)^2 \times 13 \sim 75$ sub-images would be required for full coverage with the 0.64 NA objective. This suggests that there will be great advantage in knowing something about the image and its spectral content. One situation where this is clearly possible is in the inspection of silicon integrated circuits. The demands of manufacturable lithography at the nanoscale are forcing lithographers to restrict the range of patterns allowed in modern integrated circuits. This is often referred to as lithography "friendly" design, which in general is forcing the patterns closer to periodic grating patterns. In turn, a lithography "friendly" circuit is a microscopy "friendly" circuit with a limited range of spatial frequencies, hence complete coverage of spatial frequency space is not required to reconstruct an image. Immersion lenses are not available at an NA corresponding to the refractive index of silicon (3.6). An available immersion lens designed for more modest NAs of ~1.4 can be used with the addition of gratings to couple the higher spatial frequency light out of the substrate or plane parallel optical element. An issue with the very high NA immersion lens is that these lenses typically have a very short working distance, which in turn will require a very thin substrate or plane parallel optical element, or a specially designed objective.

In implementations, immersion advantages of IIM can be realized if the object is in close proximity to a solid-immersion medium with illumination and collection through a plane-parallel optical element and coupling this radiation to air by one or more gratings on the medium surface opposite the object. The plane-parallel optical element differs from the substrate, as discussed above, in at least one manner, which is that the substrate functions, at least in part, to support the object. The plane-parallel optical element, as discussed further below, is of such a size and thickness that it cannot alone function to support the object. In implementations, a mechanical coupler can be used to support the object and optically couple the object with the plane-parallel plate. The plane-parallel optical element can be characterized by a homogeneous refractive index ($n_{pp}$) and a thickness ($t_{pp}$), such that a distance of separation between the plane-parallel optical element and the object can be within a wavelength of the light used to illuminate the object.

In implementations, the plane-parallel optical element can include high index of refraction materials to function as a solid-immersion medium. When used in IIMM, the plane-parallel optical element can have a thickness ($t_{pp}$) of about a fraction of the illumination wavelength, which allows use of strongly absorbing materials. By way of a non-limiting example, the wavelength can be chosen to be shorter than the band gap of the immersion material to take advantage of the increasing refractive index within an absorption band. In such an example, both the shorter wavelength and the larger index can extend the resolution will beyond those conventionally available with other known linear system microscopy implementations, even within the same $\lambda/4n_{pp}$ linear-systems frequency-space limit, where $n_{pp}$ is the refractive index of the plane parallel optical element.

IIMIIM can be adapted for solid-immersion in a variety of ways. For example, a high-index plane-parallel optical element can be placed very close to the object (within range of the evanescent fields). The plane-parallel optical element can be a multilayer structure or a confined liquid and can be at least partially transparent at the IIMIIM wavelength. Experiments conducted by the inventors have shown a resolution<$\lambda/5$ for IIMIIM of high contrast for chrome-on-glass objects on plane-parallel optical element composed of glass by illumination through the evanescent fields of the plane-parallel optical element and conventional collection in air (including off-axis contributions). For compactness, this configuration is referred to below as half-immersion (e.g. the illumination takes advantage of the higher wave vectors in the plane-parallel optical element, but the collection is limited to scattered wave vectors that propagate in air). For this configuration, the limiting optical resolution, in the Abbe sense of the smallest available half-pitch (HP) in the optical response, is $\lambda/[2(n_{pp}+1)]$.

The resolution can be further extended by collection of the back-scattered light that propagates within the plane-parallel optical element beyond the angle for total internal reflection. This scattering corresponds to larger wave numbers and therefore to information on smaller details of the sample. A grating can be used on the back side of the plane-parallel optical element, opposite the side or surface facing the object or sample being imaged, to extract this scattered information, making it accessible to the optical collection system. There are spatial-frequency-dependent distortions associated with the spreading of the information as it propagates across the plane-parallel optical element and extends spatially beyond the field of view of the collection system, and phase aberrations associated with this extended propagation, which require a mechanism or protocol for transforming the image from the laboratory frame to the image frame for combination with other sub-images. This mechanism or protocol can be used to compensate for frequency and/or phase discrepancies that can result from the optical configuration. The linear systems limit is a resolution of $\lambda/4n_{pp}$; resolution very close to this limit can be achieved in many cases, however with interrelated requirements on the field-of-view, the numerical aperture, and the thickness and refractive index of the plane-parallel optical element.

As discussed herein, the relationship between these parameters and the number of required sub-images are quantified and the transformation procedure for sub-images for deep sub-wavelength cases with full immersion, including single and multiple backside sub-images is discussed. The techniques described herein can use one or more gratings displaced from the object by the thickness of the plane-parallel optical element to extract waves propagating in the plane-parallel optical element beyond the angle for total internal reflection and make them available for collection in free space.

In a non-immersion IIMIIM optical arrangement, the result is the capture of a sub-image consisting of a separate region of frequency space in each sub-image. In air, the maximum angle of illumination can approach 90°, but is smaller in the plane-parallel optical element as a result of refraction at the air-plane-parallel optical element interface. By coupling into internal modes of the plane-parallel optical element, grazing incidence in the plane-parallel optical element can be achieved, increasing the resolution. IIMIIM relies on recording and combining sub-images to produce a final image that covers all of the essential, object dependent, parts of frequency space.

Using only a modest NA=0.4 lens at $\lambda$=633 nm and an object coupled to a plane-parallel optical element with refractive index $n_{pp}$, a half-immersion imaging resolution technique with evanescent wave illumination is disclosed to a maximum spatial frequency of $(n_{pp}+NA)/\lambda$ with the objective normal to the plane-parallel optical element (e.g. un-tilted objective; 170 nm features on a glass plane-parallel optical element with $n_{pp}$=1.5) and up to $(n_{pp}+1)/\lambda$ with a tilted objective (150 nm features of arbitrary structures, while the theoretical limit of grating HP resolution is 126 nm). A grating coupler can be added to the side of the plane-parallel optical element opposite the object to collect the spatial frequency information between $(n_{pp}+NA)/\lambda$ and $(n_{pp}+1)/\lambda$ as well as extending the spatial frequency coverage towards $2n_{pp}/\lambda$. Phase and amplitude matching of the sub-images can be achieved electronically using a reference object containing spatial frequencies within each recorded sub-image.

The illumination and collection configurations for half-immersion and full-immersion are shown in FIG. 24A. The illumination laser beam, from the first optical system as shown and described above in relation to FIGS. 3 and 4 can be coupled into the plane-parallel optical element 2405 using one or more optical components including, but not limited to, a prism, a grating or end fire coupling, as shown in FIGS. 12 and 13 and the object 2410 can be illuminated by an evanescent wave. Image frequencies up to $(n_{pp}+NA)/\lambda$ can be captured with an second optical system having an objective normal to the plane-parallel optical element surface (FIG. 24A, objective A 2420A), and frequencies up to $(n_{pp}+1)/\lambda$ with tilt of the objective off of the optic axis (FIG. 24A, objective B 2420B). The evanescent waves from higher frequency content of the object 2410 are coupled back into the plane-parallel optical element by the boundary conditions at the plane-parallel optical element-object interface, and for spatial frequencies between $(n_{pp}+1)/\lambda$ and $2n_{pp}/\lambda$ propagate in the plane-parallel optical element 2405 at angles beyond the angle for total internal reflection. For a flat interface, the information at these spatial frequencies is not accessible, but the scattered light can be decoupled by one or more grating structures on the side of the plane-parallel optical element 2405. The plane-parallel optical element 2405 can include a surface that is opposite the object 2410 and can include the one or more grating structures 2415, each with grating structure having its own characteristic position, period, depth, and/or grating profile. Radiation can be redirected by the one or more grating structures to an objective positionable on the opposite side of the plane-parallel optical element then the sample (FIG. 24A, objective C 2420C). This optical system (the required coherent reference beam is not shown) leads to frequency aliasing as a result of the grating diffraction. While this can be corrected with the reference beam, it is usually preferable to offset the sub-image spatial frequencies to lower intermediate frequencies to reduce the pixel size and density requirement on the collection system focal plane and restore the actual frequencies computationally before combining sub-images. In addition, there are phase errors (aberrations) associated with the collection system which includes partial propagation both in the high-index plane-parallel optical element and in air. The treatment of these spatial frequency and phase corrections is discussed below.

The corresponding frequency space coverages achievable using the apparatus configurations of FIG. 24A are shown in FIG. 24B. Normal incidence illumination, and collection from the sample side is the traditional coherent illumination configuration represented by the circle 2405 with frequency space coverage to $NA/\lambda$. Illumination at an angle of $2NA/\lambda$ provides the offset circles 2410 with frequency space coverage to $3NA/\lambda$. For a Manhattan geometry object, two sub-images providing coverage in the x,y directions is typically used, additional sub-images, indicated by the circles 2415 (at 45° to the principal x,y axes) can be added for additional off-grid frequency space coverage. The illumination and sample-side collection scheme of objective position A of FIG. 24B allows increasing the spatial frequency coverage to $(n_{pp}+NA)/\lambda$ (circles 2420). Collection with a tilted objective, as shown with objective position B of FIG. 24A, allows frequency space coverage to $(n_{pp}+1)/\lambda$. Finally, the plane-parallel optical element side collection discussed in this contribution, objective position C of FIG. 24A, extends the frequency space coverage to the linear systems limit of $2n_{pp}/\lambda$ with a corresponding Abbe half-pitch of $\lambda/4n_{pp}$.

FIGS. 25A-D show four example arrangements for the plane-parallel optical element 2405 with respect to the object 2410 that can be used with optical arrangement shown in FIG. 24 according to implementations of the present disclosure.

FIG. 25A shows the plane-parallel optical element 2405 as a membrane 2505 having support members 2510 on at least a portion of the membrane 2505, wherein the membrane 2505 is optically coupled with the object 2515. In this arrangement, thickness of the membrane 2505 is typically not sufficient to fully physically support the object 2515. Therefore, the support members 2510 can function, at least in part, to add strength or resiliency to the membrane 2505. The membrane 2505 can include a first surface 2520, which is arranged on the side of objectives A and B, and a second surface 2525, which can include one or more gratings 2530 and is arranged on the side of objective C.

FIG. 25B shows the plane-parallel optical element 2405 as a superstrate 2535. In this arrangement, the object 2515 can be positioned between a support 2540, for example, a substrate, on one side and a superstrate 2535 on the other side. The superstrate 2535 can be arranged on the side of objective C and can include one or more gratings 2545. The lower frequency information, collected by objectives A and B can be extracted either from the top surface 2515 of the superstrate 2535 or from the bottom surface of the substrate 2540. Substrate 2540 can be locally thinned (not shown) to reduce optical aberrations in the collection system.

FIG. 25C shows the plane-parallel optical element 2405 as a multilayer superstrate 2550. In this arrangement, which is similar to the arrangement shown in FIG. 25B, one or more materials can be used in the multilayer superstrate 2550, including superstrate layers 2550a and 2550b, wherein each material can have a specific thickness and optical characteristic, including different indexes of refraction. Although only two layers are shown in the figure, more than two layers for the superstrate can be used. In this arrangement, the object 2515 can be positioned between a support 2540, for example, a substrate, on one side and a multilayer superstrate 2550 on the other side. The superstrate 2550 can be arranged on the side of objective C and can include one or more gratings 2545. The lower frequency information, collected by objectives A and B can be extracted either from the top surface of the superstrate 2550 or from the bottom surface of the substrate 2540. Substrate 2540 can be locally thinned (not shown) to reduce optical aberrations in the collection system.

FIG. 25D shows the plane-parallel optical element 2405 as a suspended superstrate 2555. In this arrangement, which is similar to the arrangement shown in FIG. 25B, suspended superstrate 2555 can be supported above the object 2515 by one or more intermediate materials. For example, the one or more intermediate materials can be in a fluid form and each material can have a specific volume and optical characteristic, including different indexes of refraction. In this arrangement, the object 2515 can be positioned between a support 2540, for example, a substrate, on one side and a suspended superstrate 2555 on the other side. The superstrate 2555 can be arranged on the side of objective C and can include one or more gratings 2545. The lower frequency information, collected by objectives A and B can be extracted either from the top surface 2545 of the superstrate or from the bottom surface of the substrate 2540. Substrate 2540 can be locally thinned (not shown) to reduce optical aberrations in the collection system.

In each of the arrangements shown in FIGS. 25A-D, the separation distance between the plane-parallel optical element and the object 2510 is within the wavelength of the light used to illuminate the object 2515.

IIM requires reintroducing a coherent zero-order reference at the image plane (e.g. constructing an interferometer around the objective lens) to record the amplitude and phase of the spectral frequencies in the sub-images. The intensity, angle and phase of the reference beam have to be chosen to match all sub-images to the on-axis image. A reference object is used to cover a small part of the FOV in order to determine the correct amplitude ratio, frequency shift and phase. These offset frequencies can then corrected in the image processing before the sub-images are combined.

In the description that follows, elements including ray tracing (looking at the propagation of scattered rays corresponding to specific spatial frequencies) and Fourier optics (based on "infinite" plane wave propagation) are both presented. To bring these two concepts together, "wave packets" will be considered with center spatial frequencies that correspond to the direction of propagation and with a spatial extent that corresponds to the field-of-view, which is assumed to be much larger than the individual scattering objects within the field, but much smaller than the diameter of the lens. This corresponds to a broadening in the pupil plane and Fourier planes from the delta functions associated with plane waves to diffraction patterns corresponding to the finite field of view.

Figure 26:
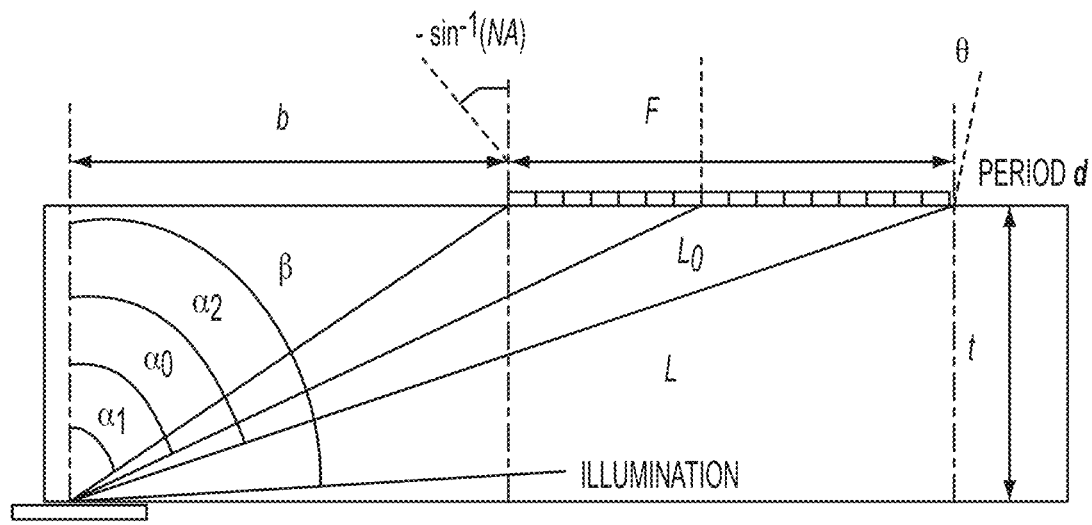
FIG. 26 shows an example geometry that shows access to collection high frequencies propagating in the plane-parallel optical element that correspond to small features.

In embodiments, additional scattered information can be collected at spatial frequencies beyond $(n_{pp}+NA)/\lambda$ by collection from the back side of the plane-parallel optical element using one or more gratings to redirect this information into an objective lens. FIG. 26 shows an example geometry that shows access to collection high frequencies propagating in the plane-parallel optical element that correspond to small features. As can be seen from the geometry of FIG. 26, the spatial frequency coverage of each sub-image depends on the thickness and refractive index of the plane-parallel optical element as well as on the field-of-view (FOV) and NA of the objective lens. For thicker plane-parallel optical elements, the relevant information is spread across a wider area requiring a larger FOV. This may require multiple spatially displaced sub-images to extract all of the information (a synthetic FOV). If the available information extends beyond the $2NA/\lambda$ bandwidth of the collection optics, multiple gratings are required (a synthetic aperture). The minimum collected spatial frequency (angle $\alpha_1$ in FIG. 26) sets the period d of the extraction grating:

$$d = \frac{\lambda}{n_{pp}\sin\alpha_1 + NA} \quad (8)$$

If this frequency equals the maximum available from half immersion without a tilted objective, $(n_{pp}+NA)/\lambda$, then:

$$d = \frac{\lambda}{2NA}. \quad (9)$$

This takes a scattered wave in the plane-parallel optical element corresponding to $$k_{\alpha_1} = k_0 NA = n_{pp}k_0 \sin\alpha_1 = n_{pp}k_0 \sin[\sin^{-1}(NA/n_{pp})] \quad (10)$$

into a wave propagating in air at an angle $-\sin^{-1}(NA)$. Here, $k_0 \equiv 2\pi/\lambda$. Note that provided NA>0.33, higher diffraction orders from the grating are outside the NA of the collection optics and do not interfere with the image; an NA=0.4 is considered in the modeling. Over the range of spatial frequencies collected in each sub-image the diffraction efficiencies are roughly constant, thus allowing intensity compensation by sub-image matching procedures. This technique tends to be free of the complications connected with multiple diffraction orders from gratings encountered by other approaches. In embodiments, the gratings can provide extraction of information out of the immersion media but not diffraction of near-field high-spatial frequency components directly from the object. There can be variations in diffraction efficiency as the various higher order beams, in both the plane-parallel optical element and in air, switch from evanescent to propagating waves. These can be dealt with empirically by adjusting the amplitudes of the relevant portions of each sub-image independently, either by physically restricting the collection NA appropriately, or by separately addressing the regions of the sub-image electronically.

Progressively higher spatial frequency components impinge on the grating at larger horizontal displacements from the object and are diffracted into increasing angles, until the scattered beam at a displacement of b+F from the object centerline is diffracted at to an angle of +θ in air. The distance F corresponds to the FOV of the objective lens, which can be taken as focused on the grating surface, or to the width of the grating if it is smaller than the FOV.

Provided $\theta \leq \sin^{-1}(NA)$, the entire spread of scattered light incident on the grating is collected by the objective lens. From the geometry of FIG. 25, several important relationships are readily derived:

$$\sin(\alpha_1) = \frac{NA}{n_{pp}} = \frac{b}{\sqrt{b^2+t^2}}; \quad (11)$$

$$b = t\left[\left(\frac{n_{pp}}{NA}\right)^2 - 1\right]^{-1/2}$$

and $$\sin(\alpha_2) = \frac{b+F}{\sqrt{(b+F)^2+t^2}} \quad (12)$$

$$= \left[1+\left(\frac{b+F}{t}\right)^{-2}\right]^{-1/2}$$

$$= \left\{1+\left[\frac{F}{t}+\left(\left(\frac{n_{pp}}{NA}\right)^2-1\right)^{-1/2}\right]^{-2}\right\}^{-1/2}$$

and the corresponding minimum half pitch is:

$$HP_{min} = MAX\left\{\begin{array}{l}\frac{\lambda}{2(n_{pp}+3NA)}; \\ \frac{\lambda}{2n_{pp}\left\{1+\left\{1+\left[\frac{F}{t}+\left(\left(\frac{n}{NA}\right)^2-1\right)^{-1/2}\right]^{-2}\right\}^{-1/2}\right\}}\end{array}\right\} \quad (13)$$

The upper expression (Eq. 11) is valid when the full NA of the objective lens is filled by the diffracted beams from the grating, e.g. the grating width F, and the optical FOV and NA are such that $\theta \geq \sin^{-1}(NA)$. If the angular spread is restricted by the field of view, or equivalently by the width of the grating, the lower expression (Eq. 12) pertains. An additional constraint is that $3NA < n_{pp}$, since only spatial frequencies that can propagate in the plane-parallel optical element can be collected. The limiting behavior of $HP_{min}$ is readily evaluated from this expression. For small NA where the full angular width of the lens is filled, the upper expression (Eq. 11) applies. For all interesting cases, $NA/n_{pp} \ll 1$; that is the lens NA is much less than the refractive index of the immersion medium. For large fields of view or thin plane-parallel optical elements, $F/t \gg NA/n_{pp}$, $$HP_{min} \to \frac{\lambda}{n_{pp}[4-(t/F)^2]}.$$

Thus, $HP_{min}$ is always larger than the optics linear systems limit. The upper limit in Eq. 13 takes over before this result; thus the NA of the lens is filled in just a single sub-image. Additional gratings at smaller pitches of $\lambda/2(i+1)NA$ [i=1, 2, 3, . . . ] allow access to higher spatial frequency components of the image up to the linear systems limit of $\lambda/4n$. In the opposite limit, $NA/n_{pp} \ll 1$ and $F/t \ll NA/n_{pp}$, $$HP_{min} \to \frac{\lambda}{2\left(n_{pp} + NA + \frac{n_{pp}F}{t}\right)}.$$

The resolution is always somewhat improved over the starting point of half-immersion with the collection system optical axis normal to the object plane. In this case the linear systems limit of $\lambda/4n_{pp}$ can be approached with a synthetic FOV, e.g. multiple sub-images with the collection optical system displaced to collect the higher spatial frequencies that are lost by the limited FOV with the same grating, and again, with multiple gratings (synthetic aperture), it is possible to extend the resolution close to the $\lambda/4n_{pp}$ limit, as long as signal/noise ratio is sufficient to enable sub-image reconstruction into a full image.

Figure 27:
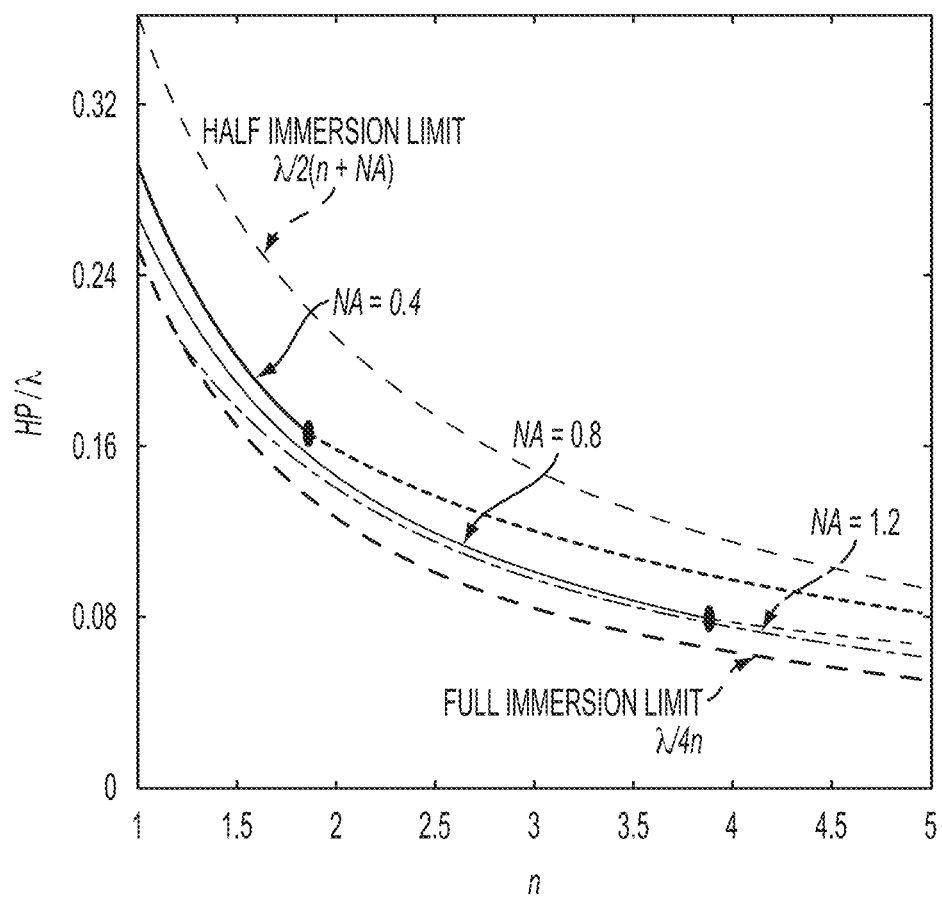
FIG. 27 shows a plot depicting resolution restriction: normalized HP versus index of refraction for different NA (0.4,
0.8, 1.2), fixed plane-parallel optical element thickness: t=50 μm and field of view 32 μm, where the solid lines represent the dependence described by the lower part of Eq. 13 and the dashed lines represent the dependence described by the upper part of Eq. 13.

Resolution (HP) restrictions as a function of plane-parallel optical element refractive index for NA=0.4, 0.8, 1.2, fixed field of view (F=32 μm) and plane-parallel optical element thickness (t=50 μm) obtained from Eq. 13 are shown in FIG. 27. There is a point of transition on each curve (solid to dotted). The solid lines correspond to the upper expression of Eq. 13; the dotted lines to the lower form. In the dotted region additional sub-images are required to synthesize a larger FOV. Once the lens NA is filled, an additional grating is required to extract higher spatial frequency information and alias it into the lens NA, e.g. to synthesize a larger NA.

Figure 28:
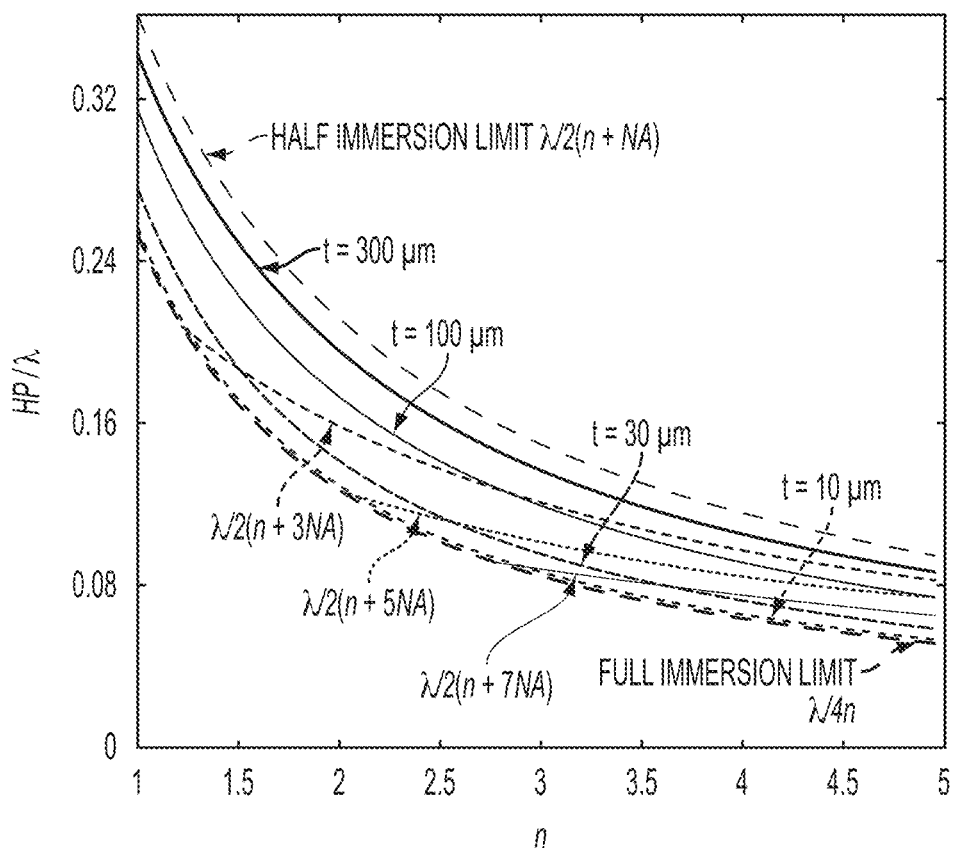
FIG. 28 shows a plot depicting resolution restriction: normalized HP versus index of refraction for different plane-parallel optical element thickness: 10, 30, 100, 300 μm calculated with NA=0.4, F=32 μm in different synthetic aperture steps, where the long dashed lines represent the inside of synthetic aperture up to $\lambda/[2(n_{pp}+3NA)]$, the dashed lines represent the inside of synthetic aperture up to $\lambda/[2(n_{pp}+5NA)]$, and the dotted lines represent the inside of synthetic aperture up to $\lambda/[2(n_{pp}+7NA)]$.

Exemplary combination of restrictions induced by plane-parallel optical element properties and synthetic aperture (multiple of NA=0.4) for a fixed field of view (F=32 μm) with varying plane-parallel optical element thickness are shown in FIG. 28. One of ordinary skill in the art would appreciate that the combination of restrictions tends to change as the numerical aperture (NA) changes. The curves correspond to plane-parallel optical element thicknesses of 10, 30, 100 and 300 μm with break points denoted by the transitions from dashed to dotted lines by curves of synthetic NA restrictions. Here, $\lambda/[2(n_{pp}+3NA)]$ corresponds to upper part of Eq. 13. The restrictions $\lambda/[2(n_{pp}+5NA)]$ and $\lambda/[2(n_{pp}+7NA)]$ appear by synthetic aperture extension with 1 and 2 additional aperture intervals along each spatial direction using adapted gratings for each interval as described above.

It can be inferred from FIGS. 27 and 28 that, for a single sub-image, a small NA optical system can give useful resolution extensions only for materials with low index of refraction. In order to reach high resolution using materials with high $n_{pp}$, either additional sub-images using multiple gratings or an objective with higher NA is needed. A larger FOV objective enhances the resolution but typically is associated with lower NA, which again requires additional sub-images. A compromise between FOV and NA has to be found for the chosen plane-parallel optical element thickness and index of refraction to minimize the total number of sub-images. These models do not include the impact of a finite signal-to-noise ratio (S/N). As the signal becomes more dispersed with thicker plane-parallel optical elements, the S/N decreases and stochastic contributions to the image become more significant limiting the ability to accurately combine the sub-images and construct a composite image.

Figure 29A:
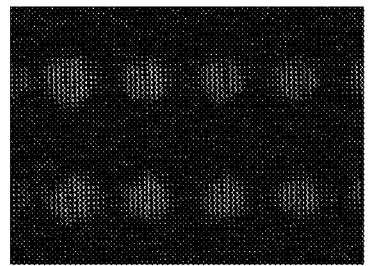
FIG. 29A shows an SEM image of periodic structure, HP=120 nm; 29B shows an IIM sub-image for t=2 mm and decoupling grating half-pitch of 280 nm.
Figure 29B:
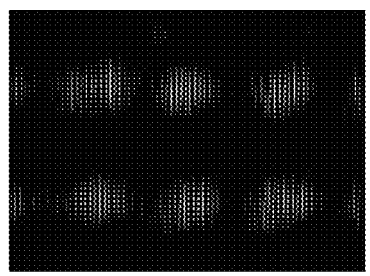

Initial experiment were conducted using a 1-mm thick glass plane-parallel optical element optically coupled to a second 1-mm thick microscope slide with a metal decoupling grating of period 560 nm. Thus the total thickness (object to grating) is 2 mm. The results showed the possibility of resolution of a periodic structure. The image consists of a repeated pattern of several parallel lines with a spacing of 240 nm within a trapezoidal envelope. The pattern is repeated at a spacing of 3.6 μm in both directions. A SEM image is shown in FIG. 29A. The x-direction high frequency image was recorded and is shown in FIG. 29B. The high frequency image contains much of the information about the original pattern: the repeated pattern is evident as is the clustering of lines in each repeat unit. However, the image is distorted due to the geometry of propagation in the plane-parallel optical element [FIG. 24(b)] and requires a restoration procedure before the proper image can be recovered. Clearly there are fewer clusters at the same transverse scale (3 vs. 4) in the distorted image, the relative spacing between the line clusters is changed and there are additional lines in the clusters, though the line pitch remains the same The distortion of the image as a result of the propagation in the and depends on the optical path in the plane-parallel optical element, e.g. on the plane-parallel optical element refractive index and thickness. The optical configuration was shown in FIG. 24, with the collection lens focused onto the grating surface. Since an aberration-free optical system has no phase error between conjugate planes, e.g. the grating surface and the camera focal plane, the only phase variations needed to be considered are for propagation in the plane-parallel optical element (FIG. 26). For analytical simplicity, a one dimensional case is considered; the calculations are readily extended to two dimensional objects. Let L and $L_0$ be optical paths of an arbitrary and of the central ray in the plane-parallel optical element, $\alpha$ and $\alpha_0$ are the angles of the corresponding rays to the plane-parallel optical element normal. $\theta$ is the angle of the arbitrary ray to the optical axis after diffraction from the grating and exiting the plane-parallel optical element (the ray must be captured by the objective in air and for convenience is shown as a marginal ray). The angle $\alpha_0$ of the ray in the plane-parallel optical element which is redirected along the optical axis in air is:

$$\sin\alpha_0 = \frac{\lambda}{n_{pp}d} = \frac{2NA}{n_{pp}} \quad (14)$$

The marginal ray inclined at the angle $\alpha_2$ to the normal in the plane-parallel optical element and an angle $\theta$ in air after scattering by the grating is described by:

$$\sin\alpha_2 = \frac{1}{n_{pp}}\left(\frac{\lambda}{d} + \sin\theta\right) \quad (15)$$

Then the path lengths in the plane-parallel optical element are:

$$L_0 = \frac{t}{\cos\alpha_0} = \frac{t}{\sqrt{1-\sin^2\alpha_0}} = \frac{t}{\sqrt{1-\left(\frac{\lambda}{n_{pp}d}\right)^2}} \quad (16)$$

$$L = \frac{t}{\cos\alpha_2} = \frac{t}{\sqrt{1-\sin^2\alpha_2}} = \frac{t}{\sqrt{1-\left[\frac{1}{n_{pp}}\left(\frac{\lambda}{d}+\sin\theta\right)\right]^2}} \quad (17)$$

and the phase difference between the arbitrary ray and the central ray is $$\Delta\varphi = \varphi - \varphi_0 = \frac{2\pi n_{pp}t}{\lambda}\left[\frac{1}{\sqrt{1-\left[\frac{1}{n_{pp}}\left(\frac{\lambda}{d}+\sin\theta\right)\right]^2}} - \frac{1}{\sqrt{1-\left(\frac{\lambda}{n_{pp}d}\right)^2}}\right]. \quad (18)$$

The rays in FIG. 26 are k-vectors of the plane waves propagating at angles θ corresponding to the image spatial frequencies $f_x$. So, the phases at each spatial frequency can be corrected in Fourier space using the distortion phase function provided by the 2D generalization of Eq. 18. Clearly that distortion phase function (Eq. 18) provides only a relative phase correction. The constant term (the phase shift introduced by the central ray optical path) will be automatically corrected later by the sub-image phase-matching procedure required in IIM, since this constant term is indistinguishable from arbitrary constant term introduced by the phase of the reference arm of the Mach-Zehnder interferometer inherent in IIM.

Figure 30A:
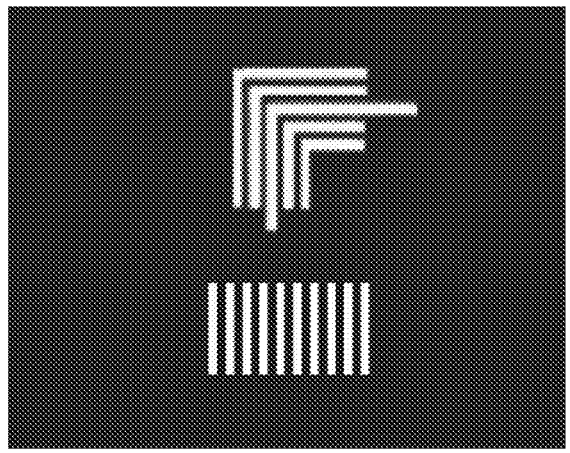
FIG. 30A shows a model CD=120 nm structures and 30B shows an x-direction high frequency image.
Figure 30B:
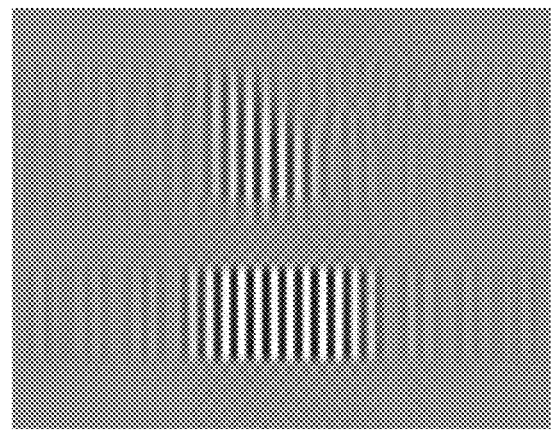
Figure 31B:
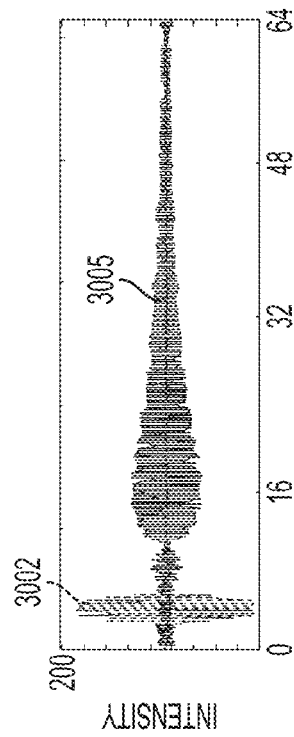
FIGS. 31A-31D show difference in expansion of spectral package (120 nm features) for different plane-parallel optical element thicknesses (n=1.5, F=64 μm), where for FIG. 31A, t=1 μm, image expansion ~3 times and for FIG. 31B, t=5 μm, image expansion ~10 times; comparison of filtered image crosscuts (3002) with FIG. 31C showing crosscuts of images (3005) distorted by substrate propagation with t=1 μm, and FIG. 31D showing crosscuts of images (3005) distorted by plane-parallel optical element propagation with t=5 μm.
Figure 31D:
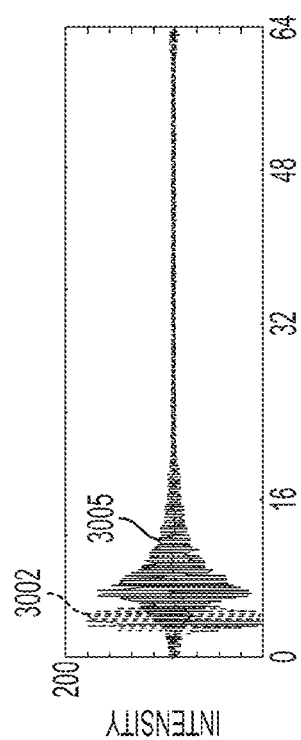
Figure 31A:
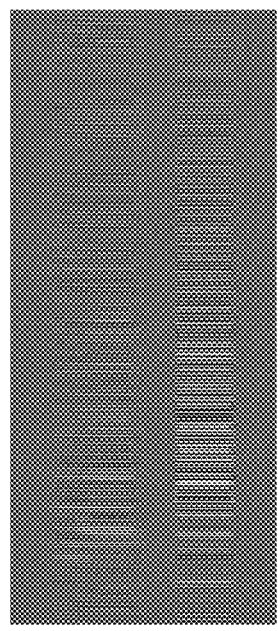
Figure 31C:
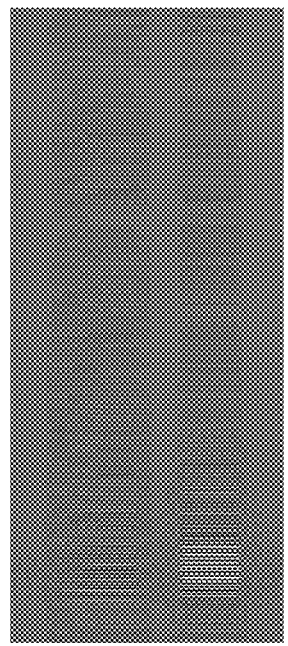

Simulation of the impact of this phase distortion on the image with nested-L structure and a delimited grating with CD=120 nm (FIG. 30A) is shown in FIG. 31. The high spatial frequency (between NA/λ and 3NA/λ) filtered image of the model is shown in FIG. 30B. The image is expanded, e.g. additional features appear on both sides of object due to lack of compensation in these regions as a result of the optical bandwidth limit. This is just the familiar Gibbs effect associated with an abrupt cut-off in frequency space. The high frequency image after the application of the phase aberrations for a plane-parallel optical element thickness of 1 μm [5 μm] is shown in FIG. 31A [FIG. 31B] (crosscut FIG. 31C) [FIG. 31D]. There is additional walk-off of the intensity vs. position as a result of the spreading of the image intensity. The reason for this spread is the progressive walk-off of higher spatial frequency components (phase distortions) as they propagate across the plane-parallel optical element. Here, the additional features appear non-symmetrically to the illumination side. Also, unlike the Gibbs effect, no information is lost in general. The step from FIG. 30B to FIGS. 31A and 31B are completely deterministic and is easily inverted by taking the Fourier transform of the laboratory frame image, applying the inverse of Eq. 18 and retransforming back to the image frame providing all information is captured and there are no S/N limitations. The spatial extent of the image spectrum expands with increasing plane-parallel optical element thickness (compare FIGS. 31A and 31B). The intensity spread extension beyond the objective field of view leads to the loss of information which results in reduction of the image quality after restoration. This information can be accessed with a synthetic FOV, e.g. shifting the objective lens to acquire additional sub-images with an extended grating at the same pitch.

Without shifting the objective lens, the loss of information is equivalent to the reduction of captured range of frequencies ($NA_{pp}$<NA) for a single sub-image, which is a function of the FOV. To evaluate this degradation of the image bandwidth in a single image, consider again FIG. 26, but now in a configuration where the grating is chosen so that a particular $HP_c$ is along the optical axis, e.g. fix the optical axis (center) frequency rather than the low-frequency marginal ray. The dependence of the angular bandwidth, $2NA_{pp}$, versus the FOV is easily to obtain from FIG. 26. The FOV (F) normalized to the slab thickness is:

$$\frac{F}{t} = \tan\alpha_2 - \tan\alpha_1 \quad (19)$$

On the other hand the marginal angles for a particular $NA_{sub}$-??????sub or pp can be written as function of an angle $\sin\alpha_c$ of the center frequency, corresponding to the chosen $HP_c$.

$$\sin\alpha_2 = \sin\alpha_c + NA_{pp} \quad (20)$$

and $$\sin\alpha_1 = \sin\alpha_c - NA_{pp}, \quad (21)$$

where, for an illumination angle sin β:

$$\sin\alpha_c + \sin\beta = \frac{\lambda}{2n_{pp}HP_c} \quad (22)$$

Combining Eqs. 19-21 gives an implicit relation for the optical system parameters $$\frac{F}{t} = \frac{\sin\alpha_c + \frac{NA_{pp}}{n_{pp}}}{\sqrt{1-\left(\sin\alpha_c + \frac{NA_{pp}}{n_{pp}}\right)^2}} - \frac{\sin\alpha_c - \frac{NA_{pp}}{n_{pp}}}{\sqrt{1-\left(\sin\alpha_c - \frac{NA_{pp}}{n_{pp}}\right)^2}} \quad (23)$$

This dependence shown in FIG. 31 for several $HP_c$ normalized by n and λ

$$\left(g = \frac{n_{pp}HP_c}{\lambda}\right)$$

allows us to define $NA_{pp}$ of each sub-image and to estimate the number of sub-images which are necessary to cover the of the available spatial frequency space (along a specific direction).

Figure 32:
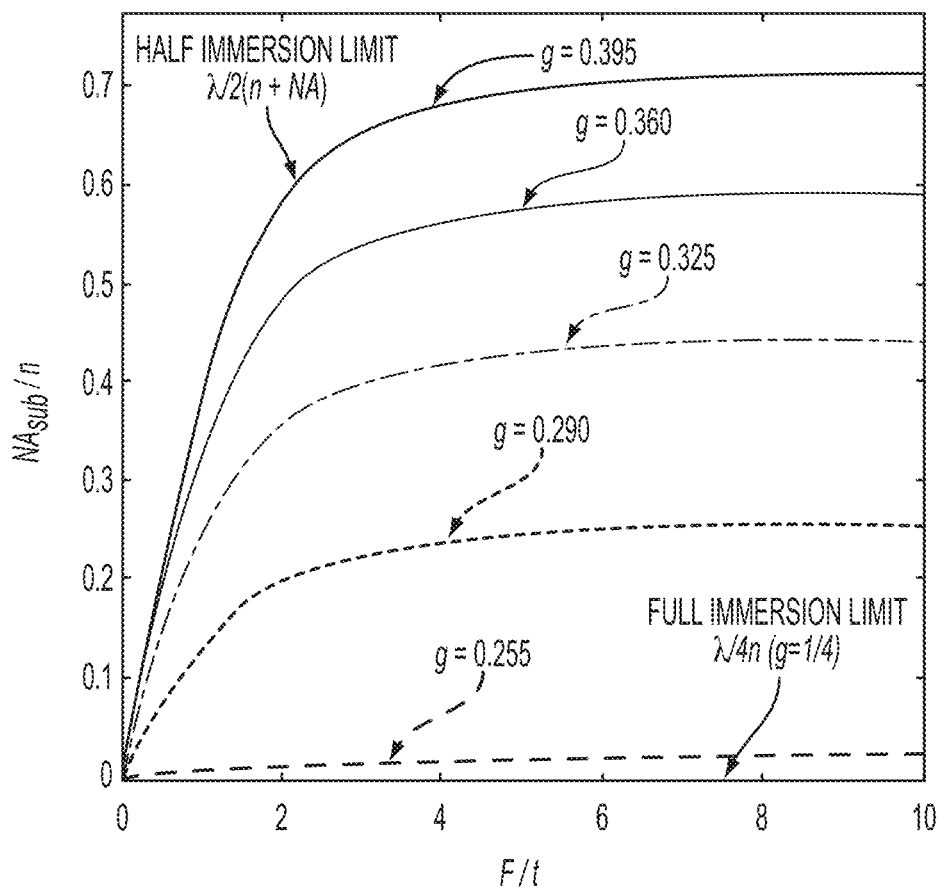
FIG. 32 show a plot depicting synthetic aperture guideline: normalized sub-image bandwith $2NA_{sub}$ versus normalized FOV for different extracting gratings represented by center frequency $$HP_c\left(g = \frac{n_{pp}HP_c}{\lambda}\right).$$

It can be seen from FIG. 32 that, in order to prevent the loss of information, an objective with a bigger FOV or additional spatially shifted sub-images to build a synthetic FOV is needed. These conclusions are qualitatively the same as those drawn from FIGS. 27 and 28.

Examples of images shown in FIGS. 31A-31D restored using a FOV of 16 μm are shown with corresponding crosscuts 3005 in comparison with the undistorted image 3205 and differences between the restored and filtered crosscuts in FIG.

Figure 33:
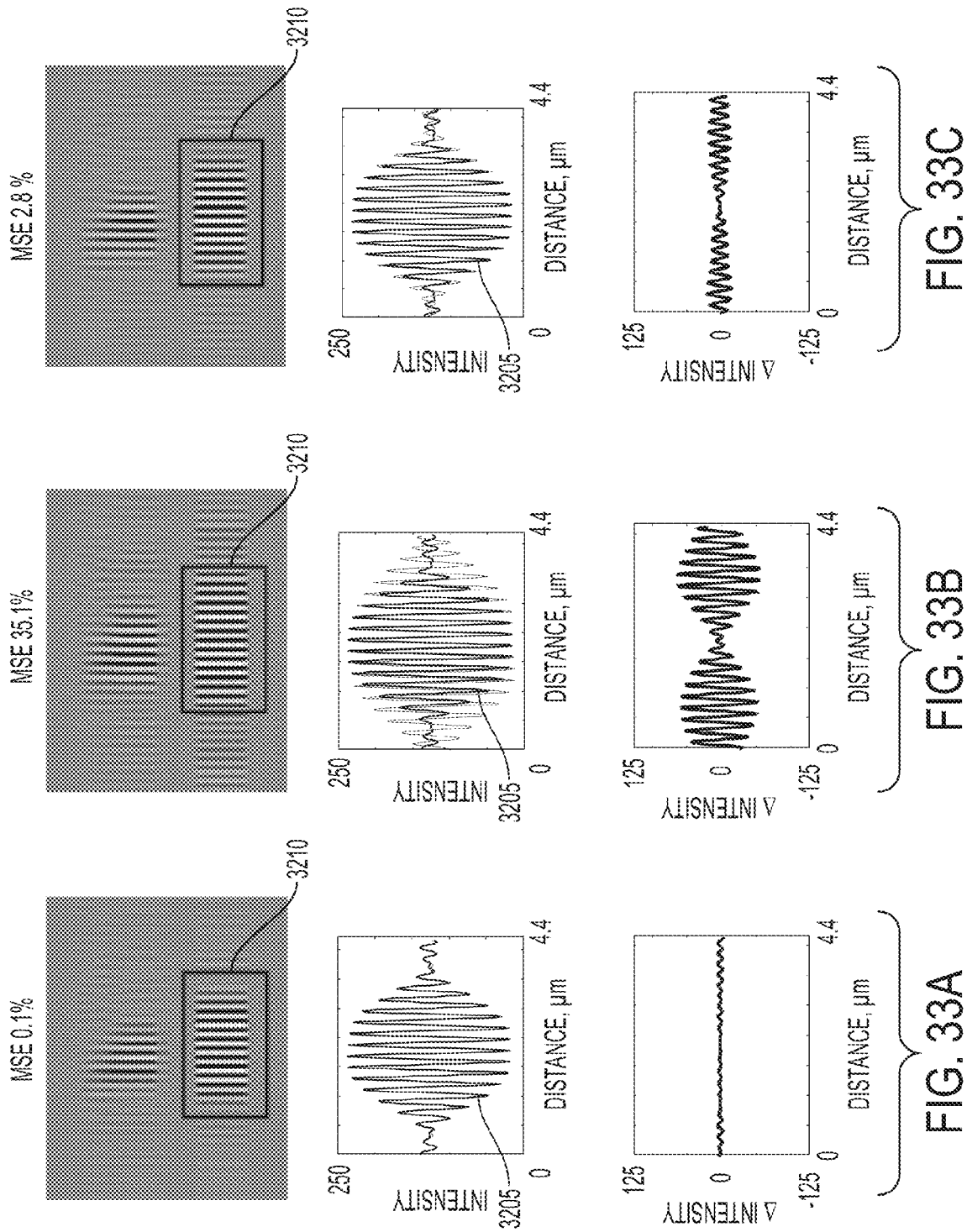
FIG. 33 shows FIGS. 33A-33C depicting restored images (CD=120 nm, $n_{pp}$=1.5), crosscuts and crosscut differences.

33. FIG. 33A is obtained from FIG. 31A and FIG. 33B from FIG. 31B. It is clear that the sub-image in FIG. 31A for a 1 µm thick plane-parallel optical element is extended less than the sub-image in FIG. 31B for a 5 µm thick plane-parallel optical element and the quality of restored image in FIG. 33A is higher than in FIG. 33B. Extension of recorded field of view to 32 µm for the image in FIG. 31B improves the quality of restored image [FIG. 33C], showing the complex interrelationships between the resolution, FOV, NA, plane-parallel optical element thickness and the refractive index.

Figure 34:
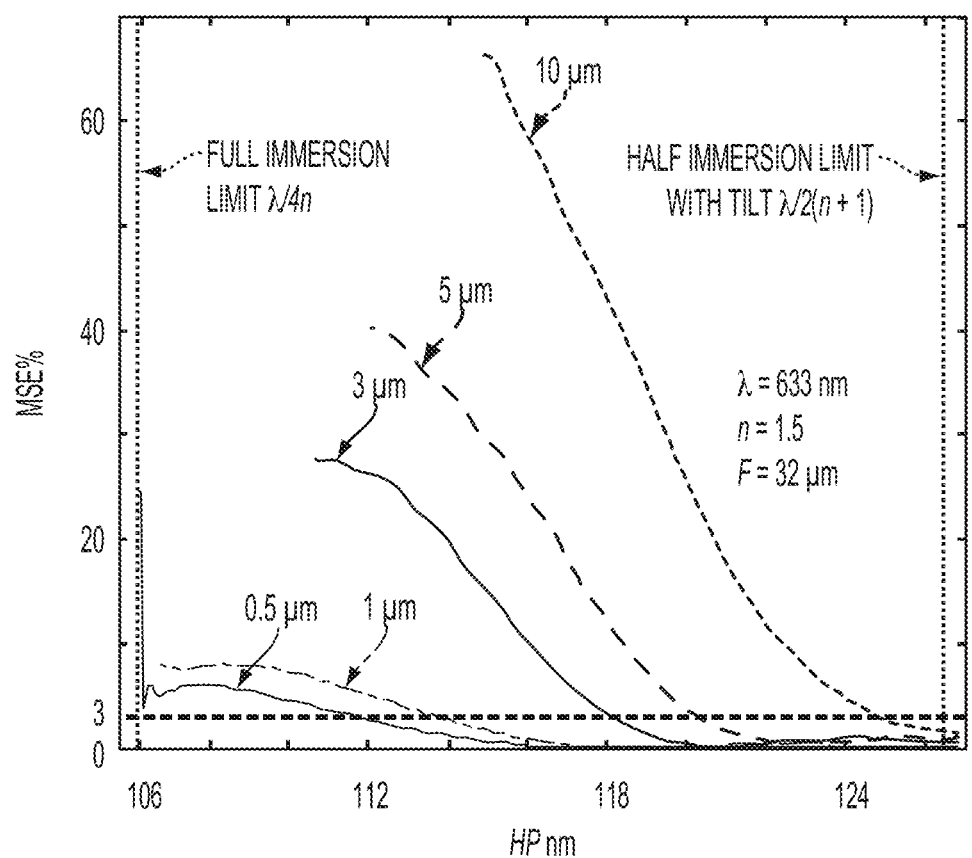
FIG. 34 shows of plot of MSE versus HP of a 10-line pattern for different plane-parallel optical element thicknesses, n=1.5; F=32 μm; λ=633 nm. 3% MSE considered as images with acceptable quality. 0.5 μm plane-parallel optical element allows restoration of images with 112 nm features, 1 μm~113.5 nm, 3 μm 118 nm, 5 μm~120 nm, 10 μm~124 nm.

For an additional perspective on the ability to restore these images, the restored images with different HP were compared with the filtered high frequency images using a mean square error (MSE) metric. A simple ten-line grating pattern was chosen for MSE analyses (inside of the square 3210 of FIGS. 33A-C) and normalized to a gray field (FIG. 34). The curves of MSE versus HP for a λ=633 nm, $n_{sub}$=1.5 plane-parallel optical element thicknesses of 0.5, 1, 3, 5, 10 µm and a restoration FOV of 32 µm are shown. For a comparable MSE procedure, it is important to have the spectral content of the image filtered similarly. Thus, it is ensured that the center frequency at the HP always passes through the center of the collection objective, as in the derivation of Eq. (23).

These calculations were carried out from the theoretical limit $\lambda/4n_{pp}$=0.106 µm to the half immersion limit $\lambda/(n_{pp}+1)$= 0.126 µm (λ=633 nm, $n_{sub}$=1.5). The MSE drops as image becomes resolvable. As expected, the distortion (expansion of the frequency content across the detection plane) of image features is lower in thinner films which allows higher resolution with a smaller FOV.

The same models were used for plane-parallel optical elements with different refractive indices in order to evaluate possible resolvable HP with MSE=3% for plane-parallel optical element thicknesses of 1-, 5-, and 10-µm. The results are summarized in FIG. 34, where the resolvable HP versus refractive index are shown. The lower black dashed curve λ/4n is theoretical limit of full immersion resolution, the black upper dashed line $\lambda/2(n_{pp}+NA)$ is the half-immersion limit with an un-tilted objective.

Figure 35:
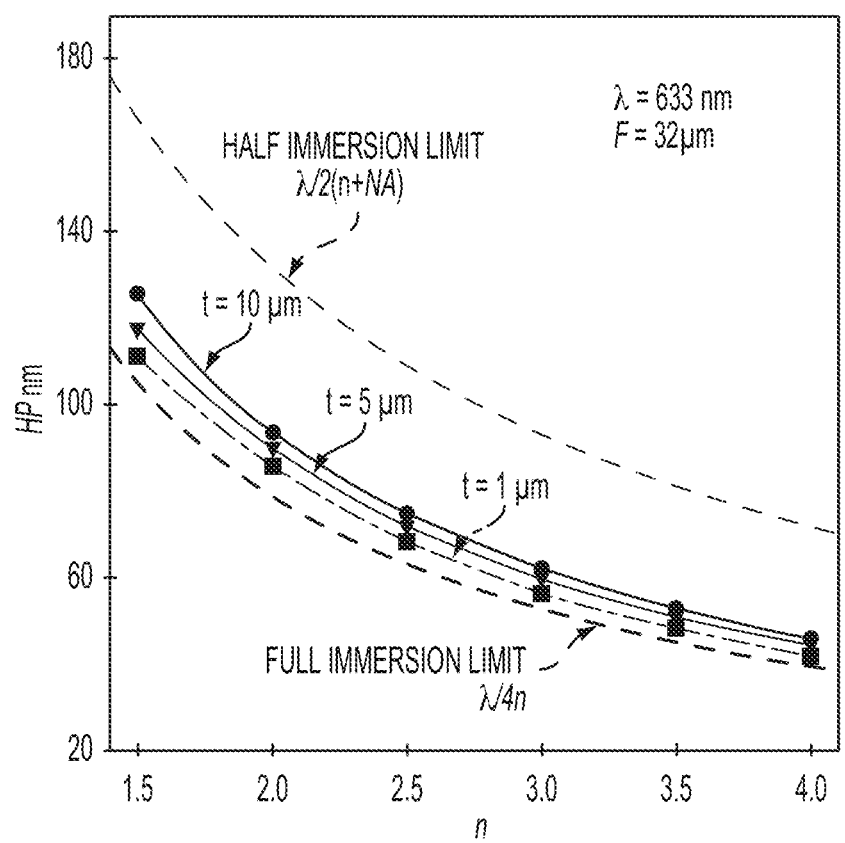
FIG. 35 shows a plot of HP versus n for different plane-parallel optical element thicknesses: 1, 5, 10 μm (F=32 μm), λ=633 nm. Plane-parallel optical elements with higher $n_{pp}$ allows resolution and restoration of images with smaller features.

The modeling of image reconstruction represented in FIG. 35 qualitatively confirms the results obtained by investigation of theoretical resolution limit (FIG. 28). The image resolution depends on the optical system and plane-parallel optical element properties (NA, FOV, $t_{pp}$ and $n_{pp}$). The achievable resolution scales inversely with the plane-parallel optical element index of refraction. Plane-parallel optical element thicknesses greater than several times the FOV result in experimental difficulties, both in registration and in lowered signal intensity leading to S/N issues.

The present techniques of the IIM configuration, as discussed above, with a slab of high refractive index material can be used as an effective solid-immersion medium to enhance the resolution up to the linear systems resolution limit of $\lambda/4n_{pp}$. Phase distortions of high frequency sub-images are inherent in the geometry of beam propagation in the immersion slab, requiring a phase restoration procedure. The resolution in this configuration depends not only on the objective NA and FOV, but also on the captured part of the spectral information which is also a function of immersion slab refractive index and thickness. The criteria for evaluation of the ultimate HP limits for different immersion slab parameters and system field of view have been provided. The estimation shows that the minimum thickness of the immersion slab and the maximum field-of-view of the optical system should be chosen to achieve the highest resolution with the smallest number of sub-images.

Embodiments of the present disclosure allow a regime for IIM not achievable with conventional approaches. Using very thin plane-parallel optical elements (or overlayers) and thereby restricting the propagation distance, higher absorption can be tolerated, allowing the use of shorter wavelengths. Then the resolution can be improved by two factors: the shorter wavelength; and the higher index of refraction within an absorption band. The present approaches provide resolutions that are not available to solid immersion microscopy approaches as a result of the need for a thick high-index solid immersion lens.

Table I provides calculated resolutions for several microscopy techniques and compares their practical resolution achievements for different λ with a silicon immersion plane-parallel optical element.

TABLE I

Wavelength dependent resolution on Si plane-parallel optical element for different techniques

| | Wavelength (nm) | | | | |
| --- | --- | --- | --- | --- | --- |
| | 1064 | 704 | 633 | 488 | 430 |
| | Si properties | | | | |
| Si refractive index | 3.56 | 3.77 | 3.9 | 4.37 | 4.91 |
| Si 1/e length (µm) | 1070 | 6.5 | 3.5 | 0.98 | 0.31 |
| Double pass transmission (0.5 µm) | 0.99 | 0.86 | 0.74 | 0.36 | 0.04 |
| | Alternative approaches | | | | |
| Annular illumination (NA = 1.3) λ/4 NA | 205 | 135 | 122 | 94 | 83 |
| SIL λ/4n (thick lens does not allow materials with loss) | 75 | — | — | — | — |
| | IIM | | | | |
| λ/4 (no immersion) | 266 | 176 | 158 | 122 | 108 |
| $\lambda/[2(n_{pp}+1)]$ (half immersion) | 115 | 74 | 65 | 45 | 36 |
| $\lambda/4n_{pp}$ (full immersion) | 75 | 47 | 41 | 28 | 22 |

Annular illumination using the ~2× resolution advantage of off-axis illumination can be combined with immersion techniques (current results are with liquid immersion and an NA=1.3). However this requires alignment between two specialized high NA, small FOV objectives which is a challenging task. Even ignoring the fact that usually there is a tradeoff between the FOV and the NA, such objectives cannot use materials with significant losses, as a result of the required macroscopic optical thicknesses.

Solid immersion lenses (SIL) provide a relatively cost-effective solution for increasing NA by a combination of standard objective with section of high index refraction sphere as solid immersion media. This method has shown good resolution (to 145 nm using a Si SIL at 1.2 µm) but again can only be used with relatively long wavelengths since the sphere section (which in practice is close to a hemisphere) requires essentially lossless materials. To the contrary, IIM can provide up to few tens of nanometers resolution with immersion media such as silicon at visible (red to green) wavelengths while retaining the full field of view, large working distance, depth of field, and low-cost of low NA objectives.

Other materials coupled with wavelengths in proximity to a material band-gap in combination with our method can also provide excellent results. Some possible wavelength/material combinations to explore are shown in Table II.

TABLE II

Examples of possible combinations of materials and
wavelength for enhanced resolution

| λ (nm) | λ/4 (nm) | immersion λ/4n$_{max}$ |
|---|---|---|
| 633 | 158 | 48 (n$_{pp}$ = 3.3, GaP) |
|  |  | 40 (n$_{pp}$ = 4.0 Si) |
| 488 | 122 | 50 (n$_{pp}$ = 2.45, GaN) |
|  |  | 27 (n$_{pp}$ = 1.8, Photoresist) |
| 193 | 48 | 23 (n$_{pp}$ = 2.1, Garnet) |
|  |  | 19 (n$_{pp}$ = 2.6, Si$_3$N$_4$) |

Thus IIM can be very useful for imaging small features using thin immersion slab with high n$_{sub}$ where resolution approaches that of a SEM with a simple inexpensive technique that is applicable in a range of environments including air and water.

Imaging interferometric microscopy techniques as described above are sensitive to the optical refractive index variation of the object materials and does not contain any material specific information. Imaging interferometric microscopy can be applied to get material and chemical information using coherent anti-Stokes Raman scattering (CARS) spectroscopic microscopy. An apparatus for coherent anti-Stokes Raman (CARS) microscopy can include any suitable optical arrangement as shown in FIGS. 1, 3, 5A-5E, 12A, 12B 13A-13C, 18, 19, and 24. In particular, the apparatus for CARS microscopy can include an object plane 122, 222, 1222, 1822 on which can be disposed a first surface of a planar substrate 125, 225, 1225, 1825 or plane-parallel optical element 2405, wherein the substrate 125, 225, 1225, 1825 can be characterized by a homogeneous refractive index (n$_{sub}$) and a surface normal 226, 1226, 1826 and plane-plane parallel optical element 2405 can be characterized by a homogeneous refractive index (n$_{pp}$) and a surface normal 2406. The apparatus for CARS microscopy can also include a first optical system disposed to provide a illumination of the object plane 122, 222, 1222, 1822, the illumination characterized by two substantially coincident coherent beams 110, 110', 210, 210', with wavelengths λ$_1$ and λ$_2$ and corresponding angular frequencies ω$_1$ and ω$_2$ with ω$_1$>ω$_2$, a radius of curvature, and disposed at one of a plurality of incident wave vectors from about 0 to about 2πn$_{sub}$/λ$_1$ or 2πn$_{pp}$/λ$_1$ with respect to a surface normal of the substrate 125, 225, 1225, 1825 or plane-parallel optical element 2405 and at a multiplicity of azimuth angles spanning 0 to 2π. The apparatus for CARS microscopy can also include a second optical system (collection) 130, 230, 530, 1230, 1830, or 2420A-C having an optical axis 136, 236, 536, 1236, 1836, 2406 disposed at one of a plurality of center wave vectors from about 0 to about 2πn$_{sub}$/λ$_1$ or 2πn$_{pp}$/λ$_1$ with respect to the surface normal, wherein the second optical system 130, 230, 530, 1230, 1830, 2420A-C is characterized by a numerical aperture (NA) or NA$_{pp}$ and is responsive primarily to optical signals at frequencies greater than ω$_1$. The apparatus for CARS microscopy can further include a third optical system disposed in an optical path of the first optical system to provide interferometric reintroduction of a reference illumination (reference beam) at a frequency of 2ω$_1$−ω$_2$, into the second optical system 130, 230, 530, 1230, 1830, 2420A-C wherein each of an amplitude, a phase, a radius of curvature and an angle of incidence of the reference is adjusted as required such that a corrected reference wave is present at the image plane of the second optical system 130, 230, 530, 1230, 1830, 2420A-C. The apparatus for CARS microscopy can also include an electronic image device disposed at an image plane 124, 224 of the second optical system 130, 230, 530, 1230, 1830, 2420A-C that responds linearly to the local optical intensity and transfers the local optical intensity map across the image plane (a sub-image) to a signal processor device in electronic form, a signal processor that receives the electronic form of the sub-image and manipulates the sub-image to correct for distortions and alteration introduced by the optical configuration, and an electronic device to sequentially collect, store and combine a plurality of sub-images corresponding to a plurality of regions of spatial frequency space to create a composite image, wherein the plurality of sub-images are formed as a result of adjustments to the first, the second, and the third optical systems.

In various embodiments, the third optical system of the apparatus for CARS microscopy can include a first beamsplitter disposed in the optical path of the first optical system before the object plane 122, 222, 1222, 1822, 2425 to collect a portion of the coherent illumination and one or more optics disposed between the first optical system and the second optical system 130, 230, 530, 1230, 1830, 2420A-C wherein the optics includes a nonresonant nonlinear material configured to generate the anti-Stokes four-wave mixing frequency 2ω$_1$−ω$_2$ and exclude the fundamental frequencies (ω$_1$ and ω$_2$), and to interferometrically reintroduce the portion of the anti-Stokes coherent illumination as a reference beam into the second optical system 130, 230, 530, 1230, 1830, 2420A-C in a position after the exit aperture of a collection (objective) lens, wherein the reintroduction is at one of a position corresponding to a position a zero-order beam would have had if it had been transmitted through an appropriate higher NA lens of the second optical system 130, 230, 530, 1230, 1830, 2420A-C as shown in FIG. 1 or an aliased position to reduce pixel requirements of the electronic image device, wherein the signal processor is adjusted to compensate for this spatial frequency aliasing.

In various embodiments, the third optical system of the apparatus for CARS microscopy can include one of the third optical system configurations shown in FIGS. 5A-5E. In some embodiments, the apparatus for CARS microscopy can include a third optical system 500E in a configuration shown in FIG. 5E. The third optical system can include a first beamsplitter disposed in the optical path of the first optical system before the object plane 522 to collect a portion of the coherent illumination one or more transfer optics disposed between the first optical system and the second optical system 530, wherein the optics includes a nonresonant nonlinear material 520 configured to generate the anti-Stokes four-wave mixing frequency 2ω$_1$−ω$_2$ and exclude the fundamental frequencies (ω$_1$ and ω$_2$), and a second beamsplitter 570 disposed between the object plane 522 and a front aperture of a collection lens (objective) of the second optical system 530 to reintroduce the portion of the anti-Stokes coherent wave illumination as a reference beam 510' into the second optical system 530 at an angle θ less than the entrance angular aperture (<~sin$^{-1}$NA) of the second optical system 530.

In other embodiments, the apparatus for CARS microscopy can include a third optical system 500D in a configuration shown in FIG. 5D. The third optical system 500D can further include a first beamsplitter disposed in the optical path of the first optical system to collect a portion of the coherent illumination, one or more transfer optics disposed between the first optical system and the second optical system, wherein the optics includes a nonresonant nonlinear material configured to generate the anti-Stokes four-wave mixing frequency 2ω$_1$−ω$_2$ and exclude the fundamental frequencies (ω$_1$ and ω$_2$). The third optical system 500D can also include at least one of a grating 584 or a grating on a waveguide disposed between the object plane 522 and a front aperture of the collection lens (objective) of the second optical system 530 to reintroduce the portion of the anti-Stokes coherent wave illumination as a reference beam 510' into the second optical system 530 at an angle θ less than the entrance angular aperture ($<\sim\sin^{-1}$ NA) of the second optical system 530.

In other embodiments, the apparatus for CARS microscopy can include a third optical system 500A in a configuration shown in FIG. 5A. The third optical system 500A can further include a first beamsplitter disposed in the optical path of the first optical system to collect a portion of the coherent illumination, one or more transfer optics, wherein the one or more optics can include a nonresonant nonlinear material configured to generate the anti-Stokes four-wave mixing frequency $2\omega_1-\omega_2$ and exclude the fundamental frequencies ($\omega_1$ and $\omega_2$) and wherein at least one of the one or more optics is disposed to direct the portion of the anti-Stokes coherent plane wave illumination as a reference beam to illuminate the object at an angle θ corresponding to less than the entrance angular aperture ($<\sim\sin^{-1}$ NA) of the second optical system 530. The third optical system 500A can also include a dynamic (on/off) physical block 550 disposed in a back pupil plane of the second optical system 530 to alternately block and unblock a small portion of the pupil aperture corresponding to the position of the reference beam 510' in the aperture.

In various embodiments, the apparatus for CARS microscopy can include a third optical system 500C in a configuration shown in FIG. 5C. The third optical system 500C can further include a first beamsplitter disposed in the optical path of the first optical system to collect a portion of the coherent illumination, one or more transfer optics, wherein the one or more optics can include a nonresonant nonlinear material configured to generate the anti-Stokes four-wave mixing frequency $2\omega_1-\omega_2$ and exclude the fundamental frequencies ($\omega_1$ and $\omega_2$) and wherein at least one of the one or more optics is disposed to direct the portion of the anti-Stokes coherent plane wave illumination as a reference beam to illuminate the object at an angle θ corresponding to less than the entrance angular aperture ($<\sim\sin^{-1}$ NA) of the second optical system 530. The third optical system 500C can also include a guided-mode resonance filter (k-vector filter) 582 disposed between the object plane 522 and a collection lens of the second optical system 530 and an another device (not shown) to adjust the position, tilt and rotation of the guided-mode resonance filter 582 between positions, tilts and rotations in which it alternately transmits and blocks the portion of the reference beam transmitted through the object plane.

In certain embodiments, the apparatus for CARS microscopy can also include at least one known reference object to cover a small part of the image field. In some embodiments, the first, the second, and the third optical systems can be arranged in a transmission configuration.

In other embodiments, the first, the second, and the third optical systems can be arranged in a reflection configuration. In some embodiments, the plurality of incident wave vectors of the first optical system can include wave vectors less than about $2\pi/\lambda_1$ wherein these wave vectors are accessed by illumination of the substrate at polar angles between 0 and π/2. In other embodiments, the plurality of incident wave vectors of the first optical system can include wave vectors between about $2\pi/\lambda_1$ and about $2\pi n_{sub}/\lambda_1$ or $2\pi n_{pp}/\lambda_1$, wherein these wave vectors are accessed by evanescent wave illumination of the object through the substrate. Furthermore, the apparatus for CARS microscopy can use any of the arrangements shown in FIGS. 13A-13C for coupling light into the substrate for illumination through the substrate 125, 225, 1225, and 1825 or plane-parallel optical element 2405.

In some other embodiments, the plurality of center wave vectors of the second optical system 130, 230, 530, 1230, 1830, 2420A-C can include only center wave vectors less than about $2\pi/\lambda_1$, wherein these center wave vectors are accessed by an optical system above the object plane of the substrate 125, 225, 1225, 1825 or plane-parallel optical element 2405. In certain embodiments, the plurality of center wave vectors of the second optical system 130, 230, 530, 1230, 1830, 2420A-C can include center wave vectors between $2\pi/\lambda_1$ and $2\pi n_{sub}/\lambda_1$ or $2\pi n_{pp}/\lambda_1$, wherein the center wave vectors greater than $2\pi/\lambda_1$ are accessed through the substrate 125, 225, 1225, 1825 or plane-parallel optical element 2405 and the second optical system 130, 230, 530, 1230, 1830, 2420A-C can include one or more gratings on the side of the planar substrate 125, 225, 1225, 1825 or one or more gratings 2415 on the side of the plane-parallel optical element 2405 opposite the object plane 122, 222, 1222, 1822, 2425 wherein each grating is characterized by a position, a pitch, and a grating profile.

According to various embodiments, there is a method for coherent anti-Stokes Raman (CARS) microscopy. The method for CARS microscopy can include providing an object 120, 220, 1220, 1820, 2410 disposed over a planar substrate 125, 225, 1225, 1825 or plane-parallel optical element 2405, wherein the substrate 125, 225, 1225, 1825 is characterized by a homogeneous refractive index ($n_{sub}$) and a surface normal and wherein the plane-parallel optical element 2405 is characterized by a homogeneous refractive index ($n_{pp}$) and a surface normal and providing a first optical system disposed to provide a illumination of the object plane 122, 222, 1222, 1822, 2425 the illumination characterized by two substantially coincident coherent beams with wavelengths $\lambda_1$ and $\lambda_2$ and corresponding angular frequencies $\omega_1$ and $\omega_2$ with $\omega_1 > \omega_2$, a radius of curvature, and disposed at one of a plurality of incident wave vectors from about 0 to about $2\lambda n_{sub}/\lambda_1$ or $2\pi n_{pp}/\lambda_1$ with respect to a surface normal 126, 226, 1226, 1826, 2406 of the substrate 125, 225, 1225, 1825 or plane-parallel optical element 2405 and at a multiplicity of azimuth angles spanning 0 to 2π. The method can also include providing a second optical system (collection) 130, 230, 1230, 1830, 2420A-C having an optical axis 136, 236, 1236, 1836, 2406 disposed at one of a plurality of center wave vectors from about 0 to about $2\pi n_{sub}/\lambda_1$ or $2\pi n_{pp}/\lambda_1$ with respect to the surface normal 125, 225, 1225, 1825, 2406 wherein the second optical system 130, 230, 1230, 1830, 2420A-C is characterized by a numerical aperture (NA) and is responsive primarily to optical signals at frequencies greater than $\omega_1$ and providing a third optical system disposed in an optical path of the first optical system to provide interferometric reintroduction of a reference illumination (reference beam) at a frequency of $2\omega_1-\omega_2$, into the second optical system 130, 230, 1230, 1830, 2420A-C wherein each of an amplitude, a phase, a radius of curvature and an angle of incidence of the reference is adjusted as required such that a corrected reference wave is present at the image plane of the second optical system 130, 230, 1230, 1830, 2420A-C. The method can further include providing an electronic image device disposed at an image plane of the second optical system 130, 230, 1230, 1830, 2420A-C that responds linearly to the local optical intensity and transfers the local optical intensity map across the image plane (a sub-image) to a signal processor device in electronic form, providing a signal processor that receives the electronic form of the sub-image, manipulating the sub-image using the signal processor to correct for distortions and alteration introduced by the optical configuration, providing an electronic device to sequentially collect, store and combine a plurality of sub-images corresponding to a plurality of regions of spatial frequency space to create a composite image, wherein the plurality of sub-images are formed as a result of adjustments to the first, the second, and the third optical systems, and combining the plurality of sub-images into a composite image to provide a substantially faithful image of the object 120, 220,1220, 1820, 2410.

According to various embodiments, the method can further include one or more processes of subtraction of dark field images, subtraction of background images, shifting of spatial frequencies in accordance with the optical configuration, and elimination of one or more overlapping coverages of the frequency space wherein the elimination operations can be performed either in the optical systems or in the signal processing. In some embodiments, the method can further include selecting regions of spatial frequency space to provide a more or less faithful image of the object 120, 220, 1220, 1820, 2410 in the object plane 122, 222, 1222, 1822, 2425.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. As used herein, the symbol "n" or "$n_{sub}$" will mean the index of refraction of the substrate when used in context to the substrate, unless otherwise expressly noted. For example, $n_{clad}$ represents the index of refraction of a cladding.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for microscopy comprising:
    providing a plane-parallel optical element operable to be positioned adjacent to an object, wherein the plane-parallel optical element is characterized by a homogeneous refractive index ($n_{pp}$) and a thickness ($t_{pp}$), such that a distance of separation between the plane-parallel optical element and the object is within about a wavelength of illumination light incident upon the object;
    providing a first optical system disposed to provide a substantially coherent illumination of the object, wherein the illumination light is characterized by a wavelength $\lambda$, a radius of curvetre a center position, and a field-of-view and disposed at one of a plurality of incident wave vectors from about 0 to about $2\pi_{pp}/\lambda$ with respect to a surface normal of the plane-parallel optical element and at a plurality of azimuth angles spanning about 0 to $2\pi$;
    providing a second optical system including one or more optical components defining an optical axis which is disposed on a side of the plane parallel optical element, the second optical system including a first set of optical media characterized by indices of refraction and thicknesses in which light scattered by the object propagates to a first optical component of the second optical system, an effective numerical aperture (NA) of the combined one or more optical components of the second optical system, a focal plane of the second optical system conjugate with an image plane of an optical image recording device, and a field-of-view in the focal plane, wherein the optical axis of the second optical system is disposed at one of a plurality of angles between 0 and $\pi/2-NA$ with respect to the surface normal of the plane-parallel optical element, the field-of-view of the second optical system is located at a center offset from a center position of the illumination provided by the first optical system, and wherein the one or more optical components of the second optical system are operable to collect at least a portion of the illumination scattered by the object;
    providing a third optical system disposed in an optical path of the first optical system to provide interferometric reintroduction of a portion of the coherent illumination as a reference beam into the third optical system, wherein each of an amplitude, a phase, a radius of curvature, a path length, and an angle of incidence of the reference beam is adjustable such that a reference illumination suitable for interfering with the portion of the illumination scattered by the object and collected by the second optical system is present at an image plane of the second optical system;
    recording a sub-image of the object at an image plane of the second optical system using the image recording device, wherein the sub-image is formed as a result of interference between the scattering resulting from the coherent illumination of the object and the reference beam;
    adjusting the first, the second, and the third optical systems to collect a plurality of sub-images corresponding to a plurality of regions of the object spatial frequency space; and
    combining the plurality of sub-images into a composite image to provide an image of the object.

2. The method of claim 1, wherein the second optical system further comprises one or more gratings on an outward facing surface of the plane parallel optical element, away from the object, the grating being in a far field region of the scattering of the illumination by the object, wherein each grating is characterized by a position, including a center position and a spatial extent, a period, and a grating profile and wherein each grating is operable to decouple a subset of coherent radiation scattered by the object at angles that are beyond the NA of the second optical system into the first optical medium of the second optical system at angles smaller than $\pm\sin^{-1}(NA)$ of the second optical system.

3. The method of claim 2, further comprising: translating the center offset of the field of view of the second optical system, relative to a center of the field-of-view of the first optical system, to collect subsets of the illumination scattered from the object.

4. The method of claim 3, wherein the translation of the center offset of the field-of-view of the second optical system is within an extent of a single grating for which a width of the spatial extent of the grating is greater than the field-of-view of the second optical system, thereby effecting an increased field-of-view of the second optical system.

5. The method of claim 3, wherein the translation of the center offset of the field-of-view of the second optical system is larger than a width of a first grating of the one or more gratings, resulting in the field-of-view of the second optical system being positioned over a second grating of the one or more gratings with a different pitch from the first grating, thereby accessing a different subset of scattered waves from the object.

6. The method of claim 2, wherein one or more sub-images are recorded with the optical axis of the second optical system on a side of the plane parallel optical element opposite the object, normal to the plane-parallel optical element, and the field-of-view of the second optical system is positioned over one of the one or more gratings, thereby collecting and recording additional spatial frequencies of the illumination scattered by the object.

7. The method of claim 1 wherein the plane-parallel optical element provides a substrate function in providing mechanical support for the object.

8. The method of claim 1 wherein the plane-parallel optical element is a superstrate that is held within about an illumination wavelength of the object.

9. The method of claim 1, wherein one or more sub-images are recorded with the optical axis of the second optical system on the same side of the plane parallel optical element as the object and at an angle between about 0 and about $\pi/2-NA$ relative to the n al of the plane-parallel optical element and the center of field-of-view of the second optical system is positioned over a center of the field-of-view of the first optical system.

10. The method of claim 1, further comprising manipulating each of the sub-images to correct for distortions and alterations introduced by the combinations of the first, the second, and the third optical systems.

11. The method of claim 1, wherein providing a third optical system further comprises: collecting a portion of the coherent illumination by splitting the coherent illumination using a beam splitter disposed in an optical path of the first optical system; and interferorrretricaliy reintroducing the portion of the coherent illumination as a reference beam after an exit aperture of a collection lens of the second optical system, wherein the reintroduction is at one of a position, an amplitude, a phase, a radius of curvature, a path length, and an angle of incidence such that either a correct sub-image or an aliased sub-image with reduced spatial frequencies is produced.

12. The method of claim 1, wherein providing a third optical system further comprises: collecting a portion of the coherent illumination by splitting the coherent illumination using a beam splitter disposed in an optical path of the first optical system; and interferometrically reintroducing the portion of the coherent illumination as a reference beam using a second beam combining device before an entrance aperture of a collection lens of the second optical system, wherein the reintroduction is at an angle less than the entrance aperture of the collection lens of the second optical system, wherein the second beam combining device is selected from the group consisting of: a beamsplitter, a grating coupler, and a waveguide filter.

13. An apparatus for microscopy comprising:
a plane parallel optical element, characterized by a homogeneous refractive index ($n_{pp}$) and a thickness ($t_{pp}$),
a mechanical mechanism arranged to support an object, such that a separation between the plane parallel optical element and the object is within about a wavelength of an illumination light with which the object is illuminated;
a first optical system operable to provide a substantially coherent illumination of the object, the illumination characterized by a wavelength $\lambda$, a radius of curvature, a center position, and a field-of-view and disposed at one of a plurality of incident wave vectors from about 0 to about $2\pi n_{pp}/\lambda$, with respect to a surface normal of the plane parallel optical element and at a plurality of azimuth angles spanning about 0 to $2\pi$;
a second optical system; including one or more optical components defining an optical axis operable to be positioned on a side of the plane parallel optical element, the second optical system including a first set of optical media characterized by indices of refraction and thicknesses in which light scattered by the object propagates into the second optical system, a numerical aperture (NA) of the combined one or more optical components of the second optical system, a focal plane for the object conjugate with an image plane of an image recording device, and a field-of-view in the focal plane; wherein the optical axis of the second optical system is disposed at one of a plurality of angles between about 0 and about $\pi/2-NA$ with respect to the plane parallel optical element surface normal; the field-of-view of the second optical system is located at a center offset from the center position of the illumination provided by the first optical system, and wherein the one or more optical components are operable to collect at least a portion of the illumination scattered by the object;
a third optical system operable to be positioned in an optical path of the first optical system to provide interferometric reintroduction of a portion of the coherent illumination as a reference beam into the third optical system, wherein each of an amplitude, a phase, a radius of curvature, a path length, and an angle of incidence of the reference beam is adjustable such that a reference illumination suitable for interfering with the portion of the illumination scattered by the object and collected by the second optical system is present at an image plane of the, second optical system;
an image recording device operable to record a sub-image of the object at the image plane of the second optical system, wherein the sub-image is formed as a result of interference between the scattering resulting from the coherent illumination of the object and the reference beam;
an adjustment mechanism operable to configure the first, the second, and the third optical systems to collect a plurality of sub-images corresponding to a plurality of regions of the object spatial frequency space; and
a signal processing device operable to combine the plurality of sub-images into a composite image to provide an image of the object.

14. The apparatus of claim 13, wherein the second optical system further comprises one or more gratings on an surface of the plane-parallel optical element opposite the object, an interface being in a far field region of the scattering of the illumination by the object, wherein each grating is characterized by a position, including a center position and a spatial extent, a period, and a grating profile and wherein each grating is operable to decouple a subset of coherent radiation scattered by the object at angles that are beyond the NA of the second optical system into the first optical medium of the second optical system at angles smaller than $\pm\sin^{-1}(NA)$ of the second optical system.

15. The apparatus of claim 14, further comprising: one or more optical, mechanical, or both optical and mechanical elements operable to translate a center offset of the field of view of the second optical system, relative to the center of the field-of-view of the first optical system, to collect subsets of the illumination scattered from the object.

16. The apparatus of claim 15, wherein translation of the center offset of the field-of-view of the second optical system is within an extent of a single grating for which a width of the spatial extent is greater than the field-of-view of the second optical system, thereby effecting an increased field-of-view of the second optical system.

17. The apparatus of claim 16, wherein extent of the translation of the center offset of the field-of-view of the second optical system is larger than a width of a first grating of the one or more gratings, resulting in the field-of-view of the second optical system being positioned over a second grating of the one or more gratings with a different pitch from the first grating, thereby accessing a different subset of scattered waves from the object.

18. The apparatus of claim 13, wherein any, or a combination, of the first, the second, and the third optical systems are arranged such that one or more sub-images are recorded with the optical axis of the second optical system on a side of the plane-parallel optical element away from the side facing the object and at an angle between 0 and $\pi/2-NA$ relative to the surface normal of the plane parallel optical element and a center of field-of-view of the second optical system is positioned over a center of the field-of-view of the first optical system.

19. The apparatus of claim 14, wherein the second optical system is arranged such that one or more sub-images are recorded with the optical axis of the second optical system on an outward facing side of the plane-parallel optical element, normal to the plane-parallel optical element, and the field-of-view of the second optical system is positioned over one of the one or more gratings, thereby collecting and recording additional spatial frequencies of the illumination scattered by the object.

20. The apparatus of claim 13, further comprising one or snore electrical, optical, or both electrical and optical element operable to manipulate each of the sub-images to correct for distortions and alterations introduced by the combinations of the first, the second, and the third optical systems.

21. The apparatus of claim 13, wherein the third optical system urther includes: a one or more optical elements operable to collect a portion of the coherent illumination by splitting the coherent illumination using a beam splitter disposed in an optical path of the first optical system; and one or more optical elements operable to interferometrically reintroduce the portion of the coherent illumination as a reference beam after an exit aperture of a collection lens of the second optical system, wherein the reintroduction is at one of a position, an amplitude, a phase, a radius of curvature, a path length, and an angle of incidence such that either a correct sub-image or an abased sub-image with reduced spatial frequencies is produced.

22. The apparatus of claim 13, wherein the third optical system further includes: one or more optical elements operable to collect a portion of the coherent illumination by splitting the coherent illumination using a beam splitter disposed in an optical path of the first optical system; and one or more optical elements operable to interferometrically reintroduce the portion of the coherent illumination as the reference beam using one or more optical components before an entrance aperture of a collection lens of the second optical system, wherein the reintroduction is at an angle less than the entrance aperture of a collection lens of the second optical system, wherein the one or more optical components that are operable to reintroduce the reference beam are selected from the group consisting of: a beamsplitter, a grating coupler, and a waveguide filter.

* * * * *